United States Patent
Song et al.

(10) Patent No.: US 8,313,771 B2
(45) Date of Patent: Nov. 20, 2012

(54) PHOSPHAZENE HYDROGELS WITH CHEMICAL CORSS-LINK, PREPARATION METHOD THEREOF AND USE THEREOF

(75) Inventors: Soo-Chang Song, Namyangju-si (KR); Thrimoorthy Potta, Seoul (KR); Sun-Mi Lee, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 335 days.

(21) Appl. No.: 12/452,322

(22) PCT Filed: May 23, 2008

(86) PCT No.: PCT/KR2008/002716
§ 371 (c)(1),
(2), (4) Date: Dec. 23, 2009

(87) PCT Pub. No.: WO2008/153278
PCT Pub. Date: Dec. 18, 2008

(65) Prior Publication Data
US 2010/0297155 A1    Nov. 25, 2010

(30) Foreign Application Priority Data

Jun. 14, 2007  (KR) .......................... 10-2007-0058460
Apr. 30, 2008  (KR) .......................... 10-2008-0040662

(51) Int. Cl.
*A61K 9/14*    (2006.01)
*A61K 47/48*   (2006.01)
*C08G 69/26*   (2006.01)
*C08G 79/02*   (2006.01)
*C08G 73/00*   (2006.01)

(52) U.S. Cl. ........ 424/486; 528/272; 528/332; 528/399; 528/422; 525/54.1; 525/538; 525/540

(58) Field of Classification Search ........................ None
See application file for complete search history.

(56) References Cited

FOREIGN PATENT DOCUMENTS

| KR | 10-2001-0047025 | 6/2001 |
| KR | 10-2005-0012533 | 2/2005 |
| KR | 10-2007-0076386 | 7/2007 |
| KR | 10-0746962      | 8/2007 |

OTHER PUBLICATIONS

Kang, G.D. et al. Thermosensitive poly(organophosphazene) hydrogels for a controlled drug delivery. Eur. J. of Pharm. Biopharm. Mar. 2006, vol. 63, pp. 340-346, ISSN 0939-6411.

Hennink, W. E. et al. Novel Crosslindking Methods to Design Hydrogels. Adv. Drug Deliv. Rev. Jan. 2002, vol. 54, pp. 13-36, ISSN 0169-409X.

*Primary Examiner* — Robert A Wax
*Assistant Examiner* — Jeffrey T Palenik
(74) *Attorney, Agent, or Firm* — Lexyoume IP Meister, PLLC.

(57) ABSTRACT

A phosphazene-based polymer hydrogel with a chemical cross-linkings formed by radiating ultraviolet (UV) and/or mixing with cross-linking agent and/or enzyme, and a method of preparing the same are provided. The hydrogel shows a sol-gel behavior and has an excellent solidity by containing the phosphazene-based polymer that is capable of cross-linking at a certain concentration.

24 Claims, 3 Drawing Sheets

FIG. 4
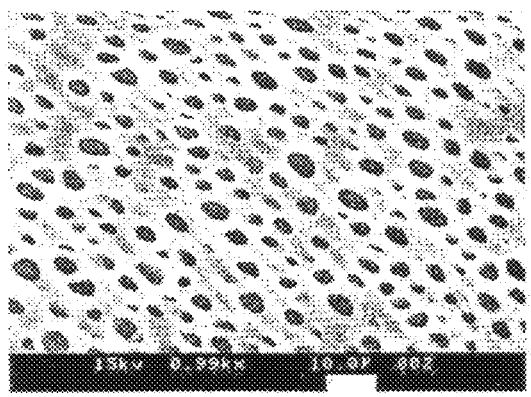
Example 1
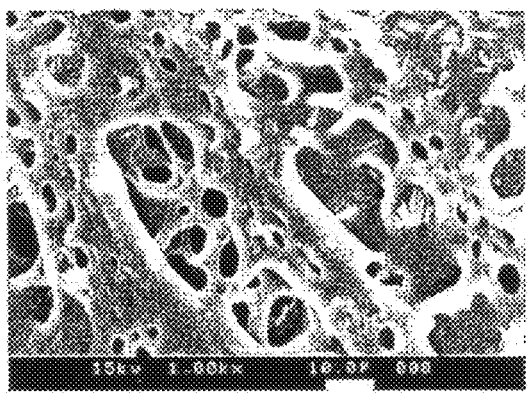
Example 2
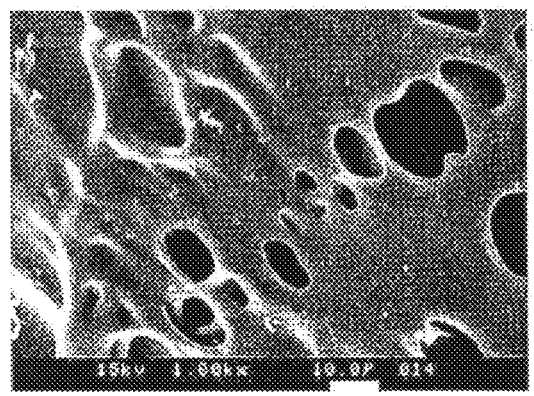
Example 3
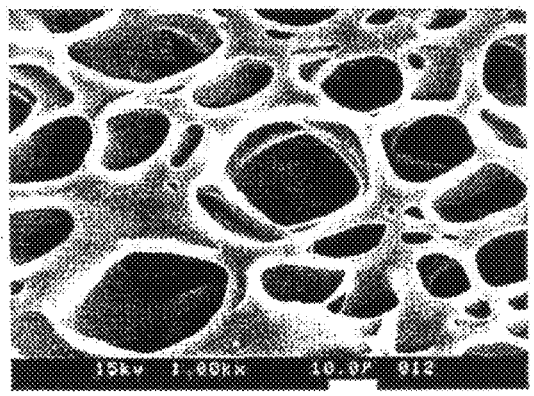
Example 4 ary application. So, in order to improve the problems,
PHOSPHAZENE HYDROGELS WITH CHEMICAL CORSS-LINK, PREPARATION METHOD THEREOF AND USE THEREOF

CROSS-REFERENCE TO RELATED APPLICATION

This application claims priorities to and the benefits of Korean Patent Application No. 10-2007-0058460, filed in Korean Intellectual Property Office on Jun. 14, 2007 and Korean Patent Application No. 10-2008-0040662, filed in Korean Intellectual Property Office on Apr. 30, 2008, the entire contents of which are incorporated herein by reference.

BACKGROUND OF THE INVENTION (a) Field of the Invention

A phosphazene-based polymer hydrogel with chemical cross-linkings formed by radiating ultraviolet (UV) and/or mixing the polymer with a cross-linking agent and/or an enzyme, a method of preparing the same, and a use thereof are provided.

(b) Description of the Related Art

A polymer hydrogel with a chemical cross-linking has a cross-linking formed by being polymerized due to the ultraviolet (UV) irradiation in a polymer; or a chemical cross-linking formed by a Michael-addition-type reaction between thiol and acrylate, acrylamide, or vinyl sulfone groups or an enzyme, to form a network structure, so that the polymer aqueous solution turns to a gel. When a polyethylene glycol-based hydrogel, which is a representative polymer hydrogel with a chemical cross-link, was used for delivering a protein drug, the protein drug was slowly released for 12 days (J. Controlled Release 76, 11 (2001)). However, on preparing the polymer hydrogel with a cross-link, it is hard to apply as a drug or physiological material carrier, because it is not easy to control gelation behavior and the physical property of gel; and a polymer hydrogel with a chemical cross-linking requires a long time to form a gel (Biomaterials 24, 11 (2003), Biomaterials 26, 4495 (2005)).

In a temperature-sensitive polymer hydrogel, the polymer aqueous solution maintains a liquid state at a low temperature, but it turns to a gel upon increasing temperature. Such sol-gel behavior may be observed in a reverse way. The temperature-sensitive polymer hydrogel is highly evaluated as a material for delivering an implant drug because it is easy for the polymer aqueous solution to be mixed with a pharmaceutical drug; it forms a three-dimensional gel at a body temperature by simply implanting to the required area without performing a surgery; and it can slowly release a drug (Nature, 388, 860 (1997), U.S. Pat. No. 6,201,072).

The present inventors have already reported that the phosphazene-based polymers obtained by substituting dichloro phosphazene linear polymer with amino acid ester and methoxy polyethylene glycol show temperature sensitive polymer characteristics in which it is an aqueous solution state under a certain temperature, but it turns to a three-dimensional gel above the certain temperature; these temperature-sensitive phosphazene-based polymers are slowly hydrolyzed in an aqueous solution (Macromolecules 32, 2188 (1999), Macromolecules 32, 7820 (1999), Macromolecules 35, 3876 (2002), Korean Patent Nos. 259,367, and 315,630, U.S. Pat. No. 6,319,984).

However, the temperature-sensitive polymer hydrogel has insufficient gel solidity, so it has limits to apply to a hydrophilic drug carrier. The polymer hydrogel being capable of chemical cross-linking by the cross-linking agent and/or enzyme has a limit to apply as an injectable carrier for physiological active material. So, in order to improve the problems, it is required to develop a biodegradable temperature-sensitive phosphazene polymer with a chemical cross-linking which is capable of showing a sol-gel behavior depending upon the temperature change to apply as an injectable carrier for physiological active material or drug; simultaneously, which has a sufficient hydrogel solidity and controls the pore size, so as to apply to a carrier for a physiological active material and a dental material such as an implant material, a tissue material such as an artificial cartilage and so on.

BRIEF DESCRIPTION OF THE DRAWINGS

FIG. 4 shows the change in pore sizes of the phosphazene-based polymer hydrogel having cross-linkings in accordance with a degree of cross-linking.

SUMMARY OF THE INVENTION

Figure 1:
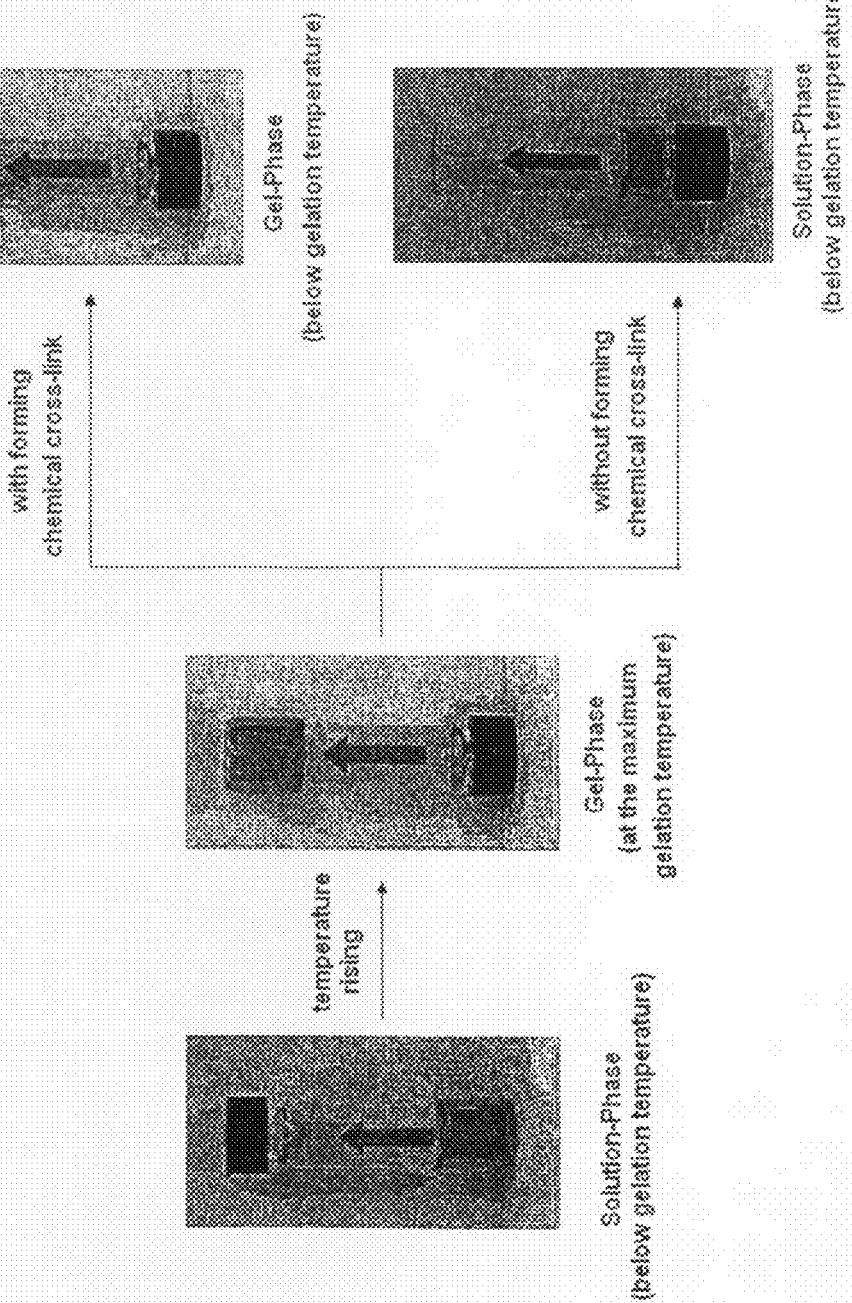
FIG. 1 is a photograph showing a sol-gel transition behavior of the temperature-sensitive phosphazene-based polymer that is capable of forming cross-linkings according to an embodiment of the present invention.

An embodiment of the present invention provides a phosphazene-based polymer that has a specific structure and is capable of forming chemical cross-linkings by radiating ultraviolet (UV) and/or mixing that polymer with a cross-linking agent and/or an enzyme and a method of preparing the same.

Another embodiment of the present invention provides a hydrogel with an excellent solidity including the phosphazene-based polymer that is capable of forming chemical cross-linkings at a predetermined concentration, thereby showing a sol-gel transition behavior by chemical cross-linkings when it is subjected to ultraviolet (UV) radiation and/or mixed with a cross-linking agent and/or an enzyme.

DETAILED DESCRIPTION OF THE PREFERRED EMBODIMENTS

A phosphazene-based polymer hydrogel with chemical cross-linkings by radiating ultraviolet (UV) and/or mixing the phosphazene-based polymer with a cross-linking agent and/or an enzyme and, a method of preparing the same, and a use thereof are provided.

The phosphazene-based polymer that is capable of forming cross-linkings not only shows a sol-gel behavior by the chemical cross-links, but also has a temperature sensitivity that shows a sol-gel transition behavior depending on the temperature change. Thus, the phosphazene-based polymer can readily form a gel by temperature change, and thereafter, it can forms a gel phase having increased solidity by a chemical cross-linking formed by the secondary ultraviolet irradiation and/or a chemical cross-linking formed by mixing with a cross-linking agent and/or an enzyme. Due to such properties, the polymer can be applied to the various applications such as a carrier for a physiological active material and a dental material such as an implant material, a tissue material such as an artificial cartilage and so on. In the other words, the conventional temperature sensitive polymer has drawbacks of a rough network between polymers; a weak hardness, early excessive release of the supported drug, but the phosphazene polymer according to the present invention is gelated by the temperature, and then forms a denser network between polymers due to the chemical cross-link. As a result, the present invention provides merits of the early release control and the steady release of the drug, and the polymer hardness is increased to be utilized to the various applications such as a dental material such as an implant material, a tissue material such as an artificial cartilage and so on. Furthermore, since it is possible to easily control the pore size of hydrogel with chemical cross-link, the supporting capacity of the hydrophilic drug is excellent enough to steadily release a drug, so that it is useful for a carrier material for a physiological active material.

An embodiment of the present invention provides a phosphazene-based polymer having chemical cross-linkings formed by irradiating ultraviolet (UV) and/or mixing a cross-linking agent and/or an enzyme, and showing a sol-gel behavior depending on the temperature. The phosphazene-based polymer may be presented by the following Chemical Formula 1:

based compound, a thiol-based compound, a cysteine-based compound, a cysteamine-based compound, mercaptic acid-based compound, allyl pyrimidine-based compound and, and the compounds including a thiol- or vinyl-group protected by a protecting group, or selected from the group consisting of a tyramine-based compound, a tyrosine-based compound, and a phenol-based compound.

The protecting group of the thiol-group may be selected from an alkyl, benzyl (e.g., p-methoxybenzyl, o- or p-hydroxy or acetoxybenzyl, p-nitrobenzyl, 2,4,6-trimethylbenzyl, 2,4,6-trimethoxybenzyl, 4-pycoryl, 2-quinolinyl methyl, 2-pycoryl N-oxydo, 9-anthryl methyl, 9-fluorenyl methyl, xanthenyl, p-ferrocenyl methyl), diphenylmethyl, triphenylmethyl thioether (e.g., diphenylmethyl, bis(4-methoxyphenyl)methyl, 5-dibenzosurberyl, triphenylmethyl, diphenyl-4-pyridylmethyl, phenyl, 2,3-dinitrophenyl, t-butyl, 1-adamantyl), a substituted methyl derivative (e.g., methoxymethyl, isobutoxymethyl, benzyloxymethyl, 2-tetrahydropyranyl, benzylthiomethyl, phenylthiomethyl, thiazolidine, acetamidomethyl, trimethylacetamidomethyl, benzamidomethyl, rimethylacetamidomethyl, allyloxycarbonylamidomethyl, phenylacetamidomethyl, phthalimidomethyl, acetyl, carboxyl, cyanomethyl), an ethyl derivative (e.g., 2-nitro-1-phenyl)ethyl, 2-(2,4-dinitrophenyl)ethyl, (Chemical Formula 1)

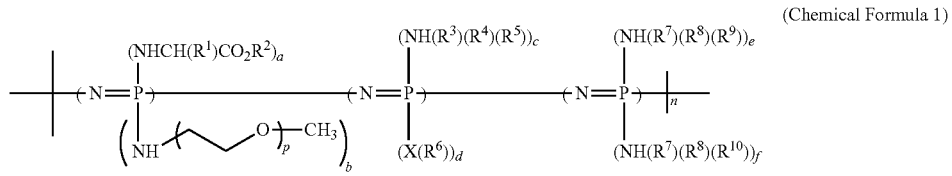

wherein, in the above formula, p represents a number of an ethyleneglycol repeating unit, and ranges from 7 to 50, $NHCH(R^1)CO_2R^2$ is an hydrophobic amino acid ester, where $R^1$ is selected from the group consisting of H, $CH_3$, $CH_2SH$, $CH(CH_3)_2$, $CH_2CH(CH_3)_2$, $CH(CH_3)C_2H_5$, $CH_2CH_2SCH_3$, $CH_2C_6H_5$, $CH_2C_6H_4OH$, and $CH_2C_2NH_2C_6H_4$, and $R^2$ is selected from the group consisting of $CH_3$, $C_2H_5$, $C_3H_7$, $C_4H_9$, $CH_2C_6H_5$, and $CH_2CHCH_2$, $NH(R^3)(R^4)(R^5)$ is an amino acid, a peptide, or a depsipeptide ester, where $R^3$ is CH(W), $R^4$ is selected from the group consisting of $CO_2$, $CONHCH(X)CO_2CO_2$, $CH_2CO_2$, and $CO_2CH(CH_3)CO_2$, and $R^5$ is selected from the group consisting of H, $CH_3$, and $C_2H_5$, where W and X are independently selected from the group consisting of H, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2NH_2C_6H_4$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4H_8NH_2$, $C_3H_6NHC(=NH)NH_2$, $CH_2C_3N_2H_3$, and $CH_3SH$, $XR^6$ is a substituent including a thiol- or vinyl-group being capable of cross-linking by ultraviolet (UV) radiation and/or a cross-linking agent, or a substituent including a tyrosine-, tyramine- or phenol-derivative being capable of cross-linking by enzyme, X is N or O, and $R^6$ is a compound including a thiol- or vinyl-group, a compound including a thiol- or vinyl-group protected with a protecting group, or a compound includes a tyrosine-, tyramine- or phenol-derivative, and is selected from the group consisting of an acrylate-based compound, a methacrylate-based compound, an acrylamide-based compound, a vinyl sulfone- 2-(4'-pyridyl)ethyl, 2-cyanoethyl, 2-(trimethylsilyl)ethyl, 2,2-bis(carboethoxy)ethyl, (1-m-nitrophenyl-2-benzoypethyl, 2-phenylsulfonylethyl, 1-(4-methylphenylsulfonyl)-2-methylprop-2-yl), thioester (e.g., acetyl, benzoyl, trifluoroacetyl, N-[[(p-biphenylyl)isopropoxy]carbonyl]-N-methyl-γaminothiobutyrate), thiocarbonate derivative 2,2,2-trichloroethoxycarbonyl, t-butoxycarbonyl, benzyloxycarbonyl, p-methoxybenzyloxycarbonyl), a thiocarbamate derivative (e.g., N-ethyl, N-methoxymethyl a miscellaneous derivative, an asymmetric disulfide (e.g., ethyl, t-butyl, a substituted S-phenyl disulfide), sulphenyl derivative (e.g., sulfonate, a sulphenyl thiocarbonate, a 3-nitro-2-pyridinesulphenyl sulfide, S-[tricarbonyl[1,2,3,4,5-η]-2,4-cyclohexadien-1-yl]-iron (1+), oxathiolone, and the protecting group of vinyl may be O-nitrophenyl selenoethyl, $NH(R^7)(R^8)(R^9)$ is a substituent including a functional group, where, $R^7$ is CH(Y), $R^8$ is selected from the group consisting of $CH_2$, $C_2H_4$, $C_3H_6$, $C_4H_8$, $CH_2C_6H_4$, $CH_2CO_2$, $C_2H_4CO_2$, O, CONHCH(Z)O, CONHCH(Z)CONHCH(M) O, CONHCH(Z)CONHCH(N)CONHCH(L)O, CO, $CO_2$, S, CONHCH(Z)S, CONHCH(Z)CONHCH(M)S, CONHCH (Z)CONHCH(M)CONHCH(L)S, N, CONHCH(Z)N, CONHCH(Z)CONHCH(M)N, CONHCH(Z)CONHCH(M) CONHCH(L)N, CON, COCHNH(Z)CON, COCHNH(Z) CONHCH(M)CON, COCHNH(Z)CONHCH(M)CONHCH (L)CON, CONHCH(Z)CO, COCHNH(Z)C ONHCH(M) CO, COCHNH(Z)CONHCH(M)C ONHCH(L)CO, CONHCH(Z)$CO_2$, CONHCH(Z)CONHCH(M)$CO_2$, COCHNH(Z)CONHCH(M)CONHCH(L)$CO_2$, [OCH(CH$_3$) CO]$_q$, (OCH$_2$CO)$_q$, [(OCH(CH$_3$)CO)$_q$, [OCO(CH$_2$)$_8$CO]$_q$, [OCOC$_6$H$_5$O(CH$_2$)$_3$OC$_6$H$_5$CO]$_q$, and [OCOC$_6$H$_5$O(CH$_2$)$_6$OC$_6$H$_5$CO]$_q$, and $R^9$ is selected from the group consisting of OH, SH, H, $NH_2$, $CH_3$, $C_2H_5$, $C_3H_7$, $C_4H_9$, $CH_2C_6H_5$, $CH_2CHCH_2$, $NHCH(SH)CO_2H$, $NH(CH_2)_qSH$, $NH(CH_2CH_2NH)_qH$, $[NHCH(C_4H_8NH_2)CO]_qOH$, $[NHCH[(CH_2)_3C(=NH)(NH_2)]CO]_qOH$, folic acid, hyaluronic acid, polyhistidine, cyclodextrin, heparin, chitosan, protamine, and a general protecting group of a functional group, where Y, Z, M, and L are independently selected from the group consisting of H, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2H_2C_6H_4$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4H_8NH_2$, $C_3H_6NHC(=NH)NH_2$, $CH_2C_3N_2H_3$, and $CH_2SH$, and q represents a number of a repeating unit and ranges from 1 to 18000, $NH(R^7)(R^8)(R^{10})$ is a substitutent including a thiol, a vinyl, or a tyrosine, tyramine or phenol derivative forming a cross-linking by ultraviolet (UV) radiation and/or a cross-linking agent and/or an enzyme, and $R^7$ and $R^8$ are the same as in defined in the substitutent $NH(R^7)(R^8)(R^9)$, $R^{10}$ is a compound being capable of cross-linking by ultraviolet (UV) radiation and/or a cross-linking agent and/or an enzyme, and selected from the group consisting of substitutent defined as in $R^6$, and is the same as or different from $R^6$, a, b, c, d, e, and f represent each content of substitutents, a and b range from 0.01 to 1.9, b, c, d, e, and f range from 0 to 1.9, d and f are not simultaneously zero, and a+b+c+d+e+f=2.0, and n represents a polymerization degree of polyphosphazene and ranges 5 to 100000.

The folic acid, hyaluronic acid, polyhistidine, cyclodextrin, heparin, chitosan, and protamine defined in $R^9$ is not limited in terms of a molecular weight, but preferably has a molecular weight ranging 500 to 100,000.

The general protecting group of a functional group of the $R^9$ may be generally known protecting groups, and for example, may be selected from the followings.

| Functional group | Protecting group (R' = R⁸) |
|---|---|
| Carboxyl group (RCOOR') | Fluorenylmethyl ester, Methoxymethyl ester ($CH_2OCH_3$), Methylthiomethyl ester ($CH_2SCH_3$), Tetrahydrofuranyl ester, Methoxyethoxymethyl ester ($CH_2OCH_2CH_2OCH_3$), 2-(trimethylsilyl)ethoxymethyl ester ($CH_2OCH_2CH_2Si(CH_3)_3$), Benzyloxymethyl ester ($CH_2OCH_2C_6H_5$), Pivaloyloxymethyl ester ($CH_2O_2CC(CH_3)_3$), Phenylacetoxymethyl ester ($CH_2O_2CCH_2Ph$), Triisopropylsilylmethyl ester ($CH_2Si$-$i$-$Pr_3$), Cyanomethyl ester ($CH_2CN$), Acetol ester ($CH_2COCH_3$), Phenacyl ester ($CH_2COC_6H_5$), p-Bromophenacyl ester ($CH_2COC_6H_4$-p-Br), α-Methylphenacyl ester ($CH(CH_3)COC_6H_5$). p-Methoxyphenacyl ester ($CH_2COC_6H_4$-p-$OCH_3$), Desyl ester, Carboxamidomethyl ester ($CH_2CONH_2$), p-Azobenzenecarboxamidomethyl ester ($CH_2(O)CNHC_6H_4N=NC_6H_5$), N-Phthalimidomethyl ester, 2,2,2-Trichloroethyl ester ($CH_2CCl_3$), 2-Haloethyl ester ($CH_2CH_2X$, X = I, Br, Cl), ω-Chloroalkyl ester (($CH_2)_nCl$, n = 4, 5), 2-(trimethylsilyl)ethyl ester ($CH_2CH_2Si(CH_3)_3$), 2-Methylthioethyl ester ($CH_2CH_2SCH_3$), 1,3-Dithianyl-2-methyl ester, 2-(p-Nitrophenylsulfenyl)ethyl ester ($CH_2CH_2SC_6H_4$-p-$NO_2$), 2-(p-Toluenesulfonyl)ethyl ester ($CH_2CH_2SO_2C_6H_4$-p-$CH_3$), 2-(2'-Pyridyl)ethyl ester ($CH_2CH_2$-2-$C_5H_4N$), 2-(p-Methoxyphenyl)ethyl ester ($CH_2CH_2C_6H_4O$-p-$CH_3$), 2-(diphenylphosphino)ethyl ester ($CH_2CH_2P(C_6H_5)_2$), 1-Methyl-1-phenylethyl ester ($C(CH_3)_2C_6H_5$), 2-(4-Acetyl-2-nitrophenyl)ethyl ester ($CH_2CH_2CHN$), t-Butyl ester ($C(CH_3)_3$), 3-Methyl-3-pentyl ester ($CCH_3(C_2H_4)_2$), Dicyclopropylmethyl ester, 2,4-Dimethyl-3-pentyl ester ($CH(i$-$Pr)_2$), Cyclopentyl ester (c-$C_5H_9$), Cyclohexyl ester (c-$C_6H_{11}$), Allyl ester ($CH_2CH=CH_2$), Methallyl ester ($CH_2(CH_3)C=CH_2$), 2-Methylbut-3-en-2-yl ester ($C(CH_3)_2CH=CH_2$), 3-Methylbut-2-enyl ester ($CH_2CH=C(CH_3)_2$), 3-Buten-1-yl ester ($CH_2CH_2CH=CH_2$), 4-(Trimethylsilyl)-2-buten-1-yl ester ($CH_2CH=CHCH_2Si(CH_3)_3$), Cinnamyl ester ($CH_2CH=CHC_6H_5$), α-Methylcinnamyl ester ($CH(CH_3)CH=CHC_6H_5$), Prop-2-ynyl ester ($CH_2C=CH$), Phenyl ester ($C_6H_5$), 2,6-Dimethylphenyl ester, 2,6-Diisopropylphenyl ester, 2,6-Di-t-butyl-4-methylphenyl ester, 2,6-Di-t-Butyl-4-methoxyphenyl ester, p-(Methylthio)phenyl ester ($C_6H_4$-p-$SCH_3$), Pentafluorophenyl ester ($C_6F_5$), Benzyl ester ($CH_2C_6H_5$), Triphenylmethyl ester ($C(C_6H_5)_3$), Diphenylmethyl ester ($CH(C_6H_5)_2$) Bis(o-nitrophenyl)methyl ester ($CH(C_6H_4$-o-$NO_2)_2$), 9-Anthrylmethyl ester ($CH_2$-9-Anthryl), 2-(9,10-Dioxo)anthrylmethyl) ester, 5-dibenzosuberyl ester, 1-Pyrenylmethyl ester, 2-(trifluoroaceticmthyl)-6-chromonylmethyl ester, 2,4,6-Trimethylbenzyl ester ($CH_2C_6H_2$-2,4,6-$(CH_3)_3$), p-Bromobenzyl ester ($CH_2C_6H_4$-p-Br), o-Nitrobenzyl ester ($CH_2C_6H_4$-o-$NO_2$), p-Nitrobenzyl ester ($CH_2C_6H_4$-p-$NO_2$), p-Methoxybenzyl ester ($CH_2C_6H_4$-p-$OCH_3$), 2,6-Dimethoxybenzyl ester ($CH_2C_6H_3$-2,6-$(OCH_3)_2$), 4-(Methylsulfinyl)benzyl ester ($CH_2C_6H_4(O)S$-4-$CH_3$), 4-Sulfobenzyl ester ($CH_2C_6H_4SO_3^-Na^+$), 4-Azidomethoxybenzyl ester ($CH_2C_6H_4OCH_2N_3$), 4-{N-[1-(4,4-Dimethyl-2,6-dioxocyclohexylidene)-3-methlbutyl]amino}benzyl ester, Piperonyl ester, 4-Picolyl ester ($CH_2$-4-pyridyl), p-P-Benzayl ester ($CH_2C_6H_4$-p-P), Trimethylsilyl ester ($Si(CH_3)_3$), Triethylsilyl ester ($Si(C_2H_5)_3$), t-Butyldimethylsilyl ester ($Si(CH_3)_2C(CH_3)$, i-Propyldimethylsilyl ester ($Si(CH_3)_2CH(CH_3)_2$), Phenyldimethylsilyl ester ($Si(CH3)_2C_6H_5$), Di-t-butylmethylsilyl ester ($SiCH_3(t$-$Bu)_2$), Triisopropylsilyl ester |
| Thiol group (RSR') | S-Alkyl thioether ($C_nH_{2n+1}$), S-Benzyl thioether ($CH_2Ph$), S-p-Methoxylbenzyl thioether ($CH_2C6H4$-p-$OCH_3$), S-o- or p-Hydroxy-or-Acetoxybenzyl thioether ($CH_2C6H4$-o-(or p-)-OR', R' = H or Ac), S-p-Nitrobenzyl thioether ($CH_2C_6H_4$-p-$NO_2$), S-2,4,6-Trimethylbenzyl thioether ($CH_2C_6H_2$-2,4,6-$Me_3$), S-2,4,6-Trimethoxybenzyl thioether ($CH_2C_6H_2$-2,4,6-$(OMe)_3$), S-4-Picolyl thioether ($CH_2$-4-pyridyl), S-2-Quinolinylmethyl thioether, S-2-Picolyl N-Oxide thioether ($CH_2$-2-pyridyl N-Oxide), S-9-Anthrylmethyl thioether ($CH_2$-9-anthtyl), S-9-Fluorenylmethyl thioether, S-Xanthenyl thioether, S-Ferrocenylmethyl thioether, S-Diphenylmethyl thioether ($CH(C_6H_5)_2$), S-Bis(4-methoxyphenyl)methyl thioether ($CH(C_6H_4$-4-$OCH_3)_2$), S-Bis(4-methoxyphenyl)phenylmethyl thioether, S-5-Dibenzosuberyl thioether, S-Triphenylmethyl thioether ($C(C_6H_5)_3$), S-Diphenyl-4-pyridylmethyl thioether ($C(C_6H_5)_2$-4-pyridyl), S-Phenyl thioether ($C_6H_5$), S-2,4-Dinitrophenyl thioether ($C_6H_3$-2,4-$(NO_2)_2$), S-t-Butyl thioether ($C(CH_3)_3$), S-1-Adamantyl thioether, S-Methoxymethyl monothioacetal ($CH_2OCH_3$), S-Isobutoxymethyl monothioacetal ($CH_2OCH_2CH(CH_3)_2$), S-Benzyloxymethyl monothioacetal ($CH_2OBn$), S-2-Tetrahydropyranyl monothioacetal, S-Benzylthiomethyl dithioacetal |

| Functional group | Protecting group (R' = R$^8$) |
|---|---|
| | (CH$_2$SCH$_2$C$_6$H$_5$), S-Phenylthiomethyl dithioacetal (CH$_2$SC$_6$H$_5$), S-Acetamidomethyl thioacetal (CH$_2$NHCOCH$_3$), S-Trimethylacetamidomethyl thioacetal (CH$_2$NHCOC(CH$_3$)$_3$), S-Benzamidomethyl (thioacetalCH$_2$NHCOC$_6$H$_5$), S-Allyloxycarbonylaminomethyl thioacetal (CH$_2$NH(O)COCH$_2$CH═CH$_2$), S-Phenylacetamidomethyl thioacetal (CH$_2$NH(O)CCH$_2$C$_6$H$_5$), S-Phthalimidomethyl thioacetal, S-Acetyl, S-Carboxy, and S-Cyanomethyl thioether (CH$_2$X, X = —COCH$_3$, —CO$_2$H, —CN), S-(2-Nitro-1-phenyl)ethyl thioether (CH(C$_6$H$_5$)CH$_2$NO$_2$), S-2-(2,4-Dinitrophenyl)ethyl thioether, S-2-(4'-Pyridyl)ethyl thioether (CH$_2$CH$_2$NC$_4$H$_4$), S-2-Cyanoethyl thioether (CH$_2$CH$_2$CN), S-2-(Trimethylsilyl)ethyl thioether (CH$_2$CH$_2$TMS), S-2,2-Bis(carboethoxy)ethyl thioether (CH$_2$CH(COOC$_2$H$_5$)$_2$), S-(1-m-Nitrophenyl-2-benzoyl)ethyl thioether (CH(C$_6$H$_4$-m-NO$_2$)CH$_2$COC$_6$H$_5$), S-2-phenylsulfonylethyl thioether (CH$_2$CH$_2$SO$_2$Ph), S-1-(4-Methylphenylsulfonyl)-2-methylprop-2-yl thioether (C(CH$_3$)$_2$CH$_2$SO$_2$C$_6$H$_4$-4-CH$_3$), Triisopropylsilyl thioether, S-Acetyl derivatives (COCH$_3$), S-Benzoyl derivatives (COC$_6$H$_5$), S-Trifluoroaceticacetyl derivatives(COCF$_3$), S-2,2,2-Trichloroethoxycarbonyl derivatives (COOCH$_2$CCl$_3$), S-t-Butoxycarbonyl derivatives (COOC(CH$_3$)$_3$), S-Benzyloxycarbonyl derivatives (COOCH$_2$C$_6$H$_5$), S-p-Methoxybenzyloxycarbonyl derivatives (COOCH$_2$C$_6$H$_4$-p-OCH$_3$), S-(N-Ethylcarbamate)(CONHC$_2$H$_5$), S-(N-Methoxymethylcarbamate) (CONHCH$_2$OCH$_3$), S-Ethyl disulfide (SC$_2$H$_5$), S-t-Butyl disulfide (SC(CH$_3$)$_3$) |
| Hydroxy group (ROR') | Methyl ether (CH$_3$), Methoxymethyl ether (CH$_2$OCH$_3$), Methylthiomethyl ether (CH$_2$SCH$_3$), (Phenyldimethylsilyl)methoxymethyl ether (CH$_2$OCH$_2$Si(CH$_3$)$_2$C$_6$H$_5$), Benzyloxymethyl ether (CH$_2$OCH$_2$Ph), p-Methoxybenzyloxymethyl ether (CH$_2$OCH$_2$C$_6$H$_4$O-p-Me), p-Nitrobenzyloxymethyl ether (CH$_2$OCH$_2$C$_6$H$_4$-4-NO$_2$), o-Nitrobenzyloxymethyl ether (CH$_2$OCH$_2$C$_6$H$_4$-2-NO$_2$), (4-Methoxyphenoxy)methyl ether (CH$_2$OC$_6$H$_4$-4-OCH$_3$), Guaiacolmethyl ether (CH$_2$OC$_6$H$_4$-2-OMe), t-Butoxymethyl ether (CH$_2$O-t-Bu), 4-Pentenyloxymethyl ether (CH$_2$OCH$_2$CH$_2$CH$_2$CH═CH$_2$), Siloxymethyl ether (CH$_2$OSiR'R", R' = t-Bu, R" = Me; R' = Thexyl, R" = Me; R' = t-Bu, R" = Ph), 2-Methoxyethoxymethyl ether (CH$_2$OCH$_2$CH$_2$OCH$_3$), 2,2,2-Trichloroethoxymethyl ether (CH$_2$OCH$_2$CCl$_3$), Bis(2-chloroethoxy)methyl ether (CH(OCH$_2$CH$_2$Cl)$_2$), 2-(Trimethylsilyl)ethoxymethyl ether (CH$_2$OCH$_2$CH$_2$SiMe$_3$), Methoxymethyl ether, Tetrahydropyranyl ether, 3-Bromotetrahydropyranyl ether, Tetrahydrothiopyranyl ether, 1-Methoxycyclohexyl ether, 4-Methoxytetrahydropyranyl ether, 4-Methoxytetrahydrothiopyranyl ether, 1-[(2-Chloro-4-methyl)phenyl]-4-methoxypiperidin-4-yl ether, 1-(2-Fluorophenyl)-4-methoxypiperidin-4-yl ether, 1,4-Dioxan-2-yl ether, Tetrahydrofuranyl ether, Tetrahydrothiofuranyl ether, 2,3,3a,4,5,6,7,7a-octahydro-7,8,8-trimethyl-4,7-methanobenzofuran-2-yl ether, 1-Ethoxyethyl ether (CH(OC$_2$H$_5$)CH$_3$), 1-(2-Chloroethoxy)ethyl ether (CH(CH$_3$)OCH$_2$CH$_2$Cl), 1-[2-(Trimethylsilyl)ethoxy]ethyl ether, 1-Methyl-1-methoxyethyl ether (C(OCH$_3$)(CH$_3$)$_2$), 1-Methyl-1-benzyloxyethyl ether (C(OBn)(CH$_3$)$_2$), 1-Methyl-1-benzyloxy-2-fluoroethyl ether (C(OBn)(CH$_2$F)(CH$_3$)), 1-Methyl-1-phenoxyethyl ether (C(OPh)(CH$_3$)$_2$), 2,2,2-trichloroethyl ether (CH$_2$CCl$_3$), 1,1-Dianisyl-2,2,2-trichloroethyl ether, 1,1,1,3,3,3-Hexafluoro-2-phenylisopropyl ether (C(CHF$_3$)$_2$Ph), 2-Trimethylsilylethyl ether (CH$_2$SiMe$_3$), 2-(Benzylthio)ethyl ether (CH$_2$CH$_2$SBn), 2-(Phenylselenyl)ethyl ether (CH$_2$CH$_2$SePh), t-Butyl ether, Allyl ether (CH$_2$CH═CH$_2$), Propargyl ether (CH$_2$C≡CH), p-Methoxyphenyl ether (C$_6$H$_4$O-p-Me), p-Nitrophenyl ether (C$_6$H$_4$-p-NO$_2$), 2,4-Dinitrophenyl ether (C$_6$H$_3$-2,4-(NO$_2$)$_2$), 2,3,5,6-Tetrafluoro-4-(trifluoroaceticmethyl)phenyl ether (C$_6$F$_4$CF$_3$), Benzyl ether (CH$_2$Ph), p-Methoxybenzyl ether (CH$_2$C$_6$H$_4$-p-OMe), 3,4-Dimethoxybenzyl ether (CH$_2$C$_6$H$_3$-3,4-(OMe)$_2$), o-Nitrobenzyl ether (CH$_2$C$_6$H$_4$-o-NO$_2$), p-Nitrobenzyl ether (CH$_2$C$_6$H$_4$-p-NO$_2$), p-Halobenzyl ether (CH$_2$C$_6$H$_4$-p-X, X = Br, Cl), 2,6-Dichlorobenzyl ether (CH$_2$C$_6$H$_3$-2,6-Cl$_2$), p-Cyanobenzyl ether (CH$_2$C$_6$H$_4$-p-CN), p-Phenylbenzyl ether (CH$_2$C$_6$H$_4$-p-C$_6$H$_5$), 2,6-Difluorobenzyl ether (CH$_2$C$_6$H$_3$F$_2$), p-Acylaminobenzyl ether (CH$_2$C$_6$H$_3$-p-NHCOR'), p-Azidobenzyl ether (CH$_2$C$_6$H$_4$-4-N$_3$), 4-Azido-3-chlorobenxyl ether (CH$_2$C$_6$H$_3$-3-Cl-4-N$_3$), 2-Trifluoroaceticmethylbenzyl ether (CH$_2$C$_6$H$_4$-2-CF$_3$), p-(Methylsulfinyl)benzyl ether (CH$_2$C$_6$H$_4$-p-(MeS(O)), 2- and 4-Picolyl ether(CH$_2$C$_5$H$_4$N), 3-Methyl-2-picolyl N-Oxido ether, 2-Quinolinylmethyl ether, 1-Pyrenylmethyl ether, Diphenylmethyl ether (CHPh$_2$), p,p'-Dinitrobenzhydryl ether (CH(C$_6$H$_4$-p-NO$_2$)$_2$), 5-Dibenzosuberyl ether, Triphenylmethyl ether, p-Methoxyphenyldiphenylmethyl ether (C(Ph)$_2$C$_6$H$_4$-p-OMe), Di(p-methoxyphenyl)phenylmethyl ether (CPh(p-MeOC$_6$H$_4$)$_2$), Tri(p-methoxyphenyl)methyl ether (C(p-MeOC$_6$H$_4$)$_3$), 4-(4'-Bromophenacyloxy)phenyldiphenylmethyl ether (C(Ph)$_2$C$_6$H$_4$-p-(OCH$_2$(O)CC$_6$H$_4$-p-Br), 4,4',4"-Tris(4,5-dichlorophthalimidophenyl)methyl ether, 4,4',4"-Tris(levulinoyloxyphenyl)methyl) ether, 4,4'4"-Tris(benzoyloxyphenyl)methyl) ether, 4,4'-Dimethoxy-3"-[N-(imidazolylmethyl)]trityl ether, 4,4'-Dimethoxy,3"-[N-(imidazolylethyl)carbamoyl)trityl ether, 1,1-Bis(4-methoxyphenyl)-1-pytenylmethyl ether, 4-(17-tetrabenzo[a,c,g,i]fluorenylmethyl)-4',4"-dimethoxytrityl ether, 9-Anthryl ether, 9-(9-Phenyl)xanthenyl ether, Tritylone ether, 1,3-Benzodithiolan-2-yl ether, Benziisothiazolyl-S,S-dioxido ether, Trimethylsilyl (e.g., Si(CH$_3$)$_3$) ether, Triethylsilyl (SiEt$_3$) ether, Triisopropylsilyl (Si(i-Pr)$_3$) ether, Dimethylisopropylsilyl (SiMe$_2$-i-Pr) ether, Diethylisopropylsilyl (SiEt$_2$-i-Pr) ether, Dimethylthesilyl ether ((CH$_3$)$_2$Si(CH$_3$)$_2$CCH(CH$_3$)$_2$), t-Butyldimethylsilyl (SiMe$_2$-t-Bu), t-Butyldiphenylsilyl ether (SiPh$_2$-t-Bu), Tribenxylsily ether (Si(CH$_2$C$_6$H$_5$)$_3$), Tri-p-xylylsilyl ether (Si(CH$_2$C$_6$H$_4$-p-CH$_3$)$_3$), Triphenylsilyl ether (SiPh$_3$), Diphenylmethylsily ether (SiMePh$_2$), Di-t-butylmethylsilyl ether (SiMe(t-Bu)$_2$), Tris(trimethylsilyl)silyl ether ([Si[Si(CH$_3$)$_3$]$_3$), (2-Hydroxystyryl)dimethylsilyl ether, (2-Hydroxystyryl)diisopropylsilyl ether, t-Butylmethoxyphenylsilyl ether (SiPh(OCH$_3$)-t-Bu), t-Butoxydiphenylsilyl ether (Si(t-OBu)Ph$_2$), Formate ester (CHO), Benzoylformate ester (COCOPh), Acetate ester (COCH$_3$), Chloroacetate ester (COCH$_2$Cl), Dichloroacetate ester (COCHCl$_2$), Trichloroacetate ester (COCCl$_3$), Trifluoroaceticacetate ester (COCF$_3$), Methoxyacetate ester (COCH$_2$OMe), Triphenylmethoxyacetate ester (COCH$_2$OCPh$_3$), Phenoxyaetate ester (COCH$_2$OPh), p-chlorophenoxyacetate ester (COCH$_2$OC$_6$H$_4$-p-Cl), phenylacetate ester (COCH$_2$Ph), p-P-Phenylacetate ester (COCH$_2$C$_6$H$_4$-p-P), Diphenylacetate ester (COCHPh$_2$), Nicotinate ester, 3- |

-continued

| Functional group | Protecting group (R' = R⁸) |
|---|---|
| | Phenylpropionate ester (COCH$_2$CH$_2$Ph), 4-Pentenoate ester (COCH$_2$CH$_2$CH=CH$_2$), 4-Oxopentanoate ester (COCH$_2$CH$_2$COCH$_3$), 4,4-(Ethylenedithio)pentanoate ester, 5-[3-Bis(4-methoxyphenyl)hydroxymethylphenoxy]levulinic acid ester, Pivaloate (COC(CH$_3$)$_3$) ester, Crotonate ester (COCH=CHCH$_3$), 4-Methoxycrotonate ester (COCH=CHCH$_2$OCH$_3$), Benzoate ester (COPh), p-Phenylbenzoate ester (COC$_6$H$_4$-p-C$_6$H$_5$), 2,4,6-Trimethylbenzoate ester (COC$_6$H$_2$-2,4,6-Me$_3$), Alkyl methyl carbonate (CO$_2$CH$_3$), Methoxymethyl carbonate (CO$_2$CH$_2$OCH$_3$), alkyl 9-fluorenylmethyl carbonate, Alkyl ethyl carbonate (CO$_2$Et), Alkyl 2,2,2-Trichloroethyl carbonate (CO$_2$CH$_2$CCl$_3$), 1,1-Dimethyl-2,2,2-trichloroethyl carbonate (CO$_2$C(CH$_3$)$_2$CCl$_3$), Alkyl 2-(trimethylsilyl)ethyl carbonate (CO$_2$CH$_2$CH$_2$SiMe$_3$), Alkyl 2-(phenylsulfonyl)ethyl caronate (CO$_2$CH$_2$CH$_2$SO$_2$Ph), Alkyl isobutyl carbonate (CO$_2$CH$_2$CH(CH$_3$)$_2$), Alkyl vinyl carbonate (CO$_2$CH=CH$_2$), Alkyl allyl carbonate (CO$_2$CH$_2$CH=CH$_2$), Alkyl p-nitrophenyl carbonate (CO$_2$C$_6$H$_4$-p-NO$_2$), Alkyl benzyl carbonate (CO$_2$Bn), Alkyl p-methoxybenzyl carbonate (CO$_2$CH$_2$C$_6$H$_4$-p-OMe), Alkyl 3,4-dimethoxybenzyl carbonate (CO$_2$CH$_2$C$_6$H$_3$-3,4-(OMe)$_2$), Alkyl o-nitrobenzyl carbonate (CO$_2$CH$_2$C$_6$H$_4$-o-NO$_2$), Alkyl p-nitrobenzyl carbonate (CO$_2$CH$_2$C$_6$H$_4$-p-NO$_2$), 2-Dansylethyl carbonate, 2-(4-Nitrophenyl)ethyl carbonate (CO$_2$CH$_2$CH$_2$C$_6$H$_4$-4-NO$_2$), 2-(2,4-dinitrophenyl)ethyl carbonate (CO$_2$CH$_2$CH$_2$C$_6$H$_3$-2,4-(NO$_2$)$_2$), 2-Cyano-1-phenylethyl carbonate (CO$_2$(C$_6$H$_5$)CHCH$_2$CN), Alkyl S-Benzyl thiocarbonate (COSCH$_2$Ph), Alkyl 4-ethoxy-1-naphthyl carbonate, Alkyl methyl dithiocarbonate (SCSCH$_3$), 2-iodobenzoate ester (COC$_6$H$_4$-2-I), 4-Azidobutyrate ester (CO(CH$_2$)$_3$N$_3$), 4-Nitro-4-methylpentanoate ester, o-(dibromomethyl)benzoate ester (COC$_6$H$_4$-o-(CHBr$_2$)), 2-Formylbenzenesulfonate ester, Alkyl 2-(methylthiomethoxy)ethyl carbonate (CO$_2$CH$_2$CH$_2$OCH$_2$SCH$_3$), 4-(Methylthiomethoxy)butyrate ester (CO(CH$_2$)$_3$OCH$_2$SCH$_3$), 2-(Methylthiomethoxymethyl)benzoate ester (COC$_6$H$_4$-2-(CH$_2$OCH$_2$SCH$_3$)), 2-(Chloroacetoxymethyl)benzioate ester, 2-[(2-chloroacetoxy)ethyl]benzoate ester, 2-[2-(Benzyloxy)ethyl]benzoate ester, 2-[2-(4-Methoxybenzyloxy)ethyl]benzoate ester, 2,6-Dichloro-4-methylphenoxyacetate ester, 2,6-Dichloro-4-(1,1,3,3-tetramethylbutyl)phenoxyacetate ester, 2,4-Bis(1,1-dimethylpropyl)phenoxyacetate ester, Chlorodiphenylacetate ester, Isobutyrate ester, Monosuccinoate ester, (E)-2-Methyl-2-Butenoate ester, o-(Methoxycarbonyl)benzoate ester, p-P-Benzoate ester, α-Naphthoate ester, Nitrate ester, Alkyl N,N,N',N'-tetramethylphosphorodiamidate, 2-Chlorobenzoate ester, 4-Bromobenzoate ester, 4-Nitrobenzoate ester, 3,5-Dimethoxybenzoin carbonate, A wild and woolly photolabile fluorescent ester, Alkyl N-phenylcarbamate, Borate ester, Dimethylphosphinothioyl ester ((S)P(CH$_3$)$_2$), Alkyl 2,4-dinitrophenylsulfenate (SC$_6$H$_3$-2,4-(NO$_2$)$_2$), Sulfate, Allylsulfonate (SOCH$_2$CH=CH$_2$), Methanesulfonate (SO$_2$Me), Benzylsulfonate (SO$_2$Bn), Tosylate (SO$_2$C$_6$H$_4$CH$_3$), 2-[(4-Nitrophenyl)ethyl]sulfonate (SO$_2$CH$_2$CH$_2$C$_6$H$_4$-4-NO$_2$) |
| Amino group (RNR') | Formamide (CHO), Acetamide (Ac), Chloroacetamide (COCH$_2$Cl), Trichloroacetamide (COCCl$_3$), Trifluoroaceticacetamide (COCF$_3$), Phenylacetamide (COCH$_2$C$_6$H$_5$), 3-Phenylpropanamide (COCH$_2$CH$_2$C$_6$H$_5$), Pent-4-enamide ((O)CH$_2$CH$_2$CH=CH$_2$), Picolinamide (CO-2-pyridyl), 3-Pyridylcarboxamide (CO-3-Pyridyl), N-Benzoylphenylalanyl derivatives (COCH(NHCOC$_6$H$_5$)CH$_2$C$_6$H$_5$), Benzamide (COC$_6$H$_5$), p-Phenybenzamide (COC$_6$H$_4$-p-C$_6$H$_5$) |
| Amide group (CORNR') | N-Allylamide (CH$_2$CH=CH$_2$), N-t-Butylamide (t-Bu), N-Dicyclopropylmethylamide (CH(C$_3$H$_5$)$_2$), N-Methoxymethylamide (CH$_2$OCH$_3$), N-Methylthiomethylamide (CH$_2$SCH$_3$), N-Benzyloxymethylamide (CH$_2$OCH$_2$C$_6$H$_5$), N-2,2,2-Trichloroethoxymethylamide (CH$_2$OCH$_2$CCl$_3$), N-t-Butyldimethylsiloxymethylamide (CH$_2$OSi(CH3)$_2$-y-C$_4$H$_9$), N-Pivaloyloxymethylamide (CH$_2$CO$_2$C(CH$_3$)$_3$), N-Cyanomethylamide (CH$_2$CHN), N-Pyrrolidinomethylamide, N-Methoxyamide (OMe), N-Benzyloxyamide (OCH$_2$C$_6$H$_5$), N-Methylthioamide (SMe), N-Triphenylmethylthioamide (SCPh$_3$), N-t-Butyldiethylsilylamide (Si(CH$_3$)$_2$-t-C$_4$H$_9$), N-Triisopropylsilylamide (Si(i-Pr)$_3$), N-4-Methoxyphenylamide (C$_6$H$_4$-4-OCH$_3$), N-4-(Methoxymethoxy)phenylamide (C$_6$H$_4$(OCH$_3$)$_2$), N-2-Methoxy-1-naphthylamide (C$_{10}$H$_6$-2-OCH$_3$), N-Benzylamide (CH$_2$C$_6$H$_5$), N-4-Methoxybenzylamide (CH$_2$C$_6$H$_4$-4-OCH$_3$), N-2,4-Dimethoxybenzylamide N-3,4-Dimethoxybenzylamide (CH$_2$C$_6$HH$_3$-2,4(3,4)-(OCH$_3$)$_2$), N-2-Acetoxy-4-methoxybenzylamide (CH$_2$C$_6$HH$_3$-4-OMe-2-Ac), N-o-nitrobenzylamide (CH$_2$C$_6$H$_4$-2-NO$_2$), N-Bis(4-methoxyphenyl)methylamide (CH(C$_6$H$_4$-4-OMe)$_2$), N-Bis(4-(methoxyphenyl)phenylmethylamide (CPh-(C$_6$H$_4$-4-OMe)$_2$), N-Bis(4-methylsulfinylphenyl)methylamide (CH(C$_6$H$_4$(O)S-4-Me)$_2$), N-Triphenylmethylamide (C(C$_6$H$_5$)$_3$), N-9-Phenylfluorenylamide, N-t-Butoxycarbonylamide (CO-t-OC$_4$H$_9$), N-benzyloxycarbonylamide, N-Methoxycarbonylamide (COOMe), N-Ethoxycarbonylamide (COOEt), N-p-Toluenesulfonylamide, N-Butenylamide (CH=CHCH$_3$), N-[(E)-2-(Methoxycarbonyl)vinyl]amide (CH=CCO$_2$Me), N-Diethoxymethylamide (CH(OEt)$_2$), N-(1-Methoxy-2,2-dimethylpropyl)amide, N-2-(4-Methylphenylsulfonyl)ethylamide (CH$_2$CH$_2$SO$_2$C$_6$H$_4$-4-CH$_3$) |

More preferably, in the definitions of $R^6$ and $R^{10}$, the acrylate-based compound may be selected from the group consisting of an acrylate; an acrylate including a C1 to C30 substituted or unsubstituted linear or branched alkyl substituted with at least one selected from the group consisting of a halogen, a C1 to C12 alkoxy, an acryloyloxy, and an amino acid (e.g., ethyl acrylate, ethoxyethyl acrylate, diethoxyethyl acrylate, propyl acrylate, hexyl acrylate, 3-chloro-2-propyl acrylate, 3-(acryloyloxy)-2-propyl acrylate, glycine ethyl acrylate, and so on); an acrylate including an amino acid group (e.g., glycidyl acrylate and so on); ethylene glycol acrylate; or a polyethyleneglycol acrylate including polyethyleneglycol of a molecular weight of 200 to 2,500, the methacrylate-based compound may be selected from the group consisting of methacrylate; methacrylate including a C1 to C30 substituted or unsubstituted linear or branched alkyl substituted with at least one selected from the group consisting of a halogen, a C1 to C12 alkoxy, an acryloyloxy, and an amino acid (e.g., ethyl methacrylate, ethoxyethyl methacrylate, diethoxyethyl methacrylate, butyl methacrylate, propylmethacrylate, hexyl acrylate, 3-chloro-2-propyl methacrylate, 3-(acryloyloxy)-2-propyl methacrylate, glycine ethyl methacrylate, and so on); methacrylate including an amino acid group (e.g., glycidyl methacrylate, and so on); ethyleneglycol methacrylate; and polyethyleneglycol methacrylate including polyethyleneglycol of a molecular weight of 200 to 2,500, the acrylamide-based compound may be selected from the group consisting of acryl amide; acryl amide including a C1 to C30 substituted or unsubstituted linear or branched alkyl substituted with at least one selected from the group consisting of a halogen, a C1 to C12 alkoxy, acryloyloxy, and an amino acid (e.g., ethyl acrylamide, ethoxyethyl acrylamide, diethoxyethyl acrylamide, butyl acrylamide, propyl acrylamide, hexyl acrylamide, 3-chloro-2-propyl acrylamide, 3-(acryloyloxy)-2-propyl acrylamide, N-isopropyl acrylamide, glycyl ethyl acrylamide, and so on); acryl amide including an amino acid group (e.g., glycidyl acrylamide, and so on); ethyleneglycol acrylamide; and polyethyleneglycol amide including polyethyleneglycol of a molecular weight of 200 to 2,500, the vinyl sulfone-based compound may be selected from the group consisting of vinyl sulfone, vinyl sulfone-ethyleneglycol, vinyl sulfone-polyethyleneglycol including polyethyleneglycol of a molecular weight of 200 to 2,500, vinyl sulfone-alkylate including a C1 to C30 alkyl, vinyl sulfone-amino acid (e.g., vinyl sulfone-cysteine, and so on), and vinyl sulfone-a peptide, the thiol-based compound may be selected from the group consisting of thiol-polyethylene glycol including polyethylene glycol of a molecular weight of 200 to 2,500, and thiol-alkylate including a C1 to C30 alkyl, the cysteine-based compound may be selected from the group consisting of cysteine, N-acetyl-cysteine, or N-acetyl-cysteine alkyl ester including including a C1 to C30 alkyl (e.g., N-acetyl-cysteine methyl ester, and N-acetyl-cysteine ethyl ester), the cysteamine-based compound may be cysteamine, or N-acetyl-cysteamine, the mercaptic acid-based compound may be 2-mercapto succinic acid, the allyl pyrimidine-based compound may be 1-allyl-2-amino-pyridinium, or 1-allyl-6-amino-3-ethyl-5-nitrosouracil, the tyramine-based compound may be tyramine, 3-methoxytyramine, and so on, the tyrosine-based compound may be tyrosine, or tyrosine methylester, or tyrosine ethylester, and the phenol-based compound is 2-amino-4-phenylphenol, 2-amino-4-teriaryamylphenol, 2-amino-4-tert-butylphenol, 8-amino-2-naphthol, 5-amino-1-naphthol, 4-amino-1-naphthol, 3-amino-2-naphthol, 1-amino-2-naphthol, 4-amino 2,5 dimethylphenol, 5-amino-2-methoxyphenol, 5-amino-2-methylphenol, 4-amino-3-methylphenol, 4-amino-2-methylphenol, 2-amino-5-methylphenol, 2-amino-4-methylphenol, 2-amino-3-methylphenol, 2,4-diaminophenol, 2,3-diaminophenol, 4-aminophenol, 3-aminophenol, 2-aminophenol, 4-amino-3-nitrophenol, 4-amino-2-nitrophenol, 2-amino-5-nitrophenol, 2-amino-4-nitrophenol, 2-amino-4fluorophenol, 4-amino-3-chlorophenol, 4-amino-2-chlorophenol, 3-amino-4-chlorophenol, 2-amino-5-chlorophenol, 2-amino-4-chlorophenol, 5-amino-2,4-dichlorophenol, 4-amino-3,6-dichlorophenol, 2-amino-4-chloro-6nitrophenol, 4-amino-2,6-dibromophenol, and so on.

In phosphazene-based polymer according to the present invention, a hydrophobic amino acid ester [NHCH($R^1$) $CO_2R^2$ in the above Formula 1] and a hydrophilic molecule, methoxy polyethylene glycol, having a molecular weight ranging 350 to 2500 are introduced into a dichlorophosphazene linear polymer in order for the polymer to show the temperature sensitive and biodegradation; furthermore, amino acid, peptide, or depsipeptide ester [NH($R^3$)($R^4$)($R^5$) in the above Formula 1] being capable of controlling the degradation speed of the polymer may be partially introduced thereto. The phosphazene-based polymer according to the present invention can have a functional group by directly introducing a substituent having a functional group such as hydroxyl group, amide group, amino group, thiol group, or carboxyl group at the side chain [NH($R^7$)($R^8$)($R^9$) in Chemical Formula 1] to the main chain of the polymer; or by introducing the main chain of the polymer with an amino acid ester or a peptide ester that the functional group is substituted with a protection group, then deprotecting or introducing a substitutent having hydroxyl group to the main chain of the polymer, and esterificating the same to change to a carboxyl group. Furthermore, it is possible to introduce a functional group to polyphosphazene by reacting lysine, arginine, cysteine, thiolan alkylamine, or polyethylene imine, polylysine, polyarginine or protamine having the various molecular weight with a polyphosphazene having carboxylic acid. The usable protection group may include any protection group available for commonly used for protecting each functional group (Protective groups in organic synthesis, Theodora W. Greene, Peter G. M. Wuts, Wiley-interscience, Third Edition), which can be easily selected by any one having ordinary skills in the art.

It is possible to control a temperature (gelation temperature) showing a sol-gel behavior of phosphazene polymer according to the present invention, a gel solidity, and/or a biodegradation speed by adjusting the kind of the hydrophobic amino acid ester, the kind of amino acid, a peptide, or depsipeptide ester capable of controlling a degradation speed, the kind of the substitutent having functional group, the chain length of the methoxypolyethylene glycol, the composition of all substitutents, the molecular weight of phosphazene-based polymer, polydispersity index, the concentration of phosphazene-based polymer solution and so on. For example, as the composition of hydrophobic amino acid is increased, the gelation temperature is decreased. As the concentration of phosphazene-based polymer solution is increased, the gelation temperature is decreased and the gel solidity is increased. As the chain length of methoxy polyethylene glycol is longer, the gel solidity is stronger and the galation temperature is higher. The phosphazene-based polymer including depsipeptide ester is biodegraded faster than that of phosphazene-based polymer having no depsipeptide ester. The phosphazene-based polymer including substitutent having a carboxylic acid functional group is biodegraded faster than that of phosphazene-based polymer including no substitutent having a carboxylic acid functional group.

The phosphazene-based polymer according to the present invention is introduced with a hydrophobic material and a hydrophilic material. The polymer may include a material for controlling the degradation speed selected from the group consisting of amino acid, peptide, and depsipeptide and/or one having a side chain of a functional group selected from the group consisting of hydroxyl, amide, amino, thiol, and carboxyl. The polymer according to the present invention has a sol-gel behavior at a temperature ranging from 5 to 70° C. and a molecular weight ranging from 4,000 to 400,000. According to another embodiment, the sol-gel behavior is performed at a temperature ranging from 20 to 45° C. The polymer is gelated at the body temperature by itself or by adding an additive and/or a physiological active material such as a supported drug. When a drug or a physiological active material such as a treatment cell is supported in the polymer or the composition for delivering a physiological active material including the hydrogel and injected to the body, it forms a three-dimensional gel due to the body temperature. Thereby, it is possible to suppress the early and excessive amount release of the physiological active material in the body, and it can control the release speed to release steadily and effectively.

On the other hand, the present invention provides a method of preparing the biodegradable phosphazene-based polymer having a structure represented by Chemical Formula 1 and being capable of chemical cross-linking by radiating the ultraviolet (UV) and/or by mixing a cross-linking agent and/or an enzyme and a phosphazene-based polymer. The preparation method of the present invention includes the following processes:

(1) polymerizing a phosphazene trimer of the Chemical Formula 2 through thermal polymerization, cationic polymerization of phosphoranimine, or other conventional polymerization method to obtain a dichlorophosphazene linear polymer of the Chemical Formula 3;

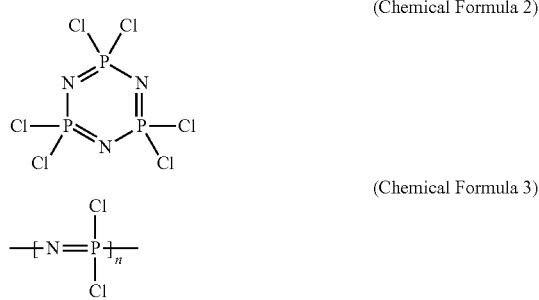

(Chemical Formula 2)

(Chemical Formula 3)

(where, n ranges from 1 to 100000)

(2) reacting the compound of the the Chemical Formula 3 obtained in step (1) with 0.01 to 1.9 equivalent of an amino acid ester or a salt thereof having the following Chemical Formula 4;

$NH_2CH(R^1)CO_2R^2$ (Chemical Formula 4)

(3) reacting the resulting product of the step (2) with 0 to 1.9 equivalent of amino acid, a peptide, a depsipeptide ester or salts thereof of Chemical Formula 5;

$NH_2(R^3)(R^4)(R^5)$ (Chemical Formula 5)

(4) reacting the resulting product of the step (3) with 0.01 to 1.9 equivalent of a substitutent being capable of cross-linking of the following Chemical Formula 6 or a salt thereof;

$NH_2(R^6)$ or $OH(R^6)$ (Chemical Formula 6)

(5) reacting the resulting product of the step (3) or (4) with 0.01 to 1.9 equivalent of a substitutent having a functional group of the Chemical Formula 6 or a salt thereof; and $NH_2(R^7)(R^8)(R^9)$ (Chemical Formula 8)

(6) reacting the resulting product of the step (4) or (5) with aminomethoxy polyethyleneglycol of the Chemical Formula 8 or a salt thereof.

$NH_2(CH_2CH_2O)_pCH_3$

The preparation method of the present invention may further include a step [step (6-1)] of subjecting the polymer obtained from the step (6) to the dehydrogenation reaction (when $R^9$ is $CH_2C_6H_5$), the deallylesterication reaction (when $R^9$ is $CH_2CHCH_2$), the deprotecting reaction, or the esterification reaction to let $R^9$ have a hydrogen (H) functional group or the various functional groups to provide a phosphazene polymer, when $R^9$ is selected from the group consisting of $CH_2C_6H_5$, $CH_2CHCH_2$, OH, and a protecting group in Chemical Formula 7.

In addition, the method may further include a step [step (6-2)] of reacting the product having carboxylic acid obtained from the step (6) or the product obtained from the dehydrogenation reaction, the deallylesterication reaction, or the esterification reaction of the step (6-1) with lysine, arginine, cysteine, thiolan alkylamine, or polyethyleneimine, polylysine, polyarginine, folic acid, hyaluronic acid, polyhistidine, cyclodextrin, heparin, chitosan or protamine having a various molecular weight such that $R^9$ has the various functional groups such as $NHCH(SH)CO_2H$, $NH(CH_2)_qSH$, $NH(CH_2CH_2NH)_rH$, $[NH(CH_2)_4CH(NH_2)CO]_rH$, $[NHC(=NH)(CH_2)_3CH(NH_2)CO]_rOH$, folic acid, hyaluronic acid, polyhistidine, cyclodextrin, heparin, chitosan, or protamine to provide a phosphazene polymer.

Furthermore, the compound that $R^{10}$ is thiol group or vinyl group or the compound protected by the thiol group or vinyl group, which is capable of cross-linking by irradiating the ultraviolet and adding cross-linking agent, and/or enzyme to the product having the various functional groups obtained from step (6), step (6-1), or step (6-2), is reacted with a compound selected from the group consisting of an acrylate-based compound, a methacrylate-based compound, an acrylamide-based compound, a vinylsulfone-based compound, a thiol-based compound, a cysteine-based compound, a cysteamine-based compound, a mercaptic acid-based compound, an allyl pyrimidine-based compound, and compounds including a thiol- or vinyl-group protected with a protecting group of the above compounds, or a tyramine-based compound, a tyrosine-based compound, and a phenol derivative to provide a phosphazene-based polymer that the reactive group being capable of cross-linking is directly chemical-bond [step (7)].

When the Chemical Formula 6 or $R^6$ and/or $R^{10}$ is protected by the protecting group in the step (7), the preparation method according to the present invention may further include a step [step (7-1)] of subjecting the polymer obtained from the step (7) to the deprotecting reaction to provide a polymer that $R^6$ and/or $R^{10}$ have a thiol functional group or the various vinyl functional groups.

The method of preparing the phosphazene-based polymer being capable of cross-linking represented by Chemical Formula 1 can be illustrated as in the following Reaction Scheme 1:

(Reaction Scheme 1)

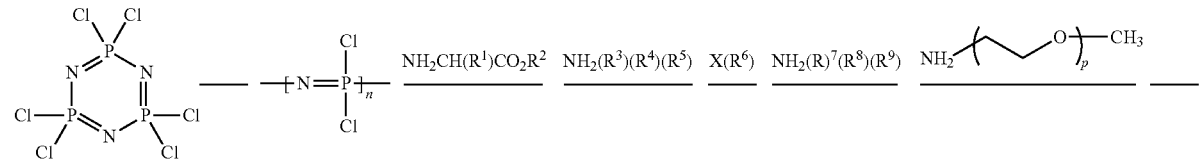

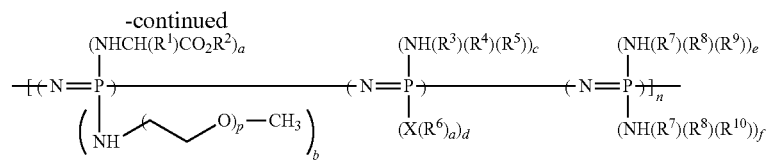

In the above Formula 4, 5, 6, and 7 and reaction scheme 1, $R^1$, $R^2$, $R^3$, $R^4$, $R^5$, $R^6$, $R^7$, $R^8$, $R^9$, $R^{10}$, a, b, c, d, e, f, n, and p are the same as one defined in the compound of the Chemical Formula 1.

Hereafter, the method of preparing a phosphazene polymer having a functional group represented by Chemical Formula 1 is detailed described. In the preparing process, the vacuum and/or the nitrogen line is used to prevent introducing moisture. All kinds of solvents sufficiently remove water by the general ways.

The step (1) can be performed by introducing the compound represented by Chemical Formula 2 and 0.1 to 10 wt % of $AlCl_3$ into a glass reactor and sealing the same, then reacting at 200 to 250° C. for 4 to 8 hours while circulating at a rate of one cycle per a minute.

The step (2) can be performed by reacting 1 equivalent of the product of step (1) with 0.01 to 1.9 equivalent of amino acid ester represented by Chemical Formula 4 or a salt thereof under the presence of 4 equivalents of triethylamine. Preferably, the salt in the above formula 4 is hydrogen chloride or sulfate. A reaction solvent may include tetrahydrofuran (THF), dioxane, chloroform, or toluene, but is not limited thereto. It may be reacted at a reaction temperature ranging from −60 to 50° C. for about 8 to 72 hours.

The step (3) can be performed by reacting the product of step (2) with 0 to 1.9 equivalent of amino acid, peptide, depsipeptide ester represented by Chemical Formula 5, or a salt thereof under the presence of 4 equivalents of triethylamine. Preferably, the salt of compound represented by Chemical Formula 5 is oxalate, hydrogen chloride, or a trifluoric acid salt. The reaction solvent may include acetonitrile, tetrahydrofuran, dioxane, chloroform, or toluene, but is not limited thereto. It is preferable that it is reacted at a reaction temperature ranging from 0 to 50° C. for 1 to 72 hours.

The step (4) may be performed by reacting the product of step (3) with 0.01 to 1.9 equivalent of substitutent, represented by Chemical Formula 6, having a functional group being capable of cross-linking or a salt thereof under the presence of 4 equivalents of triethylamine. The salt of compound represented by Chemical Formula 7 may include oxalate, hydrogen chloride, or a trifluoric acid salt. It is preferable that the reaction temperature ranges from 25 to 50° C., and the reaction time ranges from 12 to 72 hours.

The step (5) can be performed by reacting the product of step (3) and the product of step (4) with 0.01 to 1.9 equivalent of substitutent having a functional group, represented by Chemical Formula 7, or a salt thereof under the present of 4 equivalent of triethylamine. The salt of compound represented by Chemical Formula 6 includes oxalate, hydrogen chloride, or a trifluoric acid salt. The reaction solvent may include acetonitrile, tetrahydrofuran, dioxane, chloroform, or toluene, but is not limited thereto. It is preferable that the reaction temperature ranges from 25 to 50° C., and the reaction time ranges from 12 to 72 hours in order to occur the sufficient reaction and suitable polymerization suppression.

In the step (6), based on the chlorine remained in the product of step (4) or step (5), it is reacted with 2 equivalents of aminomethoxy polyethylene glycol represented by Chemical Formula 8 under the presence of 4 equivalents of triethylamine to substitute all chlorine groups remained in products of the step (4) or the step (5). The reaction solvent may include at least one selected from the group consisting of tetrahydrofuran, dioxane, chloroform, and toluene, but it is not limited thereto. It is preferable that the reaction temperature ranges from 25 to 50° C., and the reaction time ranges from 24 to 72 hours.

When $R^9$ is $CH_2C_6H_5$ in Chemical Formula 7, the step (6-1) is performed by subjecting 50 to 90 wt % of palladium/charcoal or palladium black of product of step (6) to the dehydrogenation reaction under the presence of the hydrogen gas and pressure of 30 to 80 psi to substitute with carboxyl group. The reaction solvent may include methanol and/or ethanol, but it is not limited thereto. It is preferable that the reaction temperature ranges from 10 to 35° C., and the reaction time ranges from 1 to 24 hours. When $R^9$ is $CH_2CHCH_2$ in Chemical Formula 7, the product of the step (6) is deallylestericated with 10 to 20 mol % of tetrakis triphenylphosphine palladium (0) under the presence of 10 to 20 equivalent of morpholine to substitute with carboxyl group. The reaction solvent may include at least one selected from the group consisting of tetrahydrofuran, dioxane, chloroform, and toluene, but it is not limited thereto. It is preferable that the reaction temperature ranges from 0 to 25° C., and the reaction time ranges from 1 to 24 hours. When $R^9$ is OH in Chemical Formula 7, the product of the step (5) is esterificated with 1 to 5 times mole of various cyclic anhydride under the presence of 1 to 5 times mole of 4-dimethyl amino pyridine to transfer to carboxyl group. The cyclic anhydride may include any general cyclic anhydrides, for example may be at least one selected from the group consisting of succinic anhydride, maleic anhydride, 2,3-dichloromaleic anhydride, tetrafluorosuccinic anhydride, diglycolic anhydride, citraconic anhydride, itaconic anhydride, glutaric anhydride, cis-aconitic anhydride, dimethylmaleic anhydride, 1-cyclopentene-1,2-dicarboxylic anhydride, phthalic anhydride, 3,6-dichlorophthalic anhydride, 3-fluorophthalic anhydride, 4-fluorophthalic anhydride, 3-nitrophthalic anhydride, 4-nitrophthalic anhydride, 3-hydroxyphthalic anhydride, isatoic anhydride, and the like, but is not limited thereto. The cyclic anhydride refers to all cyclic anhydrides, and the reaction solvent may include tetrahydrofuran, dioxane, and it is not limited thereto. It is preferable that the reaction temperature ranges from 20 to 50° C., and the reaction time ranges from 1 to 48 hours.

In step (6-2), the product of the step (6) including carboxylic acid or the product of step (6-1) is reacted with lysine, arginine, cysteine, thiolan alkylamine, or a various molecular weight of polyethyleneimine, polylysine, polyarginine, folic acid, hyaluronic acid, polyhistidine, cyclodextrin, heparin, chitosan, or protamine under the presence of 1 to 3 equivalents of dicyclohexyl carbodi imide under the presence of 1 to 3 equivalents of hydroxyl succinimide to provide a phosphazene-based polymer having the various functional groups. The reaction solvent may include tetrahydrofuran and/or chloroform, but it is not limited thereto. It is preferable that the reaction temperature ranges from 0 to 25° C., the reaction time ranges from 1 to 48 hours.

In step (7), the substitutents having a functional group being capable of cross-linking with the product of step (6), the product of step (6-1), or the product of step (6-2) having the various functional groups can be bound to the phosphazene polymer through disulfide bond [Int. J. Cancer, 73, 859-864 1997], carbamite bond [I. Biochem. Pharmacol, 34, 289 1985], or hydrazone bond [J. Control Release, 73, 89-102 2001].

In addition, in step (7-1), when $R^6$ and $R^{10}$ are groups consisting of protecting groups in the steps 6 and 7, the polymer obtained from step (6) and step (7) are subjected to the deprotection reaction to let $R^6$ and $R^{10}$ have a thiol functional group or the various vinyl functional groups.

In step (4) and/or step (7), the polymerization inhibitor may be added in an amount of $10^{-4}$ to $10^{-2}$ wt % based on the total weight of the reactants of the corresponding step. In the vinyl compound being capable of cross-linking by irradiating the ultraviolet (UV), the cross-linking can be unintentionally progressed before obtaining the final resultant by progressing the cross-linking by accidental temperature increase and ultraviolet exposure during the synthesis reaction, which is before the desirable cross-linking process. The polymerization inhibitor acts to suppress the spontaneous cross-linking between the polymers before the cross-linking reaction. The amount of the polymerization inhibitor is determined as much as the cross-linking can be suppressed as long as it does not affect on the synthesis. The polymerization inhibitor may include generally-used materials, for example, is selected from the group consisting of nitrobenzene, 1,3,5-trinitrobenzenebenzene, p-benzoquinone, chloranil, 1,1-diphenyl-2-picrylhydrazyl, ferric chloride, chloridecopper, oxygen, sulfur, aniline, phenol, p-dihydroxybenzene, 1,2,3-trihydroxybenzene, 2,4,6-trimethylphenol, monomethyl ether hydroquinone, methoxy hydroquinone, 2,2-diphenyl-1-picrylhydrazyl, 2,2-di(4-tert-octylphenyl)-1-picrylhydrazyl, 3-carboxyl-proxyl, 3-cyano-proxyl, 3-(2-Iodoacetamido)-proxyl, 3-maleimido-proxyl, garbinoxyl, 2,2,3,4,5,5-hexamethyl-3-imidazolinium-1-yloxy methyl sulfate, 4-(1-hydroxy-1-methylethyl)-2,2,5,5-tetramethyl-3-imidazolinium-1-yloxy, 4-phenacylidene-2,2,5,5-tetramethylimidazolidin-1-yloxy, 4-phenyl-2,2,5,5-tetramethyl-3-imidazolin-1-yloxy, tris(4-bromophenyl)ammoniumyl hexachloroantimonate, 3β-DOXYL-5α-cholestane, 5-DOXYL-Stearic acid, 16-DOXYL-stearic acid, methyl 5-DOXYL-stearate, 4-acetamido-TEMPO, 4-acetamido-2,2, 6,6-tetramethylpiperidine 1-oxyl, 4-(2-bromoacetamido)-TEMPO, 4-carboxyl-TEMPO, 4-carboxyl-2,2,6,6-tetramethylpiperidine 1-oxyl, 4-(2-chloroacetamido)-2,2,6,6-tetramethylpiperidine 1-oxyl purum, 4-cyano-TEMPO, 4-hydroxy-TEMPO, 4-hydroxy-TEMPO benzoate, 4-(2-iodoacetamido)-TEMPO, 4-maleimido-TEMPO, 4-methoxy-TEMPO 97, 4-oxo-TEMPO, TEMPO, 4-isothiocyanato-2,2, 6,6-tetramethylpiperidine 1-oxyl purum, 2,2,6,6-tetramethyl-4-(methylsulfonyloxy)-1-piperidinooxy, and 2,2,6,6-tetramethylpiperidine 1-oxyl purum, but is not limited thereto. The reaction solvent may be at least one selected from the group consisting of acetonitrile, tetrahydrofuran, dioxane, chloroform, and toluene.

In steps 1 to 6, the product of each step may be used with no purification process and used for the reaction of the next step. Purified production can be recovered from the reaction mixtures of the step (6), step (7), and step (7-1) according to the following purification method.

Firstly, the reaction mixture is centrifuged or filtrated to remove the precipitate (for example, triethylammonium chloride, triethyl ammonium salt of oxalic acid and so on) from the reaction mixture. The filtrate is concentrated under the reduced pressure until the solvent is slightly remained. The obtained concentrated solution is dissolved in tetrahydrofuran, and an excessive ethylether, hexane or a mixed solvent of ethylether and hexane is added to induce the precipitation of product and filtrated. These steps are repeated for 2 to 3 times to remove unreacted substitutents. The obtained compound is dissolved in a small amount of methanol or ethanol to dialysis with methanol or ethanol at 25° C. for 3 to 10 days and to dialysis with a distilled water at 4 to 25° C. for 3 to 10 days, then it is dried at a low temperature to provide a pure compound represented by Chemical Formula 1.

On the other hand, the present invention provides a hydrogel including at least one polymer solution selected from the group consisting of phosphazene-based polymers represented by Chemical Formula 1; forming a chemical cross-linking formed by an ultraviolet (UV) radiation and/or treatment with a thiol-based or vinyl based cross-linking agent and/or a mixture of a thiol-containing phosphazene-based polymer and a vinyl-containing phosphazene-based polymer; and showing a sol-gel behavior and an excellent hardness.

(Chemical Formula 1)

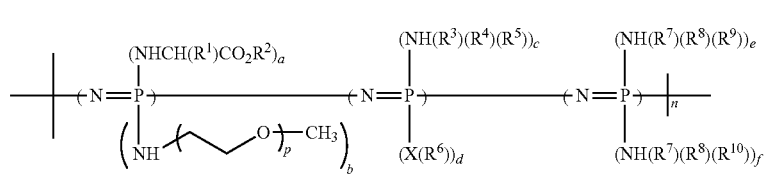

wherein, in the above formula,
$R^1, R^2, R^3, R^4, R^5, R^6, R^7, R^8, R^9, R^{10}$, a, b, c, d, e, f, n, and p of the above formula 4, 5, 6, 7 and reaction scheme 1 are the same as one defined in the compound of the Chemical Formula 1.

As mentioned in above, the solution (hydrogel) of phosphazene-based polymer according to the present invention represented by Chemical Formula 1 is biodegradable and has characteristics being capable of cross-linking. It shows a distinct sol-gel behavior depending upon the temperature change and upon the kind and the composition ratio of substitutents of phosphazene-based polymer represented by Chemical Formula 1. The biodegradable hydrogel with cross-linking according to the present invention may be prepared by dissolving the phosphazene-based polymer of Chemical Formula 1 in at least one suitable solvent selected from the group consisting of water, buffer solution, acid solution, alkali solution, salt solution, saline, injecting water, and glucose saline in a concentration of 1 to 50 wt %. It is preferable that the concentration ranges from 3 to 30 wt %. The phosphazene-based polymer according to the present invention shows a sol-gel behavior at a temperature ranging from 5 to 70° C., and preferably at a temperature ranging from 20 to 45° C., so it forms a gel at a body temperature range. As a result, it can be applied to a carrier material for in vivo delivering the various physiological active materials such as a drug or a cell.

As mentioned above, the hydrogel according to the present invention forms a chemical cross-linking between vinyl groups by the ultraviolet radiation or a chemical cross-linking due to the Michael-addition-type reaction between the thiol group and the vinyl group present in the polymer. Therefore, the hydrogel has a dense network structure and the small pore size as well as shows a sol-gel behavior depending upon the temperature change and an enough gel solidity required for the carrier for the hydrophilic drug transporter, so that it has merits of an excellent drug-supporting capacity, drug-release-controlling capacity, and a capacity of maintaining the suitable solidity and volume for a long time.

In other hydrogels of the present invention, the chemical cross-linking can be formed by at least one of the following four conditions:

1) Forming chemical cross-linking by using a mixture of at least one phosphazene-based polymer solution having a thiol substitutent and at least one phosphazene-based polymer solution having a vinyl substitutent;

2) Forming chemical cross-linking by irradiating ultraviolet;

3) Forming chemical cross-linking by treating a cross-linking agent; and

4) Forming chemical cross-linking by treating an enzyme.

Firstly, 1) when the chemical cross-linking can be formed by mixing the solution of phosphazene polymer having a thiol substitutent and the solution of phosphazene polymer having a vinyl substitutent, at least one phosphazene-based polymer solution that $R^6$ and/or $R^{10}$ is a substitutent having a thiol group in Chemical Formula 1 is mixed with at least one phosphazene-based polymer solution that $R^6$ and/or $R^{10}$ is a substitutent having a vinyl group in Chemical Formula 1. Then, a Michael-addition-type reaction between the thiol group and the vinyl group is carried out to form a chemical cross-link. The cross-linking formation can be supported or accelerated by further adding at least one photo-initiator and/or at least one cross-linking agent listed in the follows:

In a case of 2), which is a case of phosphazene polymer that $R^6$ and/or $R^{10}$ is a substitute having vinyl group in Chemical Formula 1, it can form a chemical cross-linking by irradiating ultraviolet (UV), so that it can form the chemical cross-linking by irradiating ultraviolet (UV) and optional adding the photoinitiator. Accordingly, the hydrogel may include at least one solution of phosphazene polymer represented by Chemical Formula 1 and a photo-initiator. The amount of the photo-initiator may range from $1 \times 10^{-6}$ to 10 wt % and preferably $1 \times 10^{-3}$ to 1 wt % based on the total weight of phosphazene-based polymer. When the amount of photo-initiator is less than the range, it is impossible to obtain the desirable effects of photo-initiator; on the other hand, when the amount is more than the range, it affects on the effect of the effective ingredients and the physical property of the polymer showing the sol-gel behavior.

The photo-initiator useful in the present invention may include any compounds as long as it can form a radical by being irradiated, for example, it may be at least one selected from the group consisting of ketone-based compound, phosphine oxide-based compound, an alkylester-based compound, benzoyl-based compound, titanate, iodonium salt, dibenzoyl-based compound, thiocarbonate-based compound, dion-based compound, and potassium sulfate. More preferably, the photoinitiator is at least one selected from the group consisting of benzoyl peroxide, 2,2-dimethoxy-2-phenyl acetophenone, 2-hydroxy-1-[4-(2-hydroxytoxy)phenyl]-2-methyl-1-propanone, acylphosphineoxide-based compound, methylbenzoylformate, oxy-phenyl-acetic acid 2-[2-oxo-2-phenyl-acetoxy-ethoxy]ethyl ester, oxy-phenyl-acetic 2-[2-hydroxy-ethoxy]-ethyl ester, α,α-dimethoxy-α-phenylacetophenone, 2-benzyl-2-(dimethylamino)-1-[4-(4-morpholinyl)phenyl]1-butanone, benzophenone, 2-hydroxy-4'-(2-hydroxyethoxy)-2-methylpropinophenone, 1-hydroxy-cyclohexyl-phenyl-ketone, 2-methyl-1-[4-(methylthio)phenyl]-2-(4-morpholinyl)1-propanone, 1-[4-(2-hydroxyethoxy)-phenyl]-2-hydroxy-2-methyl-1-propan-1-one, 2-hydroxy-2-methyl-1-phenyl-1-propanone, diphenyl (2,4,6-trimethylbenzoyl)-phosphine oxide, phosphine oxide, phenyl bis(2,4,6-trimethylbenzoyl), bis(eta 5-2,4-cyclopentadien-1-yl)titanium, bis[2,6-difluoro-3-(1H-pyrrol-1-yl) phenyl]titanium, iodonium, (4-methylphenyl)[4-(2-methylpropyl)phenyl iodonium salt, hexafluorophosphate iodonium salt, dibenzoyl disulfide-based compound, diphenyl thiocarbonate, 2,2'-azobisisobutynonitrile, camphorquinone(camphorquinone), eosine dye (dye eosin), potassium persulfate, potassium peroxodisulfate, and so on.

In a case of phosphazene polymer that $R^6$ and/or $R^{10}$ is a substitutent having a thiol group in Chemical Formula 1, it can form cross-linking by irradiating the ultraviolet and adding the photo-initiator together with adding a cross-linking agent having a vinyl group being capable of forming the cross-linking with the thiol group.

3) When it forms chemical cross-linking by the cross-linking agent, the hydrogel of the present invention may include at least one phosphazene-based polymer represented by Chemical Formula 1 and at least one cross-linking agent selected from the group consisting of a thiol-based cross-linking agent and a vinyl-based cross-linking agent. The thiol-based cross-linking agent can form a chemical cross-linking by carrying out a Michael-addition-type reaction with the vinyl group present in the posphazene polymer; the vinyl-based cross-linking agent can form a chemical cross-linking by carrying out a Michael-addition-type reaction with each vinyl group or thiol group present in the phosphazene-based polymer. The added amount of cross-linking agent may ranges from $1 \times 10^{-6}$ to 30 wt % and preferably $1 \times 10^{-3}$ to 10 wt % based on the total weight of phosphazene-based polymer. When the amount of cross-linking agent is less than the range, it is impossible to obtain the desirable effects of cross-linking agent; on the other hand, when it is more than the range, it may affect on the effects of the effective ingredient and/or the sol-gel behavior physical property of the polymer.

The cross-linking agent useful in the present invention may include any material as long as it can carry out a Michael-addition-type reaction with a thiol or vinyl group of the Chemical Formula 1, so it can include any material having two or more thiol group and/or vinyl group. The cross-linking agent may be at least one compound having two or more thiol and/or vinyl, for example, a thiol-containing compound such as a thiol-based compound, a dithiol-based compound, and a mercapto-based compound, and a vinyl-containing compound such as sulfur-containing amino acid, sulfur-containing oligopeptide, an acrylate-based compound, a diacrylate-based compound, a triacrylate-based compound, a tetraacrylate-based compound, a pentaacrylate-based compound, a hexaacrylate-based compound, a methacrylate-based compound, a dimethacrylate-based compound, a (di) vinyl-based compound, a protoporphyin-based compound, a (di)vinyl-polyethyleneglycol-based compound, a (di)vinyl-sulfone-polyethyleneglycol-based compound, a diol-based compound, an allyl-based compound, a diallyl-based compound, a triallyl-based compound, and so on.

More preferably, the cross-linking agent may be at least one selected from the group consisting of toluene-3,4-dithiol, 4-amino-4H-1,2,4-triazole-3,5-dithiol, (1,2,4) thiadiazole-3,5-dithiol, 5-(4-chloro-phenyl)-pyrimidine-4,6-dithiol, 7-H-purine-2,6-dithiol, M-carborane-1,7 dithiol, O-carborane-1,2-dithiol, 1,3,4-thiadiazole, 1,6-hexanedithiol, 2,5-dithiol, benzene-1,2-dithiol, benzene-1,3-dithiol, biphenyl-4,4'-dithiol, bismuthiol, 2,3-dimercapto-1-propane sulfonic acid sodium salt monohydrate, 2,4-dimercapto-5-methyl pyrimidine, 2,6-dimercapto-7-methyl purine, 2,8-dimercapto-6-hydroxy purine, 6,8-dimercapto-2-hydroxy purine, 2,2'-(ethylenedioxy)diethane thiol, 1,3-dimercapto-1-propanol, 1,2-ethanedithiol, ethylene glycol dithioacetate, 1,5-dimercaptopentane, 1,3-propanedithiol, dimercaptomethane, pentaerythritol tetrakis(2-mercaptopropinonate), pentaerythritol tetrakis(3-mercaptopropinonate), trimethylolpropane tris(2-mercaptoacetate), trimethylolpropane tris(3-mercaptoacetate), dithiothreitol, thiol-substituted poly(ethylene glycol) derivatives such as a poly(ethylene glycol)-dithiol-based compound having a molecular weight of 200 to 2,500, a N-thiol-glycylglycylglycyl-terminated poly(ethylene glycol)-based compound, a 3-arm poly(ethylene glycol)-thiol-based compound having a molecular weight of 1,000 to 20,000, a 4-arm poly(ethylene glycol)-thiol-based compound having a molecular weight of 2000 to 20,000, a 8-arm poly(ethylene glycol)-thiol-based compound having a molecular weight of 10,000 to 40,000, thiol-substituted polymers such as poly(ethylene glycol-2-mercaptosuccinic acid) having a molecular weight of 200 to 25,000, biscysteine-oligopeptide, poly(ethylene glycol) derivatives having an acrylate substituent such as propylene glycol glycerolate diacrylate, di(ethylene glycol)diacrylate, tri(propylene glycol)diacrylate, tetra(ethylene glycol)diacrylate, tri(propylene glycol)glycerolate diacrylate, trimethylolpropane benzoate diacrylate, trimethylolpropane etoxylate methyl ether diacrylate, bisphenol A propoxylate diacrylate, bisphenol A propoxylate glycerolate diacrylate, bisphenol F etoxylate diacrylate, fluorescein O,O'-diacrylate, neopentyl glycol diacrylate, neopentyl glycol propoxylate diacrylate, pentaerythritol diacrylate monostearate, ethylene diacrylate, oxydiethylene diacrylate, 3-hydroxy-2,2-dimethylpropyl 3-hydroxy-2,2-dimethylpropinonate diacrylate, glycerol 1,3-diglycerolate diacrylate, 1,3-butanediol diacrylate, 1,4-butanediol diacrylate, 1,6-hexanediol diacrylate, 1,6-hexanediol etoxylate diacrylate, 1,6-hexanediol propoxylate diacrylate, bisphenol A etoxylate diacrylate having a molecular weight of 200 to 40,000, bisphenol A glycerolate diacrylate, pentaerythritol propoxylate triacrylate, pentaerythritol tetraacrylate, pentaerythritol triacrylate, trimethylpropane deoxylate triacrylate, trimethylolpropane propoxylate triacrylate, trimethylolpropane triacrylate, poly(ethylene glycol) triacrylate having a molecular weight of 200 to 2,500, poly(ethylene glycol) tetraacrylate having a molecular weight of 200 to 2,500, poly(ethylene glycol) octaacrylate having a molecular weight of 200 to 2,500, acrylated 1,6-bis(p-carboxylphenoxy)hexane, acrylate 1,3-bis(p-carboxylphenoxy)propane, acrylate sebacic acid, poly(propylene glycol)diacrylate having various molecular weights, a poly(ethylene glycol)-acrylate-based compound having a molecular weight of 200 to 2,500, a N-acrylate-glycylglycylglycyl-terminated poly(ethylene glycol)-based compound, a 3-arm poly(ethylene glycol)-acrylate-based compound having a molecular weight of 1,000 to 20,000, a 4-arm poly(ethylene glycol)-acrylate-based compound having a molecular weight of 2000 to 20,000, a 8-arm poly(ethylene glycol)-acrylate-based compound having a molecular weight of 10,000 to 40,000, a polymer having an acrylate substituent such as poly(ethylene glycol)-b-poly(lactic acid)-diacrylate having a molecular weight of 2,000 to 40,000, poly(ethylene glycol)-b-poly(glycolid)-diacrylate having a molecular weight of 2,000 to 40,000, poly(ethylene glycol)-b-poly(alpha-hydroxyl acid)-diacrylate having a molecular weight of 2,000 to 40,000, poly(ethylene glycol) derivatives having a methacrylate substituent, ethylene glycol dimethacrylate, bisphenol A dimethacrylate, 1,3-bis(3-metaacryloxyloxypropyl)-1,1,3,3-tetramethyldisiloxane, 1,3-butanediol dimethacrylate, 1,4-butanediol dimethacrylate, bisphenol A etoxylate dimethacrylate, bisphenol A glycerolate dimethacrylate, di(ethylene glycol)dimethacrylate, diurethane dimethacrylate, fluorescein O,O'-dimethacrylate, glycerol dimethacrylate, neopentyl glycol dimethacrylate, ethylene dimethacrylate, oxydiethylene dimethacrylate, di(ethylene glycol)dimethacrylate, poly(lauryl methacrylate-co-ethylene glycol dimethacrylate) having a molecular weight of 200 to 40,000, poly(methyl methacrylate-co-ethylene glycol dimethacrylate) having a molecular weight of 200 to 40,000, poly(propylene glycol) dimethacrylate having a molecular weight of 200 to 2,500, tetraethylene glycol dimethacrylate, triethylene glycol dimethacrylate, 2,2-bis[4-(2-hydroxy-3-methacryloyloxypropyl)phenyl]propane, etoxylate 2,2-bis[4-(2-hydroxy-3-metaacryloyloxypropyl)phenyl]propane, 1,6-bis-[2-metaacryloyloxyethoxycarbonylamino]2,4,4-trimethylhexane, dodecanediol dimethacrylate, trimethylolpropane trimethacrylate, methacrylated 1,6-bis(p-carboxylphenoxy)hexane, methacrylate 1,3-bis(p-carboxylphenoxy)propane, methacrylate sebacic acid, a poly(ethylene glycol)-methacrylate-based compound having a molecular weight of 200 to 2,500, a N-methacrylate-glycylglycylglycyl-terminated poly(ethylene glycol)-based compound, a 3-arm poly(ethylene glycol)-methacrylate-based compound having a molecular weight of 1,000 to 20,000, a 4-arm poly(ethylene glycol)-methacrylate-based compound having a molecular weight of 2000 to 20,000, a 8-arm poly(ethylene glycol)-methacrylate-based compound having a molecular weight of 10,000 to 40,000, a polymer having a methacrylate substitutent such as poly(ethylene glycol)-b-poly(lactic acid)-methacrylate having a molecular weight of 200 to 40,000, poly(ethylene glycol)-b-poly(glycolid)-methacrylate having a molecular weight of 200 to 40,000, poly(ethylene glycol)-b-poly(α-hydroxylic acid)-methacrylate having a molecular weight of 200 to 40,000, diethylene glycol divinyl ether, triethylene glycol divinyl ether, divinylbenzene, poly(1,4-butanediol)divinyl ether, polytetrahydrofuran divinyl ether, 1,6-hexanediol divinyl ether, 1,1,3,3,-tetramethyl-1,3-divinyldisiloxane, 1,3-divinyltetramethyldisiloxane, 1,4-pentadiene-3-ol, 1,4-divinyl-1,1,2,2,3,3,4,4-octamethyltetrasilane, 2,5-divinyltetrahydropyran, 3,9-divinyl-2,4,8,10-tetraoxaspiro[5,5]undecane, 3,6-divinyl-2-methyltetrahydrofuran, divinylphenylphosphine, poly(ethylene glycol)divinyl ether having a molecular weight of 200 to 2,500, poly(styrene-co-bromostyrene-co-divinylbenzene), poly(styrene-co-divinylbenzene), protoporphyin IX, protoporphyin IX dimethyl ester, protoporphyin IX disodium salt, protoporphyin IX zinc, molecular weight 1,000 to 20,000, a 3-arm poly(ethylene glycol)-vinyl-based compound, a 4-arm poly(ethylene glycol)-vinyl-based compound having a molecular weight of 2000 to 20,000, a 8-arm poly(ethylene glycol)-vinyl-based compound having a molecular weight 10,000 to 40,000, triallyl-1,3,5-triazine-2,4,6-1H, 3H, and 5H-trione, trimethylopropane diallyl ether, 1,6-hexadiene, divinyl sulfoxide, α,ω-divinyl sulfone-poly(ethylene glycol), vinyl sulfone-3-arm poly(ethylene glycol) having a molecular weight of 1000 to 20,000, vinyl sulfone-4-arm poly(ethylene glycol) having a molecular weight of 2000 to 20,000, vinyl sulfone-8-arm poly(ethylene glycol) having a molecular weight of 10,000 to 40,000, and 1,6-hexanediol di-(endo, exo-norborne-2-en-5-carboxylate), and so on.

In addition, 4) when the cross-linking is formed by enzyme, the hydrogel according to the present invention may include at least one phosphazene-based polymer represented by Chemical Formula 1 and oxydoreductase enzymes and/or hydrogen peroxide solution. In this case, the oxydoreductase enzymes refers to all enzymes being carrying out an enzyme-substrate reaction with tyramine or tyrosine present in the phosphazene-based polymer so as to form a enzymatic cross-link, for example, it may include at least one selected from the group consisting of transglutaminase, laccase, bilirubin oxidase (BOD), manganese (II), hematin, horseradish peroxidase, and so on. It is preferable that it includes horseradish peroxidase. The hydrogen peroxide functions catalysis and promotes the reaction together with the oxydoreductase. The enzyme is added in an amount of $1 \times 10^{-6}$ to 200 wt %, and preferably $1 \times 10^{-3}$ to 100 wt % based on the total weight of phosphazene-based polymer. When the amount of enzyme is less than the range, it is impossible to obtain a desirable enzyme effect; on the other hand, when it is more than the range, it affects on the desirable effect of an effective ingredient and/or the sol-gel behavior physical property of the polymer of the present invention.

The present invention also provides a method of preparing a hydrogel including preparing at least one solution of phosphazene-based polymer referenced by Chemical Formula 1; and forming a chemical cross-linking in the obtained polymer.

The chemical cross-linking may be formed by performing one of the following four methods:

1) Mixing the phosphazene-based polymer solution having thiol substitutent and the phosphazene-based polymer solution having vinyl substitutent;

2) Radiating Ultraviolet (UV);

3) Adding Cross-linking agent; and

4) Adding Enzyme.

When the chemical cross-linking is formed by mixing the phosphazene-based polymer solution having thiol substitutent and the phosphazene-based polymer solution having vinyl substitutent, at least one solution of phosphazene-based polymer that $R^6$ and/or $R^{10}$ is a substitutent having a thiol group in Chemical Formula 1 is mixed with at least one solution of phosphazene-based polymer that $R^6$ and/or $R^{10}$ is a substitutent having a vinyl group in Chemical Formula 1 to form a chemical cross-linking due to a Michael-addition-type reaction between the thiol group and the vinyl group or between the vinyl group and vinyl group. It can help or accelerate the cross-linking formation by further treating at least one photo-initiator and/or at least one cross-linking agent.

When the chemical cross-linking is formed by radiating ultraviolet (UV), the hydrogel may include at least one solution of phosphazene polymer represented by Chemical Formula 1 and photo-initiator. The amount of the photo-initiator may ranges from $1 \times 10^{-6}$ to 10 wt %, and preferably $1 \times 10^{-3}$ to 1 wt % based on the total weight of phosphazene-based polymer. When the amount of photo-initiator is less than the range, it is impossible to obtain the desirable effect of photo-initiator; on the other hand, when it is more than the range, it affects on the effect of effective ingredient and/or the physical property of polymer showing the sol-gel behavior according to the present invention.

The useful photo-initiator may include any compound as long as it can form a radical by the photo radiation, for example, it may be at least one selected from the group consisting of ketone-based compound, phosphine oxide-based compound, an alkylester-based compound, benzoyl-based compound, titanate, iodonium salt, dibenzoyl-based compound, thiocarbonate-based compound, dion-based compound, and potassium sulfate.

When the chemical cross-linking is formed by the cross-linking agent, the hydrogel according to present invention may include at least one phosphazene-based polymer represented by Chemical Formula 1 and at least one cross-linking agent selected from the group consisting of thiol-based cross-linking agent and vinyl-based cross-linking agent. The thiol-based or vinyl-based cross-linking agent is a compound having at least two of thiol group and/or vinyl group, being capable of forming a chemical cross-linking by inducing the Michael-addition-type reaction with thiol group or vinyl group present in the phosphazene-based polymer. The amount of cross-linking agent ranges from $1 \times 10^{-6}$ to 30 wt %, and preferably $1 \times 10^{-3}$ to 10 wt % based on the total weight of phosphazene-based polymer. When the amount of cross-linking agent is less than the range, it is impossible to obtain the desirable effect of cross-linking agent; on the other hand, when it is more than the range, it affects on the effect of an effective ingredient and/or the sol-gel behavior physical property of polymer according to the present invention.

The cross-linking agent useful in the present invention may include any material being capable of generating a Michael-addition-type reaction with the thiol group and/or vinyl group represented by Chemical Formula 1. The cross-linking agent may be a compound having a thiol and a compound two or more vinyl, for example, be selected from the group consisting of a compound having a thiol such as a thiol-based compound, a dithiol-based compound, and a mercapto-based compound, and a compound having a vinyl such as sulfur-containing amino acid, sulfur-containing oligopeptide, an acrylate-based compound, a diacrylate-based compound, a triacrylate-based compound, a tetraacrylate-based compound, a pentaacrylate-based compound, a hexaacrylate-based compound, a methacrylate-based compound, a dimethacrylate-based compound, a (di)vinyl-based compound, a protoporphyin-based compound, a (di)vinyl-polyethyleneglycol-based compound, a (di)vinylsulfone-polyethyleneglycol-based compound, a diol-based compound, and so on. Specific useable cross-linking agent is as above described.

When the cross-linking is formed by enzyme, the hydrogel according to the present invention may include at least one phosphazene-based polymer represented by Chemical Formula 1 and hydrogen peroxide and oxydoreductase enzymes. In this case, the oxydoreductase enzymes may include any enzyme as long as it can form a enzymatic cross-linking by the enzyme-substance with tyramine or tyrosine present in the phsohazene-based polymer, for example, it may include transglutaminase, laccase, bilirubin oxidase (BOD), manganese (II), hematin, horseradish peroxidase and so on. It is preferable that it includes horseradish peroxidase. The hydrogen peroxide functions as a catalyst, and it act a role to promote the reaction together with oxydoreductase. The used amount of enzyme ranges from $1 \times 10^{-6}$ to 200 wt % and preferably $1 \times 10^{-3}$ to 100 wt % based on the total weight of phosphazene-based polymer. When the amount of enzyme is less than the range, it is impossible to obtain the desirable effect of enzyme; on the other hand, when it is more than the range, it affects on the effect of an effective ingredient and/or the sol-gel behavior physical property of polymer according to the present invention.

On the other hand, the present invention also provides a phosphazene-based polymer represented by the following Chemical Formula 1 or a hydrogel including the phosphazene-based polymer and a carrier for delivering a physiological active material including a physiological active material:

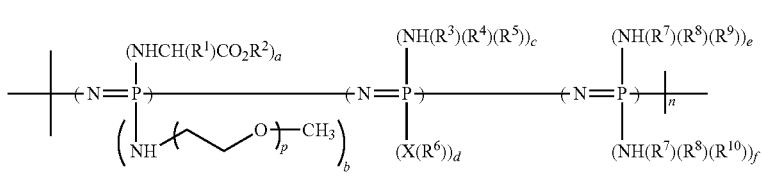

(Chemical Formula 1)

wherein, in the above formula, $R^1$, $R^2$, $R^3$, $R^4$, $R^5$, $R^6$, $R^7$, $R^8$, $R^9$, $R^{10}$ to, a, b, c, d, e, f, n, and p of the above formula 4, 5, 6, 7, and reaction scheme 1 are the same as one defined in the compound of the Chemical Formula 1.

The hydrogel included in the carrier for delivering the physiological active material according to the present invention shows a sol-gel behavior depending upon the temperature change and forms a cross-link. It may be a solution that at least one phosphazene-based polymer represented by Chemical Formula 1 is dissolved in a solvent selected from the group consisting of buffer solution, acidic solution, alkali solution, salt solution, water, saline, water for injection, and glucose saline in a concentration of 1 to 50 wt %, and preferably 3 to 30 wt %.

The physiological active material delivered by the carrier according to the present invention may include any material as long as it show beneficial effects in the body, for example, it may include at least one selected from the group consisting of a drug and a treatment cell. The drug may be at least one selected from the group consisting of protein, polypeptide, peptide, vaccine, gene, hormone, anti-cancer drug, and angiogenesis inhibitor.

The protein, polypeptide, and a peptide may be at least one selected from the group consisting of exendin-4, erythropoietin (EPO), interferon-alpha, interferon-beta, interferon-gamma, growth hormone (human, pig, cow and so on), a growth hormone releasing factor, a nerve growth factor, NGF, G-CSF (granulocyte-colony stimulating factor), GM-CSF (granulocyte macrophage-colony stimulating factor), M-CSF (macrophage-colony stimulating factor), a blood clotting factor, insulin, oxytocin, vasopressin, adrenocorticotropic hormone, a fibroblast growth factor, FGF, an epidermal growth factor, EGF, a platelet-derived growth factor (PDGF), an insulin-like growth factor (IGF), vascular endothelial growth factor, VEGF, a transforming growth factor-beta (TGF-β), a nerve growth factor, a brain-derived neurotrophic factor (BDNF), neurotrophin-3 NT-3, neurotrophin-4/5), prolactin, luliberin, luteinizing hormone releasing hormone (LHRH), LHRH agonists, LHRH antagonists, somatostatin, glucagon, interleukin-2 IL-2, interleukin-11 IL-11, gastrin, tetragastrin, pentagastrin, urogastrone, secretin, calcitonin, enkephalins, endorphins, angiotensins, thyrotropin releasing hormone (TRH), tumor necrosis factor (TNF), tumor necrosis factor related apoptosis inducing ligand (TRAIL), heparinase, bone morphogenic protein (BMP), hANP (human atrial natriuretic peptide), glucagon-like peptide (GLP-1), renin, bradykinin, bacitracins, polymyxins, colistins, tyrocidine, gramicidins, cyclosporins, neurotensin, tachykinin, neuropeptide Y (NPY), peptide YY (PYY), vasoactive intestinal polypeptide (VIP), pituitray adenylate cyclase-activating polypeptide (PACAP), and synthetic analogs, monoclonal antibody, antibody, modified or drug-effective moieties, enzymes, and cytokine.

The vaccine may be selected from the group consisting of a hepatitis vaccine and so on.

The gene may be at least one selected from the group consisting of small interference RNA (siRNA), plasmid DNA, and antisense oligodeoxynucleotide (AS-ODN), and so on.

The hormone may be at least one selected from the group consisting of testosterone, estradiol, progesterone, prostaglandins, and synthetic analogs thereof, and modified or drug-effective materials.

The anti-cancer drug may be at least one selected from the group consisting of paclitaxel, doxorubicin, 5-fluorouracil, cisplatin, carboplatin, oxaliplatin, tegafur, irinotecan, docetaxel, cyclophosphamide, cemcitabine, ifosfamide, mitomycin C, vincristine, etoposide, methotrexate, topotecan, tamoxifen, vinorelbine, camptothecin, danuorubicin, chlorambucil, bryostatin-1, calicheamicin, mayatansine, levamisole, DNA recombinant interferon alfa-2a, mitoxantrone, nimustine, interferon alfa-2a, doxifluridine, formestane, leuprolide acetate, megestrol acetate, cannofur, teniposide, bleomycin, carmustine, heptaplatin, exemestane, anastrozole, estramustine, capecitabine, goserelin acetate, saccharide potassuim, medroxypogexterone acetate, epirubicin, letrozole, pirarubicin, topotecan, altretamine, toremifene citrate, BCNU, taxotere, actinomycin D, Anasterozole, Belotecan, Imatinib, Floxuridine, Gemcitabine, Hydroxyurea, Zoledronate, Vincristine, Flutamide, Valrubicin, Streptozocin, polyethylene glycol junction anti-cancer drug, and synthetic analogs thereof, and modified or drug-effective materials.

The angiogenesis inhibitor may be at least one material selected from the group consisting of BMS-275291(Bristol-Myers Squibb, New York, N.Y.), 6-deoxy-6-demethyl-4-dedimethyl aminotetracycline (COL-3), doxycycline, marimastat, 2-methoxyestradiol, squalamine, SU5164, thalidomide, TNP-470, combretastatin A4, Soy isoflavone, enzastaurin, CC 5013 (Revimid; Celgene Corp, Warren, N.J., (Celecoxib, ZD 6474, halofuginone hydrobromide, interferon-alpha, bevacizumab, AE-941, interleukin-12, VEFG-trap, cetuximab, rebimastat, a MMP inhibitor (for example, BMS-275291 (Bristol-Myers Squibb, New York, N.Y., S-3304, and so on), a protein kinase C beta inhibitor, for example, LY317615), endostatin, vatalanib, (PTK787/ZK 222584), sunitinib malate (SU11248), cilenqitide (EMD-121974), human monocolonal antibody MEDI-522, EOS-200-4, integrin alpha-5-beta-1 antagonist (ATN-161), and synthetic analogs thereof, and modified or drug-effective materials.

The treatment cell may include at least one selected from the group consisting of a preosteoblast, a chondrocyte, a umbilical vein endothelial cell (UVEC), a osteoblast, an adult stem cell, a schwann cell, an oligodendrocyte, hepatocyte, a mural cell (combined with the UVEC), myoblast, an insulin secreting cell, an endothelial cell, a smooth muscle cell, a fibroblast, a β cell, an endodermal cell, a hepatic stem cell, a juxtaglomerular cell, skeletal muscle cell, a keratinocyte, a melanocyte, a langerhans cell, a merkel cell, a dermal fibroblast, and a preadipocyte.

When the carrier of delivering a physiological active material includes a drug as a physiological active material, the drug is supported in the carrier for a physiological active material in amount ranging from $1\times10^{-8}$ to 50% by volume and preferably $1\times10^{-4}$ to 20% by volume based on the total volume. When the carrier for a physiological active material supports a cell as a physiological active material, the amount of cell supported in the carrier for a physiological active material ranges from $1\times10^{-8}$ to 50% by volume based on the total volume. When the amount of drug or cell is less than the range, it is impossible to obtain the desirable effect of drug; on the other hand, when it is more than the range, it affects on the physical property of polymer.

The physiological active material may be added to the phosphazene-based polymer by itself or it can be added and mixed before the addition of the photo-initiator and/or the cross-linking agent and/or the enzyme or simultaneously. After it is injected in body, it can be effectively supported in a polymer by cross-linking between polymers or by cross-linking formed by photo-initiator and/or cross-linking agent and/or enzyme together with the gelation of the polymer.

The carrier for the physiological active material including a phosphazene-based polymer represented by Chemical Formula 1 or a phosphazene-based polymer hydrogel and a physiological active material may further include additives such as the follows:

As mentioned in above, the carrier for the physiological active material including the phosphazene-based polymer represented by Chemical Formula 1 the hydrogel can increase the effectiveness of the carrier material for the physiological active material such as a drug of polymer hydrogel by further adding the various additives. For example, it can control the sol-gel behavior of the phosphazene-based polymer aqueous solution by adding the various salts to provide the desirable gel solidity and the sol-gel change temperature (Macromolecules 32, 7820, 1999). If it is required to deliver a polypeptide or a protein drug, it can be keep the stability of drug in the hydrogel by introducing the suitable additives; and it can control the release rate of a drug from the hydrogel by introducing the chemical link between the drugs and additives such as the ionic linkage. When it is required to deliver the treatment cell, it can increase the cell activity after delivering in body by the introduced additives.

In the other words, the additive may introduce the various interactive actions for the chemical link such as ionic linkage of the phosphazene-based polymer or phosphazene-based polymer hydrogel to the physiological active material such as a drug, so that it can control the release of the physiological active material and/or increase the bioactivity of physiological active material such as the treatment cell.

The amount of additive ranges from $1\times10^{-6}$ to 30 wt % and preferably $1\times10^{-3}$ to 10 wt % based on the total weight of the carrier for the physiological active material. When the amount of additive is less than the range, it is impossible to obtain the desirable effect of additive; on the other hand, when it is more than the range, it affects on the effect of an effective ingredient and/or the physical property of polymer according to the present invention.

The additive may include any material as long as it can introduce the various interactions between the phosphazene-based polymer and the physiological active material, and may be at least one selected from the group consisting of a cationic polymer having a molecular weight of 200 to 750,000, an anionic polymer having a molecular weight of 200 to 750,000, amino acid, a peptide, a protein, fatty acid, phospholipids, vitamin series, drug, polyethyleneglycol ester, steroids, amine compound, acryl-based copolymer, organic solvent, a preservative, sugar series, a polyol, a polyol including a sugar, amino acid including a sugar, a surfactant, sugar-included ion, silicate, metal salts, and ammonium salts.

Specific examples of the additive may include a positive ion polymer such as poly-L-arginine, poly-L-lysine, poly (ethylene glycol), polyethylenimine, chitosan, protamin, and so on (e.g., molecular weight 200 to 750000); PVA, a anionic polymer such as hyaluronic acid, chondroitin sulphate, heparin, alginate, and so on; a growth factor such as amiloride, procainamide, acetyl-beta-methylcholine, spermine, spermidine, lysozyme, fibroin, albumin, collagen, transforming growth factor-beta (TGF-beta), fibroblast growth factor: bFGF, vascular endothelial growth factor; VEGF, and so on, a biomaterial such as bone morphogenetic proteins: BMPs, dexamethason, fibronectin, fibrinogen, thrombin, a protein, dexrazoxane, leucovorin, ricinoleic acid, phospholipid, small intestinal submucosa, vitamin E, polyglycerol ester of fatty acid, Labrafil, M1944CS, cardioxane, glutamic acid, hydroxypropyl methylcellulose, gelatin, isopropyl myristate, Eudragit, tego betain, dimyristoylphosphatidylcholine, scleroglucan, and so on; an organic solvent such as chromophore EL, ethanol, dimethylsulfoxide, and so on; a preservative such as methylparaben: starch, cyclodextrin and derivatives thereof, sugar series such as lactose, glucose, dextran, mannose, sucrose, trehalose, maltose, ficoll, and so on; a polyol such as inositol, mannitol, sorbitol, and so on; a polyol including a sugar such as sucrose-mannitol, glucose-mannitol, and so on, amino acid such as alanine, arginine, glycine, and so on; a polyol including a polymer such as trehalose-PEG, sucrose-PEG, sucrose-dextran, and so on; amino acid including a sugar such as sorbitol-glycine, sucrose-glycine, and so on; a poloxamer having various a molecular weight, Tween 20, Tween 80, Triton X-100, sodium dodecyl sulfate (SDS), a surfactant such as Brij; sugars-ions such as trehalose-$ZnSO_4$, maltose-zinc sulfate (maltose-$ZnSO_4$), and so on, salts such as silicate, NaCl, KCl, NaBr, NaI, LiCl, n-Bu4NBr, n-$Pr_4NBr$, $Et_4NBr$, $Mg(OH)_2$, $Ca(OH)_2$, $ZnCO_3$, $Ca_3(PO_4)_2$, $ZnCl_2$, $(C_2H_3O_2)_2Zn$, $ZnCO_3$, $CdCl_2$, $HgCl_2$, $CoCl_2$, $(CaNO_3)_2$, $BaCl_2$, $MgCl_2$, $PbCl_2$, $AlCl_3$, $FeCl_2$, $FeCl_3$, $NiCl_2$, $AgCl$, $AuCl_3$, $CuCl_2$, sodium dodecyl sulphate, sodium tetradecyl sulphate, dodecyltrimethylammonium bromide, dodecyltrimethylammonium chloride, tetradecyltrimethylammonium bromide, and so on.

Since the carrier for the physiological active material is present as a sol state at a room temperature according to the sol-gel behavior depending upon the polymer cross-linking and the sol-gel behavior depending upon the temperature change, it is easy to be injected by the various routes such as an injection. When it is injected in body, it turns to a gel states due to a body temperature, so that it is easy to control the release of physiological active material. In addition, the early excessive amount release is prevented by the hydrogel cross-link, so that it is possible to control the steady and effective release. It is preferable that the carrier material of delivering the physiological active material may be injected into the body by the administration such as oral administration, buccal administration, intranasal administration, intraperitoneal administration, a hypodermic injection, intramuscular injection, transdermal administration, or intratumor administration, and it is more preferable that it is administrated by a local administration such as a hypodermic injection, intramuscular injection, transdermal administration, or intratumor administration.

The provided phosphazene-based polymer being capable of cross-linking and the phosphazene polymer solution (hydrogel) including the same can be transformed from a solution state to a gel state depending upon the kind and composition ratio of the substitutent and upon the temperature change; in addition, it can transform from a solution state to a gel state by the ultraviolet radiation or a cross inking agent and the Michael-addition-type cross-linking between phosphazene-based polymer substituents, so that it is easy to control the sol-gel behavior and gel physical property. As a result, it can apply to the various industrial applications.

The phosphazene-based polymer being capable of cross-linking shows the sol-gel behavior due to the chemical cross-linking and also has temperature-sensitivity showing sol-gel behavior depending upon the temperature change, so that the gel solidity is stronger by the secondary ultraviolet (UV 365 nm, 0.61 mW/cm2) exposure, the cross-linking agent and/or the enzyme and the mixture of phosphazene-based polymers after the gel is easily formed by the temperature change. Thereby, it can apply to various applications such as a carrier material for a physiological active material such as a drug, a dental material such as an implant material or a tissue material such as an artificial cartilage. As it is possible to freely control the hydrogel pore size due to the chemical cross-link, the supporting capacity of the hydrophilic drug is excellent and the drug can be steadily released. Thereby, it can be used for a carrier material delivering a physiological active material such as a drug.

EXAMPLES

The present invention is further explained in more detail with reference to the following examples. These examples, however, is only for illustrating the present invention, and should not be interpreted as limiting the scope of the present invention in any manner.

In the examples below, the elementary analysis of carbon, hydrogen, and nitrogen for the product was performed by the Property Analysis Center in the Korea Advanced Institute of Science and Technology using the Perkin-Elmer C, H, N analyzer. The nuclear magnetic resonance spectrums with hydrogen and phosphorus were respectively measured by using Varian Gemini-300, and the average molecular weight ($M_w$) is measured through gel permeation chromatography using a Waters 1515 pump and a 2410 differentiation refractometer.

Example 1

Preparation of poly[(isoleucine ethyl ester)(aminomethoxy polyethyleneglycol 550)(aminoethylmethacrylate)phosphazene], $[NP(IleOEt)_{1.16}(AMPEG550)_{0.60}(AEMA)_{0.23}]_n$ Dried isoleucine ethyl ester hydrochloride salt (3.92 g, 20.02 mmol) was dissolved in 100 ml of anhydrous tetrahydrofuran, and then, triethylamine (6.08 g, 60.06 mmol) was added thereto. Poly(dichloro phosphazene) (2.00 g, 17.26 mmol) was dissolved in 50 ml of anhydrous tetrahydrofuran, and then slowly added dropwise to the obtained isoleucine ethyl ester hydrochloride salt solution in dry ice-acetone bath at −60° C., allowing to react for 48 hours with slowly increasing the temperature to the room temperature.

After checking the reaction progress by checking $^{31}$P-NMR, the solution of aminomethoxypolyethylene glycol of molecular weight 550 (14.24 g, 25.89 mmol) and triethylamine (7.86 g, 77.67 mmol) dissolved in anhydrous tetrahydrofuran (50 ml) was added dropwise to the obtained resulting product, allowing to react at the room temperature for 12 hours, and at 40-50° C. for 24 hours. After checking again the reaction progress by checking $^{31}$P-NMR, a solution of dried aminoethylmethacrylate hydrochloride salt (1.31 g, 7.94 mmol) dissolved in 10 ml anhydrous dimethylformamide, to which triethylamine (2.41 g, 23.82 mmol) was added, to the obtained reaction solution, allowing to react for 8 hours.

The reaction solution was filtered to remove a generated triethylamine hydrochloride salt. The remaining solution was concentrated under decompression until the solvent was mostly removed. The obtained concentrate solution was dissolved in tetrahydrofuran (10 ml) and an excess of hexane was added thereto to induce the formation of precipitation. After the process was repeated 2 or 3 times, the obtained precipitate was dissolved again in a small amount of methylalcohol. The resulting solution was put into an MWCO 12000 membrane (Spectrum Laboratories, Inc.), and dialyzed with methylalcohol at room temperature for 5 days and with distilled water for 5 days. The obtained product was dried at a low temperature, to produce poly(dichlorophosphazene), $[NP(IleOEt)_{1.16}(AMPEG550)_{0.60}(AEMA)_{0.23}]_n$ 9.32 g (yield 76%).

Hydrogen Nuclear Magnetic Resonance Spectrum ($CDCl_3$, ppm):

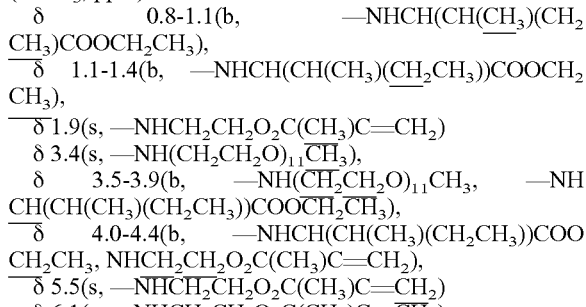

Phosphorus Nuclear Magnetic Resonance Spectrum ($CDCl_3$, ppm): δ 18.6

Average molecular weight ($M_w$): 45000

Example 2

Preparation of [(isoleucine ethyl ester)(aminomethoxypolyethylene glycol 550)(aminoethylmethacrylate)phosphazene], $[NP(IleOEt)_{1.21}(AMPEG550)_{0.57}(AEMA)_{0.21}]_n$ Poly(dichlorophosphazene) (2.00 g, 17.26 mmol), isoleucine ethyl ester (4.09 g, 20.88 mmol), aminomethoxypolyethylene glycol (13.53 g, 24.60 mmol) having the molecular weight of 550, aminoethylmethacrylate hydrochloride salt (1.20 g, 7.25 mmol), triethylamine (16.01 g, 158.19 mmol), and tetrahydrofurane (200 ml) were used according to the same method as Example 1, to produce the final product $[NP(IleOEt)_{1.21}(AMPEG550)_{0.57}(AEMA)_{0.21}]_n$ 9.44 g (yield 78%).

Hydrogen Nuclear Magnetic Resonance Spectrum ($CDCl_3$, ppm):

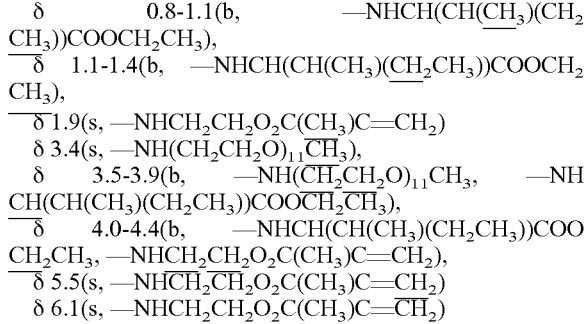

Phosphorus Nuclear Magnetic Resonance Spectrum (CDCl$_3$, ppm): δ 17.9
Average molecular weight (M$_w$): 102000

Example 3

Preparation of poly[(isoleucine ethyl ester)(aminomethoxypolyethylene glycol 550)(aminoethylmethacrylate)phosphazene], [NP(IleOEt)$_{1.23}$(AMPEG550)$_{0.61}$(AEMA)$_{0.15}$]$_n$ Poly(dichlorophosphazene) (2.00 g, 17.26 mmol), isoleucine ethyl ester (4.15 g, 21.23 mmol), aminomethoxypolyethylene glycol (14.48 g, 26.32 mmol) having the molecular weight of 550, aminoethylmethacrylate hydrochloride salt (0.86 g, 5.18 mmol), triethylamine (16.01 g, 158.19 mmol), and tetrahydrofurane (200 ml) were used according to the same method as Example 1, to produce the final product [NP(IleOEt)$_{1.23}$(AMPEG550)$_{0.61}$(AEMA)$_{0.15}$]$_n$ 9.77 g (yield 79%).
Hydrogen Nuclear Magnetic Resonance Spectrum (CDCl$_3$, ppm):
δ 0.8-1.1(b, —NHCH(CH(C$\underline{H_3}$)(CH$_2$CH$_3$))COOCH$_2$CH$_3$),
δ 1.1-1.4(b, —NHCH(CH(CH$_3$)(C$\underline{H_2}$CH$_3$))COOCH$_2$CH$_3$),
δ 1.9(s, —NHCH$_2$CH$_2$O$_2$C(C$\underline{H_3}$)C=CH$_2$)
δ 3.4(s, —NH(CH$_2$CH$_2$O)$_{11}$C$\underline{H_3}$),
δ 3.5-3.9(b, —NH(C$\underline{H_2}$CH$_2$O)$_{11}$CH$_3$, —NHCH(CH(CH$_3$)(CH$_2$CH$_3$))COOC$\underline{H_2}$CH$_3$),
δ 4.0-4.4(b, —NHCH(CH(CH$_3$)(CH$_2$CH$_3$))COOCH$_2$CH$_3$, —NHC$\underline{H_2}$CH$_2$O$_2$C(CH$_3$)C=CH$_2$),
δ 5.5(s, —NHCH$_2$CH$_2$O$_2$C(CH$_3$)C=C$\underline{H_2}$)
δ 6.1(s, —NHCH$_2$CH$_2$O$_2$C(CH$_3$)C=C$\underline{H_2}$)
Phosphorus Nuclear Magnetic Resonance Spectrum (CDCl$_3$, ppm): δ 19.9
Average molecular weight (M$_w$): 132000

Example 4

Preparation of poly[(isoleucine ethyl ester)(aminomethoxypolyethylene glycol 550)(aminoethylmethacrylate)phosphazene], [NP(IleOEt)$_{1.17}$(AMPEG550)$_{0.68}$(AEMA)$_{0.14}$]$_n$ Poly(dichlorophosphazene) (2.00 g, 17.26 mmol), isoleucine ethyl ester (3.94 g, 20.19 mmol), aminomethoxypolyethylene glycol (16.14 g, 29.34 mmol) having the molecular weight of 550, aminoethylmethacrylate hydrochloride salt (0.80 g, 4.83 mmol), triethylamine (16.50 g, 163.08 mmol), and tetrahydrofurane (200 ml) were used according to the same method as Example 1, to produce the final product [NP(IleOEt)$_{1.17}$(AMPEG550)$_{0.68}$(AEMA)$_{0.14}$]$_n$ 10.11 g (yield 79%).
Hydrogen Nuclear Magnetic Resonance Spectrum (CDCl$_3$, ppm):
δ 0.8-1.1(b, —NHCH(CH(C$\underline{H_3}$)(CH$_2$CH$_3$))COOCH$_2$CH$_3$),
δ 1.1-1.4(b, —NHCH(CH(CH$_3$)(C$\underline{H_2}$CH$_3$))COOCH$_2$CH$_3$),
δ 1.9(s, —NHCH$_2$CH$_2$O$_2$C(C$\underline{H_3}$)C=CH$_2$)
δ 3.4(s, —NH(CH$_2$CH$_2$O)$_{11}$C$\underline{H_3}$),
δ 3.5-3.9(b, —NH(C$\underline{H_2}$CH$_2$O)$_{11}$CH$_3$, —NHCH(CH(CH$_3$)(CH$_2$CH$_3$))COOC$\underline{H_2}$CH$_3$),
δ 4.0-4.4(b, —NHCH(CH(CH$_3$)(CH$_2$CH$_3$))COOCH$_2$CH$_3$, —NHC$\underline{H_2}$CH$_2$O$_2$C(CH$_3$)C=CH$_2$),
δ 5.5(s, —NHCH$_2$CH$_2$O$_2$C(CH$_3$)C=C$\underline{H_2}$)
δ 6.1(s, —NHCH$_2$CH$_2$O$_2$C(CH$_3$)C=C$\underline{H_2}$)
Phosphorus Nuclear Magnetic Resonance Spectrum (CDCl$_3$, ppm): δ 19.8
Average molecular weight (M$_w$): 287000

Example 5

Preparation pf poly[(isoleucine ethyl ester)(aminomethoxypolyethylene glycol 750)(aminoethylmethacrylate)phosphazene], [NP(IleOEt)$_{1.17}$(AMPEG750)$_{0.55}$(AEMA)$_{0.28}$]$_n$ Poly(dichlorophosphazene) (2.00 g, 17.26 mmol), isoleucine ethyl ester (3.95 g, 20.19 mmol), aminomethoxypolyethylene glycol (17.80 g, 23.73 mmol) having the molecular weight of 750, aminoethylmethacrylate hydrochloride salt (1.60 g, 9.67 mmol), triethylamine (16.27 g, 160.77 mmol), and tetrahydrofurane (200 ml) were used according to the same method as Example 1, to produce the final product [NP(IleOEt)$_{1.17}$(AMPEG750)$_{0.55}$(AEMA)$_{0.28}$]$_n$ 11.23 g (yield 81%).
Hydrogen Nuclear Magnetic Resonance Spectrum (CDCl$_3$, ppm):
δ 0.8-1.1(b, —NHCH(CH(C$\underline{H_3}$)(CH$_2$CH$_3$))COOCH$_2$CH$_3$),
δ 1.1-1.4(b, —NHCH(CH(CH$_3$)(C$\underline{H_2}$CH$_3$))COOCH$_2$CH$_3$),
δ 1.9(s, —NHCH$_2$CH$_2$O$_2$C(C$\underline{H_3}$)C=CH$_2$)
δ 3.4(s, —NH(CH$_2$CH$_2$O)$_{15}$C$\underline{H_3}$),
δ 3.5-3.9(b, —NH(C$\underline{H_2}$CH$_2$O)$_{15}$CH$_3$, —NHCH(CH(CH$_3$)(CH$_2$CH$_3$))COOC$\underline{H_2}$CH$_3$),
δ 4.0-4.4(b, —NHCH(CH(CH$_3$)(CH$_2$CH$_3$))COOCH$_2$CH$_3$, —NHCH$_2$CH$_2$O$_2$C(CH$_3$)O=CH$_2$),
δ 5.5(s, —NHCH$_2$CH$_2$O$_2$C(CH$_3$)C=C$\underline{H_2}$)
δ 6.1(s, —NHCH$_2$CH$_2$O$_2$C(CH$_3$)C=C$\underline{H_2}$)
Phosphorus Nuclear Magnetic Resonance Spectrum (CDCl$_3$, ppm): δ 18.9
Average molecular weight (M$_w$): 185000

Example 6

Preparation of poly[(isoleucine ethyl ester)(aminomethoxypolyethylene glycol 550)(hydroxyethylmethacrylate)phosphazene], [NP(IleOEt)$_{1.23}$(AMPEG550)$_{0.61}$(HEMA)$_{0.15}$]$_n$ Poly(dichlorophosphazene) (2.00 g, 17.26 mmol), isoleucine ethyl ester hydrochloride salt (4.15 g, 21.23 mmol), hydroxyethylmethacrylate (0.86 g, 5.18 mmol), aminomethoxypolyethylene glycol (14.48 g, 26.32 mmol) having the molecular weight of 550 (14.48 g, 26.32 mmol), triethylamine (16.01 g, 158.19 mmol), and tetrahydrofurane (400 ml) were used according to the same method as Example 1, to produce the final product [NP(IleOEt)$_{1.10}$(AMPEG550)$_{0.61}$(HEMA)$_{0.15}$]$_n$ 9.53 g (yield 77%).
Hydrogen Nuclear Magnetic Resonance Spectrum (CDCl$_3$, ppm):
δ 0.8-1.1(b, —NHCH(CH(C$\underline{H_3}$)(CH$_2$CH$_3$))COOCH$_2$CH$_3$),
δ 1.1-1.4(b, —NHCH(CH(CH$_3$)(C$\underline{H_2}$CH$_3$))COOCH$_2$CH$_3$),
δ 1.9(s, —OCH$_2$CH$_2$O$_2$C(C$\underline{H_3}$)C=CH$_2$)
δ 3.4(s, —NH(CH$_2$CH$_2$O)$_{11}$C$\underline{H_3}$),
δ 3.5-3.9(b, —NH(C$\underline{H_2}$CH$_2$O)$_{11}$CH$_3$, —NHC$\underline{H}$(CH(CH$_3$)(CH$_2$CH$_3$))COOC$\underline{H_2}$CH$_3$), δ 4.0-4.4(b, —NHCH(CH(CH$_3$)(CH$_2$CH$_3$))COOCH$_2$CH$_3$, —OCH$_2$CH$_2$O$_2$C(CH$_3$)C=CH$_2$),
δ 5.4(s, —OCH$_2$CH$_2$O$_2$C(CH$_3$)C=$\overline{CH_2}$)
δ 6.0(s, —OCH$_2$CH$_2$O$_2$C(CH$_3$)C=$\overline{CH_2}$)
Phosphorus Nuclear Magnetic Resonance Spectrum (CDCl$_3$, ppm): δ 20.4
Average molecular weight (M$_w$): 91800

Example 7

Preparation of poly[(isoleucine ethyl ester)(aminomethoxypolyethylene glycol 750)(hydroxyethylmethacrylate)phosphazene], [NP(IleOEt)$_{1.04}$(AMPEG750)$_{0.74}$(HEMA)$_{0.22}$]$_n$ Poly(dichlorophosphazene) (2.00 g, 17.26 mmol), isoleucine ethyl ester hydrochloride salt (4.09 g, 20.88 mmol), hydroxyethylmethacrylate (0.29 g, 1.73 mmol), aminomethoxypolyethylene glycol (23.95 g, 31.93 mmol) having the molecular weight of 750, triethylamine (16.56 g, 163.62 mmol), and tetrahydrofurane (400 ml) were used according to the same method as Example 1, to produce the final product [NP(IleOEt)$_{1.04}$(AMPEG750)$_{0.74}$(HEMA)$_{0.22}$]$_n$ 12.18 g (yield 77%).
Hydrogen Nuclear Magnetic Resonance Spectrum (CDCl$_3$, ppm):
δ 0.8-1.1(b, —NHCH(CH($\underline{CH_3}$)(CH$_2$CH$_3$))COOCH$_2$CH$_3$),
δ 1.1-1.4(b, —NHCH(CH(CH$_3$)($\underline{CH_2CH_3}$))COOCH$_2$CH$_3$),
δ 1.9(s, —OCH$_2$CH$_2$O$_2$C(CH$_3$)C=CH$_2$)
δ 3.4(s, —NH(CH$_2$CH$_2$O)$_{15}$$\underline{CH_3}$),
δ 3.5-3.9(b, —NH($\overline{CH_2}$CH$_2$O)$_{15}$CH$_3$, —NHCH(CH(CH$_3$)(CH$_2$CH$_3$))COO$\overline{CH_2}$$\overline{CH_3}$),
δ 4.0-4.4(b, —NHCH(CH(CH$_3$)(CH$_2$CH$_3$))COOCH$_2$CH$_3$, —OCH$_2$CH$_2$O$_2$C(CH$_3$)C=CH$_2$),
δ 5.4(s, —O$\overline{CH_2}$$\overline{CH_2}$O$_2$C(CH$_3$)C=CH$_2$)
δ 6.0(s, —OCH$_2$CH$_2$O$_2$C(CH$_3$)C=$\overline{CH_2}$)
Phosphorus Nuclear Magnetic Resonance Spectrum (CDCl$_3$, ppm): δ 18.1
Average molecular weight (M$_w$): 101200

Example 8

Preparation of poly[(isoleucine ethyl ester)(aminomethoxypolyethylene glycol 550)(glycylglycine)(glycylglycylaminoethylmethacrylate)phosphazene], [NP(IleOEt)$_{1.27}$(AMPEG550)$_{0.51}$(GlyGlyOH)$_{0.09}$(GlyGlyAEMA)$_{0.13}$]$_n$ Dried isoleucine ethyl ester hydrochloride salt (4.29 g, 21.92 mmol) was dissolved in 100 ml of anhydrous tetrahydrofuran, and then, triethylamine (6.65 g, 65.76 mmol) was added thereto. Poly(dichlorophosphazene) (2.00 g, 17.26 mmol) dissolved in 50 and of anhydrous tetrahydrofuran was added dropwise to the obtained dried isoleucine ethyl ester hydrochloride salt solution in dry ice-acetone bath at −60° C., allowing to react for 48 hours with slowly increasing the temperature to the room temperature.

After checking the reaction progress by checking $^{31}$P-NMR, a solution of dried glycylglycineallylester trifluoro acetic acid salt (2.17 g, 7.59 mmol) dissolved in 50 ml of anhydrous tetrahydrofuran, to which triethylamine (2.30 g, 22.77 mmol) was added, was added to the obtained reaction solution, allowing to react for 8 hours. After checking again the reaction progress by checking $^{31}$P-NMR, a solution of dried aminomethoxypolyethylene glycol (12.10 g, 22.01 mmol) having the molecular weight of 550 dissolved in anhydrous tetrahydrofuran (50 ml) was added dropwise to the obtained resulting product, allowing to react at the room temperature for 12 hours, and at 40-50° C. for 24 hours.

The reaction solution was filtered to remove a generated triethylamine hydrochloride salt. The remaining solution was concentrated under decompression until the solvent was mostly removed. The obtained concentrate solution was dissolved in tetrahydrofuran (10 ml) and an excess of hexane was added thereto to induce the formation of precipitation. After the process was repeated 2 or 3 times, the obtained precipitate was dissolved again in a small amount of methylalcohol. The resulting solution was put into an MWCO 12000 membrane (Spectrum Laboratories, Inc.), and dialyzed with methylalcohol at room temperature for 5 days and with distilled water for 5 days. The obtained product was dried at a low temperature, to produce poly(dichlorophosphazene), [NP(IleOEt)$_{1.27}$(AMPEG550)$_{0.51}$(GlyGlyOAll)$_{0.22}$]$_n$ (14.21 g).

The obtained [NP(IleOEt)$_{1.27}$(AMPEG550)$_{0.51}$(GlyGlyOAl)$_{0.22}$]$_n$ (14.21 g) was dissolved in anhydrous tetrahydrofuran (200 ml), and reacted with 15 mol % tetrakistriphenylphosphinpalladium(0) (0.56 g) and 20 equivalents of morpholine (4.23 g) at the room temperature for 8 hours. The remaining solution was concentrated under decompression, and dissolved in a small amount of methylalcohol. The resulting solution was put into an MWCO 6-8000 membrane (Spectrum Laboratories, Inc.), and dialyzed with methylalcohol at room temperature for 5 days and with distilled water at 4° C. for 5 days. The obtained product was dried at a low temperature, to produce intermediate product [NP(IleOEt)$_{1.27}$(AMPEG550)$_{0.51}$(GlyGlyOH)$_{0.22}$]$_n$ (13.78 g).

The obtained [NP(IleOEt)$_{1.27}$(AMPEG550)$_{0.51}$(GlyGlyOH)$_{0.22}$]$_n$ (13.78 g) dissolved in anhydrous dichloromethane (100 ml), and 0.26 equivalents of aminoethylmethacrylate (0.39 g in dimethylformamide), 0.52 equivalents of dicyclohexylcarbodiimide (0.16 g), and 0.52 equivalents of dimethylaminopyridine (0.10 g) were added thereto, allowing to react at 0° C. for 24. The resulting solution was put into an MWCO 6-8000 membrane (Spectrum Laboratories, Inc.), and dialyzed with methylalcohol at room temperature for 5 days and with distilled water at 4° C. for 5 days. The obtained product was dried at a low temperature, to produce final product [NP(IleOEt)$_{1.27}$(AMPEG550)$_{0.51}$(GlyGlyOH)$_{0.09}$(GlyGlyAEMA)$_{0.13}$]$_n$ 13.02 g (yield 89%)
Hydrogen Nuclear Magnetic Resonance Spectrum (CDCl$_3$, ppm):
δ 0.8-1.1(b, —NHCH(CH($\underline{CH_3}$)(CH$_2$CH$_3$))COOCH$_2$CH$_3$),
δ 1.1-1.4(b, —NHCH(CH(CH$_3$)($\underline{CH_2CH_3}$))COOCH$_2$CH$_3$),
δ 1.9(s, —NHCH$_2$CONHCH$_2$CONHCH$_2$CH$_2$O$_2$C($\underline{CH_3}$)C=CH$_2$)
δ 3.4(s, —NH(CH$_2$CH$_2$O)$_{11}$CH$_3$),
δ 3.5-3.9(b, —NH($\overline{CH_2}$CH$_2$O)$_{11}$CH$_3$, —NHCH(CH(CH$_3$)(CH$_2$CH$_3$))COO$\overline{CH_2}$$\overline{CH_3}$),
δ 4.0-4.4(b, —NHCH(CH(CH$_3$)(CH$_2$CH$_3$))COOCH$_2$CH$_3$, —OCH$_2$CH$_2$O$_2$C(CH$_3$)C=CH$_2$),
δ 5.5(s, —$\overline{NH}$$\overline{CH_2}$CONHCH$_2$CONHCH$_2$CH$_2$O$_2$C(CH$_3$)C=CH$_2$)
δ $\overline{6.1}$(s, —NHCH$_2$CONHCH$_2$CONHCH$_2$CH$_2$O$_2$C(CH$_3$)C=CH$_2$)
Phosphorus Nuclear Magnetic Resonance Spectrum (CDCl$_3$, ppm): δ 18.4
Average molecular weight (M$_w$): 169200

Example 9

Preparation of poly[(isoleucine ethyl ester)(aminomethoxypolyethylene glycol 550)(glycylglycine)(glycylglycylhydroxyethylmethacrylate)phosphazene], [NP(IleOEt)$_{1.29}$(AMPEG550)$_{0.54}$(GlyGlyOH)$_{0.02}$(GlyGlyHEMA)$_{0.15}$]$_n$ Poly(dichlorophosphazene) (2.00 g, 17.26 mmol), isoleucine ethyl ester (4.36 g, 22.27 mmol), glycylglycineallylester trifluoro acetic acid salt (1.68 g, 5.87 mmol), aminomethoxypolyethylene glycol (12.82 g, 23.30 mmol) having the molecular weight of 550, tetrakistriphenylphosphinpalladium(0) (0.77 g, 0.59 mmol), morpholine (5.11 g, 58.68 mmol), hydroxyethylmethacrylate (1.12 g, 6.70 mmol), dicyclohexylcarbodiimide (1.38 g, 6.70 mmol), dimethylaminopyridine (0.82 g, 6.70 mmol), triethylamine (15.62 g, 154.32 mmol), and tetrahydrofurane (550 ml), dichloromethane (100 ml) were used according to the same method as Example 8, to produce final product [NP(IleOEt)$_{1.29}$(AMPEG550)$_{0.54}$(GlyGlyOH)$_{0.02}$(GlyGlyHEMA)$_{0.15}$]$_n$ 9.49 g (yield 77%).

Hydrogen Nuclear Magnetic Resonance Spectrum (CDCl$_3$, ppm):
δ 0.8-1.1(b, —NHCH(CH(C$\underline{H}_3$)(CH$_2$CH$_3$))COOCH$_2$CH$_3$),
δ 1.1-1.4(b, —NHCH(CH(CH$_3$)(C$\underline{H}_2$CH$_3$))COOCH$_2$CH$_3$),
δ 1.9(s, —NHCH$_2$CONHCH$_2$CO$_2$CH$_2$CH$_2$O$_2$C(C$\underline{H}_3$)C=CH$_2$)
δ 3.4(s, —NH(CH$_2$C$\underline{H_2O})_{11}$CH$_3$),
δ 3.5-3.9(b, —NH(C$\underline{H}_2$CH2O)$_{11}$CH$_3$, —NHCH(CH(CH$_3$)(CH$_2$CH$_3$))COOC$\underline{H}_2$CH$_3$),
δ 4.0-4.4(b, —NHCH(CH(CH$_3$)(CH$_2$CH$_3$))COOCH$_2$CH$_3$, —OCH$_2$CH$_2$O$_2$C(CH$_3$)C=CH$_2$),
δ 5.4(s, —N$\overline{H}$CH$_2$CONHCH$_2$CO$_2$CH$_2$CH$_2$O$_2$C(CH$_3$)C=CH$_2$)
δ 6.0(s, —NHCH$_2$CONHCH$_2$CO$_2$CH$_2$CH$_2$O$_2$C(CH$_3$)C=CH$_2$)

Phosphorus Nuclear Magnetic Resonance Spectrum (CDCl$_3$, ppm): δ 19.4

Average molecular weight (M$_w$): 366900

Example 10

Preparation of poly[(isoleucine ethyl ester)(aminomethoxypolyethylene glycol 550)(cysteine ethyl ester)phosphazene], [NP(IleOEt)$_{1.21}$(AMPEG550)$_{0.64}$(CysOEt)$_{0.15}$]$_n$ Poly(dichlorophosphazene) (2.00 g, 17.26 mmol), isoleucine ethyl ester (4.09 g, 20.88 mmol), benzyloxycarbonylcystine ethyl ester (1.66 g, 5.18 mmol), aminomethoxypolyethylene glycol (15.19 g, 27.62 mmol) having the molecular weight of 550, triethylamine (16.30 g, 161.04 mmol), and tetrahydrofurane (550 ml) were used according to the same method as Example 1, to produce [NP(IleOEt)$_{1.21}$(AMPEG550)$_{0.64}$(ChzCysOEt)$_{0.15}$]n 14.19 g.

The obtained [NP(IleOEt)$_{1.21}$(AMPEG550)$_{0.64}$(CbzCysOEt)$_{0.15}$]$_n$ (14.19 g) dissolved in ethylalcohol (200 ml), and then, 50 wt % palladium/charcoal (8.4 g) was added thereto, allowing to react at the room temperature for 12 hours in the presence of hydrogen gas of 60-70 psi pressure. The reaction solution was filtrated. The remaining solution was concentrated under decompression, and dissolved in a small amount of methylalcohol. The resulting solution was dialyzed with methylalcohol at room temperature for 5 days and with distilled water at 4° C. for 5 days. The obtained product was dried at a low temperature, to produce fmal product [NP(IleOEt)$_{1.21}$(AMPEG550)$_{0.64}$(CysOEt)$_{0.15}$]$_n$ 9.23 g (yield 73%).

Hydrogen Nuclear Magnetic Resonance Spectrum (CDCl$_3$, ppm):
δ 1.1-1.4(b, —NHCH(CH(CH$_3$)(C$\underline{H}_2$CH$_3$))COOCH$_2$CH$_3$, —NHCH(CH$_2$SH)(COOC$\underline{H}_2$CH$_3$)),
δ 3.0-3.3(b, —NHCH(CH$_2$SH)(C$\overline{OO}$CH$_2$CH$_3$)),
δ 3.4(s, —NH(CH$_2$C$\underline{H_2O})_{11}$CH$_3$),
δ 3.5-3.9(b, —NH(C$\overline{H}_2$CH$_2$O)$_{11}$CH$_3$, —NHCH(CH$_2$SH)(COOCH$_2$CH$_3$)),
δ 4.0-4.4(b, —NHCH(CH(CH$_3$)(CH$_2$CH$_3$))COOCH$_2$CH$_3$, —NHCH(CH$_2$SH)(C$\overline{OO}$CH$_2$CH$_3$))

Phosphorus Nuclear Magnetic Resonance Spectrum (CDCl$_3$, ppm): δ 20.1

Average molecular weight (M$_w$): 264000

Example 11

Preparation of poly[(isoleucine ethyl ester)(aminomethoxypolyethylene glycol 550)(cystine ethyl ester)phosphazene], [NP(IleOEt)$_{0.96}$(AMPEG550)$_{0.78}$(CysOEt)$_{0.24}$]$_n$ Poly(dichlorophosphazene) (2.00 g, 17.26 mmol), isoleucine ethyl ester (3.25 g, 16.57 mmol), benzyloxycarbonylcystine ethyl ester (2.66 g, 8.29 mmol), aminomethoxypolyethylene glycol (18.51 g, 33.66 mmol) having the molecular weight of 550, 50 wt % palladium/charcoal (13.44 g), triethylamine (17.77 g, 175.56 mmol), and tetrahydrofurane (550 ml) were used according to the same method as Example 1, to produce final product [NP(IleOEt)$_{0.96}$(AMPEG550)$_{0.78}$(CysOEt)$_{0.24}$]$_n$ 8.88 g (yield 74%).

Hydrogen Nuclear Magnetic Resonance Spectrum (CDCl$_3$, ppm):
δ 0.8-1.1(b, —NHCH(CH(C$\underline{H}_3$)(CH$_2$CH$_3$))COOCH$_2$CH$_3$),
δ 1.1-1.4(b, —NHCH(CH(CH$_3$)(C$\underline{H}_2$CH$_3$))COOCH$_2$CH$_3$,—NHCH(CH$_2$SH)(COOC$\underline{H}_2$CH$_3$)),
δ 3.0-3.3(b, —NHCH(CH$_2$SH)(C$\overline{OO}$CH$_2$CH$_3$)),
δ 3.4(s, —NH(CH$_2$C$\underline{H_2O})_{11}$CH$_3$),
δ 3.5-3.9(b, —NH(C$\overline{H}_2$CH$_2$O)$_{11}$CH$_3$, —NHCH(CH$_2$SH)(COOCH$_2$CH$_3$)),
δ 4.0-4.4(b, —NHCH(CH(CH$_3$)(CH$_2$CH$_3$))COOCH$_2$CH$_3$, —NHCH(CH$_2$SH)(C$\overline{OO}$CH$_2$CH$_3$))

Phosphorus Nuclear Magnetic Resonance Spectrum (CDCl$_3$, ppm): δ 19.3

Average molecular weight (M$_w$): 423700

Example 12

Preparation of poly[(isoleucine ethyl ester)(aminomethoxypolyethylene glycol 750)(cystine ethyl ester)phosphazene], [NP(IleOEt)$_{1.02}$(AMPEG750)$_{0.43}$(CysOEt)$_{0.54}$]$_n$ Poly(dichlorophosphazene) (2.00 g, 17.26 mmol), isoleucine ethyl ester (3.45 g, 17.61 mmol), cystinediethylester hydrochloride salt (6.88 g, 18.64 mmol), aminomethoxypolyethylene glycol (13.92 g, 18.55 mmol) having the molecular weight of 750, triethylamine (16.63 g, 164.4 mmol), and tetrahydrofurane (550 ml) were used according to the same method as Example 1, to produce [NP(IleOEt)$_{1.21}$(AMPEG750)$_{0.64}$(CysDiOEt)$_{0.15}$]$_n$ 11.86 g.

The obtained [NP(IleOEt)$_{1.21}$(AMPEG750)$_{0.64}$(Cys-DiOEt)$_{0.15}$]$_n$ (11.86 dissolved in distilled water (200 ml), and a disulfide inhibitor, dithioerythritol (1.44 g) was added thereto. The pH of the reaction solution was adjusted to pH 8.5 by adding 1 M sodium hydroxide aqueous solution, allowing to react for 24 hours, to produce [NP(IleOEt)$_{1.02}$(AMPEG750)$_{1.02}$(CysOEt)$_{0.54}$]$_n$ 14.00 g (yield 83%).

Hydrogen Nuclear Magnetic Resonance Spectrum (CDCl$_3$, ppm):
δ 0.8-1.1(b, —NHCH(CH(C$\underline{H}_3$)(CH$_2$CH$_3$))COOCH$_2$CH$_3$),
δ 1.1-1.4(b, —NHCH(CH(CH$_3$)(C$\underline{H_2CH_3}$))COOCH$_2$CH$_3$),
δ 3.4(s, —NH(CH$_2$CH$_2$O)$_{15}$C$\underline{H_3}$),
δ 3.5-3.9(b, —NH($\underline{CH_2C_2O}$)$_{15}$CH$_3$, —NHCH(CH(CH$_3$)(CH$_2$CH$_3$))COOC$\underline{H_2CH_3}$),
δ 4.0-4.4(b, —NHCH(CH(CH$_3$)(CH$_2$CH$_3$))COOC$\underline{H_2}$CH$_3$)

Phosphorus Nuclear Magnetic Resonance Spectrum (CDCl$_3$, ppm): δ 19.2
Average molecular weight (M$_w$): 131000

Example 13

Preparation of poly[(isoleucine ethyl ester)(aminomethoxypolyethylene glycol 550)(ethyl-2-(O-glycyl)lactate)(cystine ethyl ester)phosphazene], [NP(IleOEt)$_{1.12}$(AMPEG550)$_{0.73}$(GlyLacOEt)$_{0.06}$(CysOEt)$_{0.09}$]$_n$ Poly(dichlorophosphazene) (2.00 g, 17.26 mmol), isoleucine ethyl ester (3.78 g, 19.33 mmol), trityl cysteine (1.13 g, 3.11 mmol), ethyl-2-(O-glycyl)lactate ammonium oxalate (2.85 g, 2.07 mmol), aminomethoxypolyethylene glycol (17.32 g, 31.50 mmol) having the molecular weight of 550, and triethylamine (17.00 g, 168.03 mmol), tetrahydrofurane (550 me) were used according to the same method as Example 1, to produce [NP(IleOEt)$_{1.21}$(AMPEG550)$_{0.73}$(GlyLaCOEt)$_{0.06}$(triCysOEt)$_{0.09}$]$_n$ 12.49 g.

The obtained [NP(IleOEt)$_{1.21}$(AMPEG550)$_{0.73}$(GlyLacOEt)$_{0.06}$(triCysOEt)$_{0.09}$]$_n$ (12.49 g) was dissolved in tetrahydrofurane (200 ml), and then, trifluoroacetic acid (0.35 g) was added thereto, allowing to react for 12 hours. The reaction solution was filtrated. The remaining solution was concentrated under decompression, and dissolved in a small amount of methylalcohol. The resulting solution was dialyzed with methylalcohol at room temperature for 5 days and with distilled water at 4° C. for 5 days. The obtained product was dried at a low temperature, to produce final product [NP(IleOEt)$_{1.21}$(AMPEG550)$_{0.73}$(GlyLacOEt)$_{0.06}$(CysOEt)$_{0.09}$]$_n$ 11.28 g (yield 85%).

Hydrogen Nuclear Magnetic Resonance Spectrum (CDCl$_3$, ppm):
δ 0.8-1.1(b, —NHCH(CH(C$\underline{H_3}$)(CH$_2$CH$_3$))COOCH$_2$CH$_3$),
δ 1.1-1.4(b, —NHCH(CH(CH$_3$)(C$\underline{H_2CH_3}$))COOCH$_2$CH$_3$,—NHCH2COOCH(CH$_3$)(COOC$\underline{H_2CH_3}$), —NHCH(C$\underline{H_2SH}$)(COOCH$_2$CH$_3$)),
δ 3.0-3.3(b, —NH$\underline{CH}$(CH$_2$SH)(COOCH$_2$CH$_3$)),
δ 3.4(s, —NH(CH$_2$C$\underline{H_2O)}_{11}$CH$_3$),
δ 3.5-3.9(b, —NH($\underline{CH_2}$CH$_2$O)$_{11}$CH$_3$, —NHCH(CH$_2$SH)(COOCH$_2$CH$_3$)),
δ 4.0-4.4(b, —NHCH(CH(CH$_3$)(CH$_2$CH$_3$))COOC$\underline{H_2}$CH$_3$, —NHCH$_2\overline{C}$OOCH(CH$_3$)(COOCH$_2$CH$_3$) —NHCH(CH$_2$SH)(COOC$\underline{H_2}$CH$_3$))
δ 5.1(s, —NHCH2COO$\underline{CH}$(CH$_3$)(COOCH$_2$CH$_3$)

Phosphorus Nuclear Magnetic Resonance Spectrum (CDCl$_3$, ppm): δ 19.8
Average molecular weight (M$_w$): 238000

Example 14

Preparation of poly[(isolencine ethyl ester)(aminomethoxypolyethylene glycol 550)(ethyl-2-(O-glycyl)lactate)(glycylcystine ethyl ester)phosphazene], [NP(IleOEt)$_{1.15}$(AMPEG550)$_{0.60}$(GlyLacOEt)$_{0.09}$(GlyCysOEt)$_{0.16}$]$_n$ Poly(dichlorophosphazene) (2.00 g, 17.26 mmol), isoleucine ethyl ester (3.88 g, 19.85 mmol), glycineallylester trifluoro acetic acid salt (1.68 g, 5.87 mmol), aminomethoxypolyethylene glycol (14.24 g, 25.89 mmol) having the molecular weight of 550, tetrakistriphenylphosphinpalladium(0) (0.68 g, 0.59 mmol), morpholine (5.11 g, 58.7 mmol), cystine ethyl ester (1.03 g, 5.52 mmol), 1-ethyl-3-(3-dimethylaminopropyl)carbodiimide hydrochloride salt (2.12 g, 11.04 mmol), triethylamine (17.34 g, 171.39 mmol), and tetrahydrofurane (550 ml), dichloromethane (100 ml) were used according to the same method as Example 8, to produce final product [NP(IleOEt)$_{1.15}$(AMPEG550)$_{0.60}$(GlyLacOEt)$_{0.09}$(GlyCysOEt)$_{0.16}$]$_n$ 9.14 g (yield 79%).

Hydrogen Nuclear Magnetic Resonance Spectrum (CDCl$_3$, ppm):
δ 0.8-1.1(b, —NHCH(CH(C$\underline{H_3}$)(CH$_2$CH$_3$))COOCH$_2$CH$_3$),
δ 1.1-1.4(b, —NHCH(CH(CH$_3$)(C$\underline{H_2CH_3}$))COOCH$_2$CH$_3$, —NHCH2COOCH(C$\underline{H_3}$)(COOCH$_2$CH$_3$), —NHCH$_2$CONHCH(CH$_2$SH)(COOC$\underline{H_2}$CH$_3$)),
δ 2.3(s, —NHCH$_2$CONHCH(CH$_2$SH)($\overline{C}$OOCH$_2$CH$_3$))
δ 3.0(s, —NHCH$_2$CONHCH(C$\overline{H_2}$SH)(COOCH$_2$CH$_3$))
δ 3.4(s, —NH(CH$_2$CH$_2$O)$_{11}$C$\underline{H_3}$),
δ 3.5-3.9(b, —NH($\overline{CH_2}$CH$_2$O)$_{11}$CH$_3$, —NHCH$_2$CONHCH(CH$_2$SH)(COOC$\underline{H_2CH_3}$)
δ 4.0-4.4(b, —NHCH(CH(CH$_3$)(CH$_2$CH$_3$))COOC$\underline{H_2}$CH$_3$) —NHCH2$\overline{C}$OOCH(CH$_3$)(COOCH$_2$CH$_3$) —NHCH$_2$CONHCH(C$\underline{H_2SH}$)(COOCH$_2$CH$_3$))
δ 5.1(s, —NHCH2COOCH(CH$_3$)($\overline{C}$OOCH$_2$CH$_3$)

Phosphorus Nuclear Magnetic Resonance Spectrum (CDCl$_3$, ppm): δ 19.7
Average molecular weight (M$_w$): 238000

Example 15

Preparation of poly[(isoleucine ethyl ester)(aminomethoxypolyethylene glycol 550)(glycylglycine)(glycylglycylcystine ethyl ester)phosphazene], [NP(IleOEt)$_{1.19}$(AMPEG550)$_{0.64}$(GlyGlyOH)$_{0.05}$(GlyGlyCysOEt)$_{0.12}$]$_n$ Poly(dichlorophosphazene) (2.00 g, 17.26 mmol), isoleucine ethyl ester (4.36 g, 22.27 mmol), glycylglycineallylester trifluoro acetic acid salt (1.68 g, 5.87 mmol), aminomethoxypolyethylene glycol (15.19 g, 27.62 mmol) having the molecular weight of 550, tetrakistriphenylphosphinpalladium(0) (0.77 g, 0.59 mmol), morpholine (5.11 g, 58.68 mmol), cystine ethyl ester (0.40 g, 4.14 mmol), dicyclohexylcarbodiimide (0.85 g, 4.14 mmol), dimethylaminopyridine (0.51 g, 4.14 mmol), triethylamine (15.62 g, 154.32 mmol), tetrahydrofurane (550 ml), and dichloromethane (100 ml) were used according to the same method as Example 8, to produce final product [NP(IleOEt)$_{1.19}$(AMPEG550)$_{0.64}$(GlyGlyOH)$_{0.05}$(GlyGlyCysOEt)$_{0.12}$]$_n$ 10.75 g (yield 81%).

Hydrogen Nuclear Magnetic Resonance Spectrum (CDCl$_3$, ppm):

δ 0.8-1.1(b, —NHCH(CH(CH$_3$)(CH$_2$CH$_3$))COOCH$_2$CH$_3$),

δ 1.1-1.4(b, —NHCH(CH(CH$_3$)(CH$_2$CH$_3$))COOCH$_2$CH$_3$, —NHCH$_2$CONHCH$_2$CONHCH(CH$_2$SH)(COOCH$_2$CH$_3$)),

δ 2.3(s, —NHCH$_2$CONHCH$_2$CONHCH(CH$_2$SH)(COOCH$_2$CH$_3$))

δ 3.0(s, —NHCH$_2$CONHCH$_2$CONHCH(CH$_2$SH)(COOCH$_2$CH$_3$))

δ 3.4(s, —NH(CH$_2$CH$_2$O)$_{11}$CH$_3$),

δ 3.5-3.9(b, —NH(CH$_2$CH$_2$O)$_{11}$CH$_3$, —NHCH$_2$CONHCH$_2$CONHCH(CH$_2$SH)(COOCH$_2$CH$_3$)),

δ 4.0-4.4(b, —NHCH(CH(CH$_3$)(CH$_2$CH$_3$))COOCH$_2$CH$_3$, —NHCH$_2$CONHCH$_2$CONHCH(CH$_2$SH)(COOCH$_2$CH$_3$))

Phosphorus Nuclear Magnetic Resonance Spectrum (CDCl$_3$, ppm): δ 19.8

Average molecular weight (M$_w$): 129000

Example 16

Preparation of poly[(isoleucine ethyl ester)(aminomethoxypolyethylene glycol 550)(cysteamine) phosphazene], [NP(IleOEt)$_{1.18}$(AMPEG550)$_{0.62}$(cysteamine)$_{0.02}$]$_n$ Poly(dichlorophosphazene) (2.00 g, 17.26 mmol), isoleucine ethyl ester (3.99 g, 20.37 mmol), aminomethoxypolyethylene glycol (14.71 g, 26.75 mmol) having the molecular weight of 550, cystamine dihydrochloride salt (1.55 g, 6.90 mmol), dithioerythritol (1.06 g, 6.90 mmol), triethylamine (16.40 g, 162.06 mmol), and tetrahydrofurane (550 ml) were used according to the same method as Example 11, to produce final product [NP(IleOEt)$_{1.18}$(AMPEG550)$_{0.62}$(cysteamine)$_{0.20}$]$_n$ 9.81 g (yield 78%).

Hydrogen Nuclear Magnetic Resonance Spectrum (CDCl$_3$, ppm):

δ 0.8-1.1(b, —NHCH(CH(CH$_3$)(CH$_2$CH$_3$))COOCH$_2$CH$_3$),

δ 1.1-1.4(b, —NHCH(CH(CH$_3$)(CH$_2$CH$_3$))COOCH$_2$CH$_3$),

δ 3.4(s, —NH(CH$_2$CH$_2$O)$_{11}$CH$_3$),

δ 3.5-3.9(b, —NH(CH$_2$CH$_2$O)$_{11}$CH$_3$, —NHCH(CH(CH$_3$)(CH$_2$CH$_3$))COOCH$_2$CH$_3$),

δ 4.0-4.4(b, —NHCH(CH(CH$_3$)(CH$_2$CH$_3$))COOCH$_2$CH$_3$)

Phosphorus Nuclear Magnetic Resonance Spectrum (CDCl$_3$, ppm): δ 20.1

Average molecular weight (M$_w$): 217000

Example 17

Preparation of poly[(isoleucine ethyl ester)(aminomethoxypolyethylene glycol 550)(glycylglycine)(glycylglycylcysteamine)phosphazene], [NP(IleOEt)$_{1.15}$(AMPEG550)$_{0.67}$(GlyGlyOH)$_{0.05}$(GlyGlycysteamine)$_{0.13}$]$_n$ Poly(dichlorophosphazene) (2.00 g, 17.26 mmol), isoleucine ethyl ester (3.88 g, 19.85 mmol), glycylglycineallylester trifluoro acetic acid salt (1.78 g, 6.21 mmol), aminomethoxypolyethylene glycol (15.90 g, 28.91 mmol) having the molecular weight of 550, tetrakistriphenylphosphinpalladium(0) (0.72 g, 0.62 mmol), morpholine (5.41 g, 62.14 mmol), cysteamine hydrochloride salt (0.51 g, 4.49 mmol), dicyclohexylcarbodiimide (0.93 g, 4.49 mmol), dimethylaminopyridine (0.55 g, 4.49 mmol), triethylamine (16.65 g, 164.58 mmol), and tetrahydrofurane (550 ml), dichloromethane (100 ml) were used according to the same method as Example 8, to produce final product [NP(IleOEt)$_{1.15}$(AMPEG550)$_{0.67}$(GlyGlyOH)$_{0.05}$(GlyGlycysteamine)$_{0.13}$]$_n$ 9.99 g (yield 76%). The cystamine dihydrochloride salt was converted to cystamine by the same method as Example 16.

Hydrogen Nuclear Magnetic Resonance Spectrum (CDCl$_3$, ppm):

δ 0.7 to 1.1(b, —NHCH(CH$_3$)CH$_2$CH$_3$)COOCH$_2$CH$_3$),

δ 1.1 to 1.3(b, —NHCH(CH(CH$_3$)CH$_2$CH$_3$)COOCH$_2$CH),

δ 1.4 to 1.8(b, —NHCH(CH(CH$_3$)CH$_2$CH$_3$)COOCH$_2$CH$_3$),

δ 2.8(b, —NHCH$_2$CONHCH$_2$CONHCH$_2$CH$_2$SH),

δ 3.4(s, —NH(CH$_2$CH$_2$O)$_{11}$CH$_3$),

δ 3.5(b, —NHCH$_2$CONHCH$_2$CONHCH$_2$CH$_2$SH),

δ 3.4 to 3.8(b, —NH(CH$_2$CH$_2$O)$_{11}$CH$_3$),

δ 3.9 to 4.3(b, —NHCH(CH(CH$_3$)CH$_2$CH$_3$)COOCH$_2$CH$_3$, —NHCH$_2$CONHCH$_2$CONHCH$_2$CH$_2$SH)

Phosphorus Nuclear Magnetic Resonance Spectrum (CDCl$_3$, ppm): δ 19.8

Average molecular weight (M$_w$): 312000

Example 18

Preparation of poly[(isoleucine ethyl ester)(aminomethoxypolyethylene glycol 550)(tyramine)phosphazene], [NP(IleOEt)$_{1.14}$(AMPEG550)$_{0.69}$(Tyramine)$_{0.16}$]$_n$ Poly(dichlorophosphazene) (2.00 g, 17.26 mmol), isoleucine ethyl ester (3.04 g, 15.52 mmol), aminomethoxypolyethylene glycol (3.79 g, 6.90 mmol) having the molecular weight of 550, tyramine (3.31 g, 24.14 mmol), triethylamine (17.32 g, 99.14 mmol), and tetrahydrofurane (200 ml), dimethylformamide (50 ml) were used according to the same method as Example 1, to produce final product [NP(IleOEt)$_{1.18}$(AMPEG550)$_{0.62}$(Tyramine)$_{0.20}$]$_n$ 9.81 g (yield 78%).

Hydrogen Nuclear Magnetic Resonance Spectrum (CDCl$_3$, ppm):

δ 0.7-1.1(b, —NHCH(CH(CH$_3$)(CH$_2$CH$_3$))COOCH$_2$CH$_3$),

δ 1.1-1.4(b, —NHCH(CH(CH$_3$)(CH$_2$CH$_3$))COOCH$_2$CH$_3$),

δ 1.4 to 1.8(b, —NHCH(CH(CH$_3$)CH$_2$CH$_3$)OCH$_2$CH$_3$)

δ 2.4-2.8(b, —NHCH$_2$CH$_2$C$_6$H$_4$OH)

δ 2.8-3.1(b, —NH(CH$_2$CH$_2$O)$_{11}$CH$_3$)

δ 3.4(s, —NH(CH$_2$CH$_2$O)$_{11}$CH$_3$),

δ 3.5-3.9(b, —NH(CH$_2$CH$_2$O)$_{11}$CH$_3$),

δ 3.9-4.3 (s, —NHCH(CH(CH$_3$)(CH$_2$CH$_3$))COOCH$_2$CH$_3$),

δ 6.7-6.9 (b, —NHCH2CH2C6H4OH),

δ 6.9-7.1 (b, —NHCH2CH2C6H4OH)

Phosphorus Nuclear Magnetic Resonance Spectrum (CDCl$_3$, ppm): δ 19.8

Average molecular weight (M$_w$): 58000

Example 19

Preparation of poly[(isoleucine ethyl ester)(aminomethoxypolyethylene glycol 550)(glycylglycine)(glycylglycyltyramine)phosphazene], [NP(IleOEt)$_{1.15}$(AMPEG550)$_{0.67}$(GlyGlyOH)$_{0.05}$(GlyGlytyramine)$_{0.13}$]$_n$ Poly(dichlorophosphazene) (2.00 g, 17.26 mmol), isoleucine ethyl ester (3.88 g, 19.85 mmol), glycylglycineallylester trifluoro acetic acid salt (1.78 g, 6.21 mmol), aminomethoxypolyethylene glycol (15.90 g, 28.91 mmol) having the molecular weight of 550, tetrakistriphenylphosphinpalladium(0) (0.72 g, 0.62 mmol), morpholine (5.41 g, 62.14 mmol), tyramine (0.51 g, 4.49 mmol), dicyclohexylcarbodiimide (0.93 g, 4.49 mmol), dimethylaminopyridine (0.55 g, 4.49 mmol), triethylamine (16.65 g, 164.58 mmol), tetrahydrofurane (550 ml), and dimethylformamide (50 ml) were used according to the same method as Example 8, to produce final product [NP(IleOEt)$_{1.15}$(AMPEG550)$_{0.67}$(GlyGlyOH)$_{0.05}$(GlyGlytyramine)$_{0.13}$]$_n$ 8.78 g (yield 76%).

Hydrogen Nuclear Magnetic Resonance Spectrum (CDCl$_3$, ppm):
δ 0.7-1.1(b, —NHCH(CH(CH$_3$)(CH$_2$CH$_3$))COOCH$_2$CH$_3$),
δ 1.1-1.4(b, —NHCH(CH(CH$_3$)(CH$_2$CH$_3$))COOCH$_2$CH$_3$),
δ 1.4 to 1.8(b, —NHCH(CH(CH$_3$)CH$_2$CH$_3$)OCH$_2$CH$_3$)
δ 2.4-2.8(b, —NHCH$_2$CONHCH$_2$CONHCH$_2$CH$_2$C$_6$H$_4$OH)
δ 2.8-3.1(b, —NH(CH$_2$CH$_2$O)$_{11}$CH$_3$)
δ 3.4(s, —NH(CH$_2$CH$_2$O)$_{11}$CH$_3$),
δ 3.5-3.9(b, —NH(CH$_2$CH$_2$O)$_{11}$CH$_3$, —NHCH$_2$CONHCH$_2$CONHCH$_2$CH$_2$C$_6$H$_4$OH)
δ 3.9-4.3 (s, —NHCH(CH(CH$_3$)(CH$_2$CH$_3$))COOCH$_2$CH$_3$, —NHCH$_2$CONHCH$_2$CONHCH$_2$CH$_2$C$_6$H$_4$OH)
δ 6.7-6.9 (b, —NHCH$_2$CONHCH$_2$CONHCH$_2$CH$_2$C$_6$H$_4$OH),
δ 6.9-7.1 (—NHCH$_2$CONHCH$_2$CONHCH$_2$CH$_2$C$_6$H$_4$OH)

Phosphorus Nuclear Magnetic Resonance Spectrum (CDCl$_3$, ppm): δ 19.8

Average molecular weight (M$_w$): 113000

Example 20

Preparation of poly[(isoleucine ethyl ester)(aminomethoxypolyethylene glycol 550)(tyrosine)phosphazene], [NP(IleOEt)$_{1.14}$(AMPEG550)$_{0.69}$(Tyrosine)$_{0.16}$]$_n$ Poly(dichlorophosphazene) (2.00 g, 17.26 mmol), isoleucine ethyl ester (3.04 g, 15.52 mmol), aminomethoxypolyethylene glycol (3.98 g, 7.24 mmol) having the molecular weight of 550, tyrosinenethylester (5.43 g, 23.45 mmol), triethylamine (17.78 g, 126.64 mmol), tetrahydrofurane (200 ml), and acetonitrile (50 ml) were used according to the same method as Example 1, to produce final product [NP(IleOEt)$_{1.18}$(AMPEG550)$_{0.62}$(Tyrosine)$_{0.20}$]$_n$ 9.26 g (yield 82%).

Hydrogen Nuclear Magnetic Resonance Spectrum (CDCl$_3$, ppm):
δ 0.7-1.1(b, —NHCH(CH(CH$_3$)(CH$_2$CH$_3$))COOCH$_2$CH$_3$),
δ 1.1-1.4(b, —NHCH(CH(CH$_3$)(CH$_2$CH$_3$))COOCH$_2$CH$_3$),
δ 1.4 to 1.8(b, —NHCH(CH(CH$_3$)CH$_2$CH$_3$)OCH$_2$CH$_3$)
δ 2.8-3.1(b, —NH(CH$_2$CH$_2$O)$_{11}$CH$_3$)
δ 3.4(s, —NH(CH$_2$CH$_2$O)$_{11}$CH$_3$),
δ 3.5-3.9(b, —NH(CH$_2$CH$_2$O)$_{11}$CH$_3$),
δ 3.9-4.3 (s, —NHCH(CH(CH$_3$)(CH$_2$CH$_3$))COOCH$_2$CH$_3$),
δ 4.7 (s, —NHCH(COOH)(C$_6$H$_4$OH)),
δ 6.7-6.9 (b, —NHCH$_2$CONHCH$_2$CONHCH(COOH)(C$_6$H$_4$OH)),
δ 6.9-7.1 (b, —NHCH$_2$CONHCH$_2$CONHCH(C$_6$H$_4$OH))

Phosphorus Nuclear Magnetic Resonance Spectrum (CDCl$_3$, ppm): δ 19.8

Average molecular weight (M$_w$): 89000

Example 21

Preparation of poly[(isoleucine ethyl ester)(aminomethoxypolyethylene glycol 550)(glycylglycine)(glycylglycyltyrosinenethylester)phosphazene], [NP(IleOEt)$_{1.15}$(AMPEG550)$_{0.67}$(GlyGlyOH)$_{0.05}$(GlyGlyTyrosineOMe)$_{0.13}$]$_n$ Poly(dichlorophosphazene) (2.00 g, 17.26 mmol), isoleucine ethyl ester (3.88 g, 19.85 mmol), glycylglycineallylester trifluoro acetic acid salt (1.78 g, 6.21 mmol), aminomethoxypolyethylene glycol (15.90 g, 28.91 mmol) having the molecular weight of 550, tetrakistriphenylphosphinpalladium(0) (0.72 g, 0.62 mmol), morpholine (5.41 g, 62.14 mmol), tyrosine methylester (0.51 g, 4.49 mmol), dicyclohexylcarbodiimide (0.93 g, 4.49 mmol), dimethylaminopyridine (0.55 g, 4.49 mmol), triethylamine (16.65 g, 164.58 mmol), tetrahydrofurane (550 ml), and dichloromethane (100 ml) were used according to the same method as Example 8, to produce final product [NP(IleOEt)$_{1.15}$(AMPEG550)$_{0.67}$(GlyGlyOH)$_{0.05}$(GlyGlyTyrosineOMe)$_{0.13}$]$_n$ 9.99 g (yield 76%).

Hydrogen Nuclear Magnetic Resonance Spectrum (CDCl$_3$, ppm):
δ 0.7-1.1(b, —NHCH(CH(CH$_3$)(CH$_2$CH$_3$))COOCH$_2$CH$_3$),
δ 1.1-1.4(b, —NHCH(CH(CH$_3$)(CH$_2$CH$_3$))COOCH$_2$CH$_3$),
δ 1.4 to 1.8(b, —NHCH(CH(CH$_3$)CH$_2$CH$_3$)OCH$_2$CH$_3$)
δ 2.8-3.1(b, —NH(CH$_2$CH$_2$O)$_{11}$CH$_3$)
δ 3.4(s, —NH(CH$_2$CH$_2$O)$_{11}$CH$_3$),
δ 3.5-3.9(b, —NH(CH$_2$CH$_2$O)$_{11}$CH$_3$, —NHCH$_2$CONHCH$_2$CONHCH(COOH)(C$_6$H$_4$OH))
δ 3.9-4.3 (s, —NHCH(CH(CH$_3$)(CH$_2$CH$_3$))COOCH$_2$CH$_3$, —NHCH$_2$CONHCH$_2$CONHCH(COOH)(C$_6$H$_4$OH))
δ 5.7 (s, —NHCH$_2$CONHCH$_2$CONHCH(COOH)(C$_6$H$_4$OH)),
δ 6.7-6.9 (b, —NHCH$_2$CONHCH$_2$CONHCH(COOH)(C$_6$H$_4$OH)),
δ 6.9-7.1 (b, —NHCH$_2$CONHCH$_2$CONHCH(COOH)(C$_6$H$_4$OH))

Average molecular weight (M$_w$): 125000

Example 22

Preparation of poly[(isoleucine ethyl ester)(aminomethoxypolyethylene glycol 550)(aminoethylsuccinate)(aminoethylmethacrylate)phosphazene], $[NP(IleOEt)_{1.19}(AMPEG550)_{0.56}(aminoethylsuccinate)_{0.05}(aminoethylsuccinateAEMA)_{0.20}]_n$ Dried isoleucine ethyl ester hydrochloride salt (4.05 g, 20.71 mmol) was dissolved in 100 ml of anhydrous tetrahydrofuran, and triethylamine (10.10 g, 72.48 mmol) was added thereto. The solution of poly(dichlorophosphazene) (2.00 g, 17.26 mmol) dissolved in anhydrous tetrahydrofuran 50 ml was added dropwise to the obtained isoleucine ethyl ester hydrochloride salt solution in dry ice-acetone bath at −60° C., allowing to react for 48 hours with slowly increasing the temperature to the room temperature.

After checking the reaction progress by checking $^{31}$P-NMR, a solution of dried aminoethanol (0.31 g, 5.18 mmol) dissolved in anhydrous tetrahydrofuran (50 ml), to which triethylamine (2.52 g, 18.12 mmol) was added, was added to the obtained reaction solution. Then, a solution of dried aminomethoxypolyethylene glycol (13.53 g, 24.60 mmol) having the molecular weight of 550 (4.70 g, 8.54 mmol) dissolved in anhydrous tetrahydrofuran 50 ml, to which triethylamine (4.17 g, 29.90 mmol) was added, was added dropwise to the obtained resulting product, allowing to react at the room temperature for 24 hours, and at 40-50° C. for 24 hours.

The reaction solution was filtered to remove a generated triethylamine hydrochloride salt. The remaining solution was concentrated under decompression until the solvent was mostly removed. The obtained concentrate solution was dissolved in a small amount of methylalcohol. The resulting solution was put into an MWCO 12000 membrane (Spectrum Laboratories, Inc.), and dialyzed with methylalcohol at room temperature for 5 days and with distilled water for 5 days. The obtained product was dried at a low temperature, to produce poly(dichlorophosphazene), $[NP(IleOEt)_{1.19}(AMPEG550)_{0.55}(Aminoethanol)_{0.25}]_n$ (7.21 g)

The obtained $[NP(IleOEt)_{1.19}(AMPEG550)_{0.56}(Aminoethanol)_{0.25}]_n$ (7.21 g, 5.89 mmol) was dissolved in tetrahydrofurane (200 ml), and reacted with 2 equivalents of succinic anhydride (1.18 g, 11.78 mmol) and 2 equivalents of dimethylaminopyridine (1.44 g, 11.78 mmol) at the room temperature for 8 hours. The remaining solution was concentrated under decompression, and dissolved in a small amount of methylalcohol. The resulting solution was dialyzed with methylalcohol at room temperature for 5 days and with distilled water at 4° C. for 5 days. The obtained product was dried at a low temperature, to produce $[NP(IleOEt)_{1.23}(AMPEG550)_{0.47}(aminoethylsuccinate)_{0.30}]_n$ (6.95 g).

The obtained $[NP(IleOEt)_{1.19}(AMPEG550)_{0.56}(aminoethylsuccinate)_{0.25}]_n$ (6.95 g) was dissolved in anhydrous dichloromethane (50 ml), and reacted with 0.50 equivalents of aminoethylmethacrylate (1.01 g, dissolved in anhydrous dimethylformamide), 0.50 equivalents of dicyclohexylcarbodiimide (1.20 g), 0.60 equivalents of hydroxysuccinimide (0.84 g), and tri-n-butylamine (2.27 g) at 0° C. for 24 hours. The remaining solution was concentrated under decompression, and dissolved in a small amount of methylalcohol. The resulting solution was put into an MWCO 6-8000 membrane (Spectrum Laboratories, Inc.), and dialyzed with methylalcohol at room temperature for 5 days and with distilled water at 4° C. for 5 days. The obtained product was dried at a low temperature, to produce final product $[NP(IleOEt)_{1.19}(AMPEG550)_{0.56}(Aminoethylsuccinate)_{0.05}(AminoethylsuccinateAEMA)_{0.20}]_n$ 6.72 g (yield 89%).

Hydrogen Nuclear Magnetic Resonance Spectrum (CDCl$_3$, ppm):

$\delta$ 0.7 to 1.1(b, —NHCH(CH(CH$_3$)CH$_2$CH$_3$)OCH$_2$CH$_3$), $\delta$ 1.1 to 1.3(b, —NHCH(CH(CH$_3$)CH$_2$CH$_3$)OCH$_2$CH$_3$), $\delta$ 1.4 to 1.8(b, —NHCH(CH(CH$_3$)CH$_2$CH$_3$)OCH$_2$CH$_3$), $\delta$ 1.9(s, —NHCH$_2$CH$_2$OCOCH$_2$CH$_2$CONHCH$_2$CH$_2$O$_2$C(CH$_3$)C=CH$_2$), $\delta$ 2.5 to 2.7(b, —NHCH$_2$CH$_2$OCOCH$_2$CH$_2$CONHCH$_2$CH$_2$O$_2$C(CH$_3$)C=CH$_2$), $\delta$ 2.9 to 3.2(b, —NHCH$_2$CH$_2$OCOCH$_2$CH$_2$CONHCH$_2$CH$_2$O$_2$C(CH$_3$)C=CH$_2$), $\delta$ 3.4(s, —NH(CH$_2$CH$_2$O)$_{11}$CH$_3$), $\delta$ 3.4 to 3.8(b, —NH(CH$_2$CH$_2$O)$_{11}$CH$_3$), $\delta$ 3.9 to 4.3(b, —NHCH(CH(CH$_3$)CH$_2$CH$_3$)OCH$_2$CH$_3$, —NHCH$_2$CH$_2$OCOCH$_2$CH$_2$CONHCH$_2$CH$_2$O$_2$C(CH$_3$)C=CH$_2$), $\delta$ 5.5(s, —NHCH$_2$CH$_2$OCOCH$_2$CH$_2$CONHCH$_2$CH$_2$O$_2$C(CH$_3$)C=CH$_2$)

$\delta$ 6.1(s, —NHCH$_2$CH$_2$OCOCH$_2$CH$_2$CONHCH$_2$CH$_2$O$_2$C(CH$_3$)C=CH$_2$)

Phosphorus Nuclear Magnetic Resonance Spectrum (CDCl$_3$, ppm): $\delta$ 18.4

Average molecular weight ($M_m$): 122000

Example 23

Preparation of poly[(isoleucine ethyl ester)(aminomethoxypolyethylene glycol 550)(aminoethylsuccinate)(aminoethylsuccinatehydroxyethylmethacrylate)phosphazene], $[NP(IleOEt)_{1.19}(AMPEG550)_{0.56}(Aminoethylsuccinate)_{0.03}(AminoethylsuccinateHEMA)_{0.22}]_n$ Poly(dichlorophosphazene) (2.00 g, 17.26 mmol), isoleucine ethyl ester (4.05 g, 20.71 mmol), aminomethoxypolyethylene glycol (7.27 g, 13.29 mmol) having the molecular weight of 550, aminoethanol (0.31 g, 5.18 mmol), succinic anhydride (1.16 g, 11.63 mmol), dimethylaminopyridine (2.24 g, 17.74 mmol), hydroxyethylmethacrylate (1.01 g, 6.11 mmol), dicyclohexylcarbodiimide (1.20 g, 6.70 mmol), dimethylaminopyridine (0.82 g, 6.11 mmol), triethylamine (16.86 g, 166.54 mmol), tetrahydrofurane (550 ml), and dichloromethane (100 ml) were used according to the same method as Example 22, to produce final product [NP(IleOEt) 1.19(AMPEG550)$_{0.56}$(GlyGlyOH)$_{0.03}$(GlyGlyHEMA)$_{0.22}$]$_n$ 6.86 g (yield 77%).

Hydrogen Nuclear Magnetic Resonance Spectrum (CDCl$_3$, ppm):

$\delta$ 0.8-1.1(b, —NHCH(CH(CH$_3$)(CH$_2$CH$_3$))COOCH$_2$CH$_3$), $\delta$ 1.1-1.4(b, —NHCH(CH(CH$_3$)(CH$_2$CH$_3$))COOCH$_2$CH$_3$), $\delta$ 1.9 (b, —NHCH$_2$CH$_2$O$_2$CCH$_2$CH$_2$CO$_2$CH$_2$CH$_2$O$_2$C(CH$_3$)C=CH$_2$), $\delta$ 2.5 (b, —NHCH$_2$CH$_2$O$_2$CCH$_2$CH$_2$CO$_2$CH$_2$CH$_2$O$_2$C(CH$_3$)C=CH$_2$), $\delta$ 2.8 to 3.0(b, —NHCH$_2$CH$_2$O$_2$CH$_2$CH$_2$CO$_2$CH$_2$CH$_2$O$_2$C(CH$_3$)C=CH$_2$), $\delta$ 3.4(s, —NH(CH$_2$CH$_2$O)$_{11}$CH$_3$), $\delta$ 3.5-3.9(b, —NH(CH$_2$CH$_2$O)$_{11}$CH$_3$), δ 4.0-4.4(b, —NHCH(CH(CH$_3$)(CH$_2$CH$_3$))COO CH$_2$CH$_3$, —NHCH$_2$CH$_2$O$_2$CCH$_2$CH$_2$CO$_2$CH$_2$CH$_2$O$_2$C(CH$_3$)C=CH$_2$), δ 5.4(s, —NHCH$_2$CH$_2$O$_2$CCH$_2$CH$_2$CO$_2$CH$_2$CH$_2$O$_2$C(CH$_3$)C=CH$_2$)

δ 6.0(s, —NHCH$_2$CH$_2$O$_2$CCH$_2$CH$_2$CO$_2$CH$_2$CH$_2$O$_2$C(CH$_3$)C=CH$_2$)

Phosphorus Nuclear Magnetic Resonance Spectrum (CDCl$_3$, ppm): δ 19.4

Average molecular weight (M$_w$): 121600

Example 24

Preparation of poly[(isoleucine ethyl ester)(aminomethoxypolyethylene glycol 550)(aminoethylsuccinate)(aminoethylsuccinatecystine ethyl ester)phosphazene], [NP(IleOEt)$_{1.19}$(AMPEG550)$_{0.56}$(Aminoethylsuccinate)$_{0.06}$(AminoethylsuccinateCysOEt)$_{0.19}$]$_n$ Poly(dichlorophosphazene) (2.00 g, 17.26 mmol), isoleucine ethyl ester (4.05 g, 20.71 mmol), aminomethoxypolyethylene glycol (7.27 g, 13.29 mmol) having the molecular weight of 550, aminoethanol (0.31 g, 5.18 mmol), succinic anhydride (1.19 g, 11.90 mmol), dimethylaminopyridine (1.45 g, 11.90 mmol), cystine ethyl ester (0.40 g, 4.14 mmol), dicyclohexylcarbodiimide (1.23 g, 6.28 mmol), 0.60 equivalents of hydroxysuccinimide (0.87 g, 7.53 mmol), triethylamine (16.89 g, 166.88 mmol), tetrahydrofurane (550 ml), in and dichloromethane (100 ml) were used according to the same method as Example 22, to produce final product [NP(IleOEt)$_{1.19}$(AMPEG550)$_{0.56}$((Aminoethylsuccinate)$_{0.06}$(AminoethylsuccinateCysOEt)$_{0.19}$]$_n$ 7.04 g (yield 80%).

Hydrogen Nuclear Magnetic Resonance Spectrum (CDCl$_3$, ppm):
δ 0.8-1.1(b, —NHCH(CH(CH$_3$)(CH$_2$CH$_3$))COOCH$_2$CH$_3$),
δ 1.1-1.4(b, —NHCH(CH(CH$_3$)(CH$_2$CH$_3$))COOCH$_2$CH$_3$), —NHCH$_2$CH$_2$OCOCH$_2$CH$_2$CONHCH(CH$_2$SH)(COOCH$_2$CH$_3$)),
δ 2.3-2.5(b, —NHCH$_2$CH$_2$OCOCH$_2$CH$_2$CONHCH(CH$_2$SH)(COOCH$_2$CH$_3$)),
δ 2.9-3.0(b, —NHCH$_2$CH$_2$OCOCH$_2$CH$_2$CONHCH(CH$_2$SH)(COOCH$_2$CH$_3$)),
δ 3.4(s, —NH(CH$_2$CH$_2$O)$_{11}$CH$_3$),
δ 3.5-3.9(b, —NH(CH$_2$CH$_2$O)$_{11}$CH$_3$,
δ 4.0-4.4(b, —NHCH(CH(CH$_3$)(CH$_2$CH$_3$))COOCH$_2$CH$_3$, —NHCH$_2$CH$_2$OCOCH$_2$CH$_2$CONHCH(CH$_2$SH)(COOCH$_2$CH$_3$))

Phosphorus Nuclear Magnetic Resonance Spectrum (CDCl$_3$, ppm): δ 19.8

Average molecular weight (M$_w$): 105000

Example 25

Preparation of poly[(isoleucine ethyl ester)(aminomethoxypolyethylene glycol 550)(aminoethylsuccinate)(aminoethylsuccinatecysteamine)phosphazene], [NP(IleOEt)$_{1.19}$(AMPEG550)$_{0.56}$(Aminoethylsuccinate)$_{0.02}$(AminoethylsuccinCysteamine)$_{0.23}$]$_n$ Poly(dichlorophosphazene) (2.00 g, 17.26 mmol), isoleucine ethyl ester (4.05 g, 20.71 mmol), aminomethoxypolyethylene glycol ((7.27 g, 13.29 mmol) having the molecular weight of 550, aminoethanol (0.31 g, 5.18 mmol), succinic anhydride (1.15 g, 11.50 mmol), dimethylaminopyridine (1.41 g, 11.50 mmol), cysteamine (0.71 g, 9.17 mmol), dicyclohexylcarbodiimide (1.20 g, 6.11 mmol), hydroxysuccinimide (0.84 g, 7.34 mmol), triethylamine (16.89 g, 111.38 mmol), tetrahydrofurane (550 ml), and dichloromethane (100 ml) were used according to the same method as Example 22, to produce final product [NP(IleOEt)$_{1.19}$(AMPEG550)$_{0.56}$((Aminoethylsuccinate)$_{0.02}$(AminoethylsuccinateCysteamine)$_{0.23}$]$_n$ 7.04 g (yield 75%).

Hydrogen Nuclear Magnetic Resonance Spectrum (CDCl$_3$, ppm):
δ 0.7 to 1.1(b, —NHCH(CH(CH$_3$)CH$_2$CH$_3$)COOCH$_2$CH$_3$),
δ 1.1 to 1.3(b, —NHCH(CH(CH$_3$)CH$_2$CH$_3$)COOCH$_2$CH$_3$),
δ 1.4 to 1.8(b, —NHCH(CH(CH$_3$)CH$_2$CH$_3$)COOCH$_2$CH$_3$),
δ 2.5 to 2.7(b, —NHCH$_2$CH$_2$OCOCH$_2$CH$_2$CONHCH$_2$CH$_2$SH)
δ 2.8 to 3.2(b, —NHCH$_2$CH$_2$OCOCH$_2$CH$_2$CONHCH$_2$CH$_2$SH,
δ 3.4(s, —NH(CH$_2$CH$_2$O)$_{11}$CH$_3$),
δ 3.5(b, —NHCH$_2$CH$_2$OCOCH$_2$CH$_2$CONHCH$_2$CH$_2$SH,
δ 3.4 to 3.8(b, —NH(CH$_2$CH$_2$O)$_{11}$CH$_3$),
δ 3.9 to 4.3(b, —NHCH(CH(CH$_3$)CH$_2$CH$_3$)COOCH$_2$CH$_3$, —NHCH$_2$CH$_2$OCOCH$_2$CH$_2$CONHCH$_2$CH$_2$SH)

Phosphorus Nuclear Magnetic Resonance Spectrum (CDCl$_3$, ppm): δ 18.2

Average molecular weight (M$_w$): 85000

Example 26

Preparation of poly[(isoleucine ethyl ester)(aminomethoxypolyethylene glycol 550)(aminoethylsuccinate)(aminoethylsuccinatetyramine)phosphazene], [NP(IleOEt)$_{1.19}$(AMPEG550)$_{0.56}$(Aminoethylsuccinate)$_{0.04}$(AminoethylsuccinateTyramine)$_{0.21}$]$_n$ Poly(dichlorophosphazene) (2.00 g, 17.26 mmol), isoleucine ethyl ester (4.05 g, 20.71 mmol), aminomethoxypolyethylene glycol (7.27 g, 13.29 mmol) having the molecular weight of 550, aminoethanol (0.31 g, 5.18 mmol), succinic anhydride (1.15 g, 11.50 mmol), dimethylaminopyridine (1.41 g, 11.50 mmol), tyramine (0.84 g, 6.11 mmol), dicyclohexylcarbodiimide (1.20 g, 6.11 mmol), hydroxysuccinimide (0.84 g, 7.34 mmol), triethylamine (20.35 g, 123.61 mmol), tetrahydrofurane (550 ml), and dichloromethane (100 ml) were used according to the same method as Example 22, to produce final product [NP(IleOEt)$_{1.19}$(AMPEG550)$_{0.56}$(Aminoethylsuccinate)$_{0.04}$(AminoethylsuccinateTyramine)$_{0.21}$]$_n$ 7.30 g (yield 79%).

Hydrogen Nuclear Magnetic Resonance Spectrum (CDCl$_3$, ppm):
δ 0.7-1.1(b, —NHCH(CH(CH$_3$)(CH$_2$CH$_3$))COOCH$_2$CH$_3$),
δ 1.1-1.4(b, —NHCH(CH(CH$_3$)(CH$_2$CH$_3$))COOCH$_2$CH$_3$),
δ 1.4 to 1.8(b, —NHCH(CH(CH$_3$)CH$_2$CH$_3$)COOCH$_2$CH$_3$)
δ 2.4-2.8(b, —NHCH$_2$CH$_2$OCOCH$_2$CH$_2$CONHCH$_2$CH$_2$C$_6$H$_4$OH)
δ 2.8-3.1(b, —NH(CH$_2$CH$_2$O)$_{11}$CH$_3$), —NHCH$_2$CH$_2$OCOCH$_2$CH$_2$CONHCH$_2$CH$_2$C$_6$H$_4$OH)

δ 3.4(s, —NH(CH$_2$CH$_2$O)$_{11}$CH$_3$),
δ 3.5-3.9(b, —NH(CH$_2$CH$_2$O)$_{11}$CH$_3$,
δ 3.9-4.3 (s, —NHCH(CH(CH$_3$)(CH$_2$CH$_3$))COO CH$_2$CH$_3$, —NHCH$_2$ CH$_2$OCOCH$_2$CH$_2$CONHCH$_2$CH$_2$C$_6$H$_4$OH)
δ 6.7-6.9 (b, —NHCH$_2$CONHCH$_2$CONH CH$_2$CH$_2$C$_6$H$_4$OH),
δ 6.9-7.1 (—NHCH$_2$CONHCH$_2$CONH CH$_2$CH$_2$C$_6$H$_4$OH)
Phosphorus Nuclear Magnetic Resonance Spectrum (CDCl$_3$, ppm): δ 19.8
Average molecular weight (M$_w$): 98000

Example 27

Preparation of poly[(isoleucine ethyl ester)(aminomethoxypolyethylene glycol 550)(glycylglycine)(glycylglycyltyrosinenethylester)phosphazene], [NP(IleOEt)$_{1.19}$(AMPEG550)$_{0.56}$(Aminoethylsuccinate)$_{0.07}$(AminoethylsuccinateTyrosineOMe)$_{0.18}$]$_n$ Poly(dichlorophosphazene) (2.00 g, 17.26 mmol), isoleucine ethyl ester (4.05 g, 20.71 mmol), aminomethoxypolyethylene glycol (7.27 g, 13.29 mmol) having the molecular weight of 550, aminoethanol (0.31 g, 5.18 mmol), succinic anhydride (1.15 g, 11.50 mmol), dimethylaminopyridine (1.41 g, 11.50 mmol), tyrosinemethylester (1.21 g, 6.18 mmol), dicyclohexylcarbodiimide (1.21 g, 6.18 mmol), hydroxysuccinimide (0.85 g, 7.42 mmol), triethylamine (20.36 g, 123.75 mmol), tetrahydrofurane (550 ml), and dichloromethane (100 ml) were used according to the same method as Example 22, to produce final product [NP(IleOEt)$_{1.19}$(AMPEG550)$_{0.56}$(Aminoethylsuccinate)$_{0.07}$(AminoethylsuccinateTyrosineOMe)$_{0.18}$]$_n$ 7.01 g (yield 75%).
Hydrogen Nuclear Magnetic Resonance Spectrum (CDCl$_3$, ppm):
δ 0.7-1.1(b, —NHCH(CH(CH$_3$)(CH$_2$CH$_3$))OCH$_2$CH$_3$),
δ 1.1-1.4(b, —NHCH(CH(CH$_3$)(CH$_2$CH$_3$))OCH$_2$CH$_3$),
δ 1.4 to 1.8(b, —NHCH(CH(CH$_3$)CH$_2$CH$_3$)OCH$_2$CH$_3$)
δ 2.4-2.8(b, —NHCH$_2$CH$_2$OCO CH$_2$CH$_2$CONHCH(COOH)(C$_6$H$_4$OH))
δ 2.8-3.1(b, —NH(CH$_2$CH$_2$O)$_{11}$CH$_3$), —NH CH$_2$CH$_2$OCOCH$_2$CH$_2$CONNHCH(COOH)(C$_6$H$_4$OH))
δ 3.4(s, —NH(CH$_2$CH$_2$O)$_{11}$CH$_3$),
δ 3.5-3.9(b, —NH(CH$_2$CH$_2$O)$_{11}$CH$_3$,
δ 3.9-4.3 (s, —NHCH(CH(CH$_3$)(CH$_2$CH$_3$))COO CH$_2$CH$_3$, —NHCH$_2$ CH$_2$OCOCH$_2$CH$_2$CONHCH(COOH)(C$_6$H$_4$OH))
δ 5.7 (s, —NHCH$_2$CH$_2$OCOCH$_2$CH$_2$CONH CH(COOH)(C$_6$H$_4$OH)),
δ 6.7-6.9 (b, —NHCH$_2$CH$_2$OCOCH$_2$CH$_2$CONHCH (COOH)(C$_6$H$_4$OH)),
δ 6.9-7.1 (b, —NHCH$_2$CH$_2$OCOCH$_2$CH$_2$CONHCH (COOH)(C$_6$H$_4$OH))
Phosphorus Nuclear Magnetic Resonance Spectrum (CDCl$_3$, ppm): δ 19.8
Average molecular weight (M$_w$): 113000

Example 28

Observation of the Sol-Tel Phase Transition of Poly(organophosphazene) Depending on Temperature The poly(organophosphazene)s obtained in Examples 1 to 21 were respectively dissolved in phosphate buffered saline (pH 7.4) at 4° C. to make solutions with concentrations of 10 wt %. The solutions were put into a chamber of a Brookfield DV-III+ Rheometer equipped with a thermostatic bath (TC-501). The sol-gel phase transition was observed while raising the temperature at the rate of 0.04° C./min and a shear rate of 0.1 to 1.7 per second.
FIG. 1 is a photograph showing the sol-gel phase transition of the poly(organophosphazene) of the present invention with temperature change. It shows that at a temperature below the initial gelling temperature, the polymer solution is in the fluid sol-phase, and at the maximum gelling temperature above the initial gelling temperature, it changed into the gel-phase.
The gel properties of the thermosensitive poly(organophosphazene)s of the present invention depending on temperature observed as above are shown in the following Table 1.

TABLE 1

Gel properties of poly(organophosphazene)s depending on temperature

| Polymer | Structure | Max. gelling temp. (° C.) | Max. gel solidity (Pa · s) |
|---|---|---|---|
| Example 1 | [NP(IleOEt)$_{1.16}$(AMPEG550)$_{0.60}$(AEMA)$_{0.23}$]$_n$ | 33 | 977 |
| Example 2 | [NP(IleOEt)$_{1.21}$(AMPEG550)$_{0.57}$(AEMA)$_{0.21}$]$_n$ | 28 | 1547 |
| Example 3 | [NP(IleOEt)$_{1.23}$(AMPEG550)$_{0.61}$(AEMA)$_{0.15}$]$_n$ | 28 | 587 |
| Example 4 | [NP(IleOEt)$_{1.17}$(AMPEG550)$_{0.68}$(AEMA)$_{0.14}$]$_n$ | 39 | 198 |
| Example 5 | [NP(IleOEt)$_{1.17}$(AMPEG750)$_{0.55}$(AEMA)$_{0.28}$]$_n$ | 54 | 40 |
| Example 6 | [NP(IleOEt)$_{1.23}$(AMPEG550)$_{0.61}$(HEMA)$_{0.15}$]$_n$ | 37 | 115 |
| Example 7 | [NP(IleOEt)$_{1.04}$(AMPEG750)$_{0.74}$(HEMA)$_{0.22}$]$_n$ | — | — |
| Example 8 | [NP(IleOEt)$_{1.27}$(AMPEG550)$_{0.51}$(GlyGlyOH)$_{0.09}$(GlyGlyAEMA)$_{0.13}$]$_n$ | 18 | 1417 |
| Example 9 | [NP(IleOEt)$_{1.29}$(AMPEG550)$_{0.54}$(GlyGlyOH)$_{0.02}$(GlyGlyHEMA)$_{0.15}$]$_n$ | 25 | 807 |
| Example 10 | [NP(IleOEt)$_{1.21}$(AMPEG550)$_{0.64}$(CysOEt)$_{0.15}$]$_n$ | 32 | 218 |
| Example 11 | [NP(IleOEt)$_{0.96}$(AMPEG550)$_{0.78}$(CysOEt)$_{0.24}$]$_n$ | — | — |
| Example 12 | [NP(IleOEt)$_{1.02}$(AMPEG750)$_{0.43}$(CysOEt)$_{0.54}$]$_n$ | 42 | 392 |
| Example 13 | [NP(IleOEt)$_{1.12}$(AMPEG550)$_{0.73}$(GlyLacOEt)$_{0.06}$(CysOEt)$_{0.09}$]$_n$ | 38 | 82 |
| Example 14 | [NP(IleOEt)$_{1.15}$(AMPEG550)$_{0.60}$(GlyLacOEt)$_{0.09}$(GlyCysOEt)$_{0.16}$]$_n$ | 35 | 526 |
| Example 15 | [NP(IleOEt)$_{1.19}$(AMPEG550)$_{0.64}$(GlyGlyOH)$_{0.05}$(GlyGlyCysOEt)$_{0.12}$]$_n$ | 30 | 97 |
| Example 16 | [NP(IleOEt)$_{1.18}$(AMPEG550)$_{0.62}$(cysteamine)$_{0.20}$]$_n$ | 40 | 248 |
| Example 17 | [NP(IleOEt)$_{1.16}$(AMPEG550)$_{0.62}$(GlyGlyOH)$_{0.05}$(GlyGlycysteamine)$_{0.17}$]$_n$ | 29 | 411 |
| Example 18 | NP(IleOEt)$_{1.14}$(AMPEG550)$_{0.68}$(Tyramine)$_{0.17}$]$_n$ | 34 | 215 |
| Example 19 | NP(IleOEt)$_{1.16}$(AMPEG550)$_{0.62}$(GlyGlyOH)$_{0.05}$(GlyGlyTyramine)$_{0.17}$]$_n$ | 33 | 520 |

TABLE 1-continued

Gel properties of poly(organophosphazene)s depending on temperature

| Polymer | Structure | Max. gelling temp. (° C.) | Max. gel solidity (Pa · s) |
|---|---|---|---|
| Example 20 | NP(IleOEt)$_{1.10}$(AMPEG550)$_{0.76}$(TyrosineOMe)$_{0.14}]_n$ | 30.8 | 215 |
| Example 21 | NP(IleOEt)$_{1.16}$(AMPEG550)$_{0.62}$(GlyGlyOH)$_{0.05}$(GlyGlyTyrosineOMe)$_{0.17}]_n$ | 28 | 405 |

In Table 1, the term "Max. (maximum) gelling temp. (temperature)" means the temperature where the viscosity of the polymer solution reaches the maximum point, and the term "Max. gel solidity" means the maximum viscosity of the polymer solution.

Figure 2:
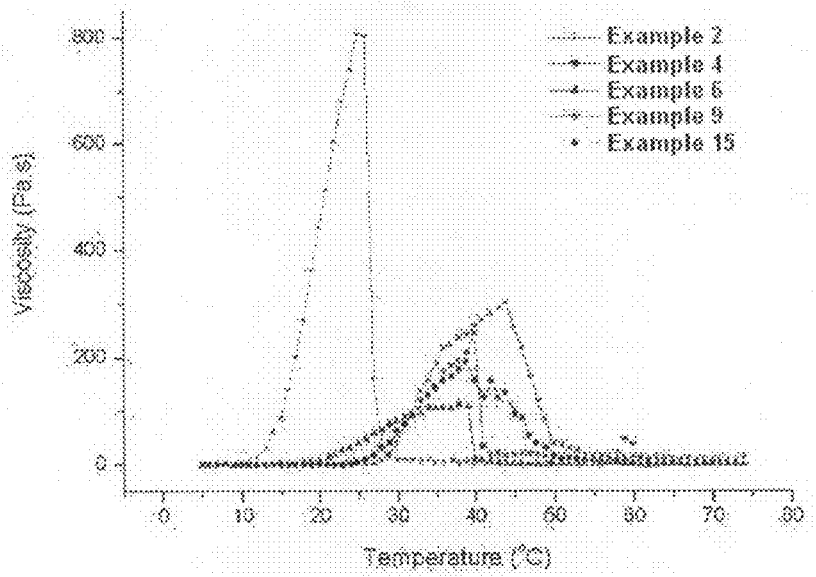
FIG. 2 shows the change in viscosity of the temperature-sensitive phosphazene-based polymer that is capable of forming cross-linkings according to an embodiment of the present invention in accordance with a temperature change.

The changes of the viscosity of the poly(organophosphazene)s of the present invention depending on temperature are shown in FIG. 2.

As known from Table 1 and FIG. 2, a poly(organophosphazene)s with a wide range of the maximum gelling temperature and the maximum gel solidity can be confirmed by regulating the kind of the hydrophobic amino acid ester substituted in the phosphazene-based polymer, the kind of amino acid, peptide, or depsipeptide that are capable of controlling the degradation rate, the kind of substituents that is capable of forming a cross-linking bond, the chain length of methoxypolyethyleneglycol, and the composition of all the substituents.

Further, the phosphazene polymers prepared in Examples 7 and 11 have thiol groups or vinyl groups that are exposed to ultraviolet radiation and form cross-linking bonds, but they exhibit no viscosity change with the temperature change due to the high content of methoxypolyethylene glycol.

Example 29

Preparation of Phosphazene-Based Polymer Hydrogel Having Cross-Linking Bonds by Ultraviolet Radiation The solution of phosphazene polymer prepared in Example 4 dissolved in phosphate-buffered saline in the concentration of 10 wt % was put into millicells, to form hydrogel at 37° C. In addition, the solution of phosphazene polymer prepared in Example 4 dissolved in phosphate-buffered saline in the concentration of 10 wt % containing 1 wt % of a photo-initiator, 2,2-diphenyl-1-picrylhydrazyl, was put into millicells, to form hydrogel at 37° C., and then, exposed to 365 nm UV, 0.61 mW/cm2 at 37° C. for 1 minute, to prepare phosphazene-based polymer hydrogel having cross-linking bonds.

As shown in FIG. 1, the phosphazene-based polymer hydrogel having cross-linking bonds by exposure to UV maintains its network structure by linking bonds even when the temperature is lowered, thereby maintaining gel-phase. However, the phosphazene-based polymer hydrogel without cross-linking bonds maintain the network structure at 37° C., but when the temperature is lowered, the network structure is destroyed, and converted into sol (liquid) phase.

Figure 3:
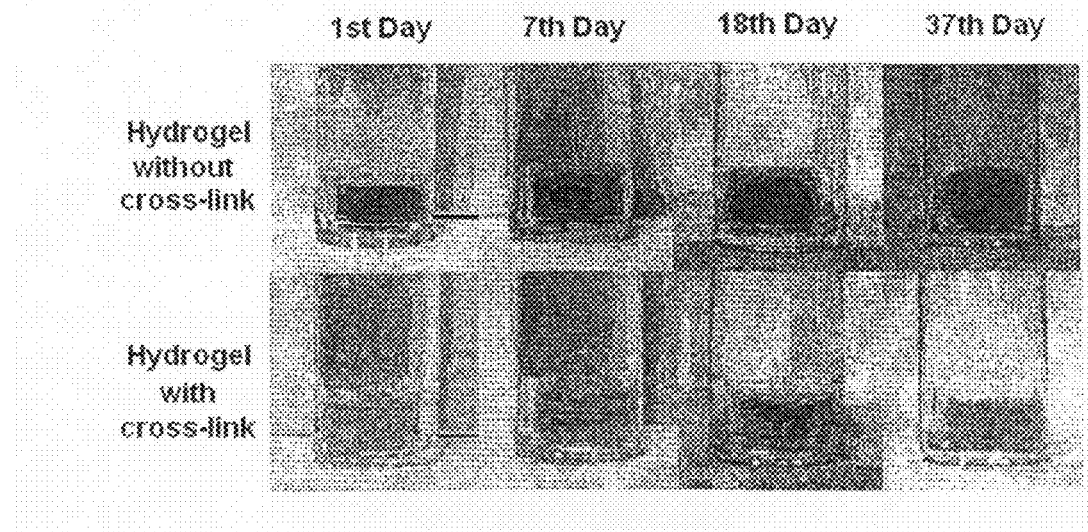
FIG. 3 shows the change in swelling degree of the phosphazene-based polymer hydrogel having cross-linkings according to time course according to an embodiment of the present invention.

The millicells containing the phosphazene-based polymer hydrogel with cross-linking bonds and the phosphazene-based polymer hydrogel without cross-linking bonds were immersed in 10 ml of phosphate-buffered saline at 37° C., and then, the degree of swelling of the hydrogel according to time course was evaluated and shown in FIG. 3.

As shown in FIG. 3, the hydrogel without cross-linking bonds considerably swells according to time course, while the hydrogel with cross-linking bonds maintains its volume even after 37 days.

Example 30

Preparation of Phosphazene-Based Polymer Hydrogel with Cross-Linking Bonds Using Phosphazene-Based Polymer Having Vinyl Substituents and Thiol Based Crosslinking Agent The phosphazene polymer prepared in Example 7 was dissolved in phosphate-buffered saline in the concentration of 10 wt %, and PEG dithiol having the molecular weight of 3500 was added to the solution in the amount of 0.11 mol % based on the phosphazene polymer. The obtained solution was stirred at 50 rpm at 37° C., and then the sol-gel transition behaviour was observed according to time course. The solution of the phosphazene-based polymer of Example 7 dissolved in phosphate-buffered saline, which was not gellated at 37° C., became gellated after 12 hours at 37° C.

The phosphazene-based polymer of Example 4 was dissolved in phosphate-buffered saline in the concentration of 10 wt %, which was gellation at 37° C. PEG dithiol having the molecular weight of 3500 was added to the solution in the amount of 0.07 mol % based on the phosphazene polymer. The solution was stirred at 50 rpm at 37° C., and the gel solidity according to crosslinking time was measured and shown in FIG. 4. As the crosslinking time is longer, the hydrogel has the increased gel solidity, thereby maintaining its viscosity at low temperature. When the number of the cross-linkings is increased, the hydrogel maintains the gel phase at low temperature.

Such results show that the phosphazene-based polymer solution that is capable of forming cross-linkings exhibits the sol-gel transition by chemical crosslining bonds. In addition, the phosphazene-based polymer solution that is capable of forming cross-linkings and has temperature sensitivity is gellated by raising temperature, and after gallation, the formed gel becomes solider by forming more cross-linkings in the gel.

Example 31

Preparation of Phosphazene-Based Polymer Hydrogel with Cross-Linking Bonds Using Phosphazene-Based Polymer Having Thiol Substituents and Vinyl Based Crosslinking Agent The phosphazene polymer prepared in Example 11 was dissolved in phosphate-buffered saline in the concentration of 10 wt %, and vinyl sulfonate-4-arm PEG was added to the solution in the amount of 0.12 mol % based on the phosphazene polymer. The obtained solution was stirred at 50 rpm at 37° C., and then the sol-gel transition behaviour was observed according to time course. The solution of the phosphazene-based polymer of Example 11 dissolved in phosphate-buffered saline, which was not gellated at 37° C., became gellated with in 10 minutes at 37° C.

The phosphazene-based polymer of Example 13 was dissolved in phosphate-buffered saline in the concentration of 10 wt %, which was gellation at 37° C. Vinyl sulfonate-4-arm PEG was added to the solution in the amount of 0.03 mol % based on the phosphazene-based polymer of Example 13. The solution was stirred at 50 rpm at 37° C., and the gel solidity according to crosslinking time was measured. As the crosslinking time is longer, the hydrogel has the increased gel solidity, thereby maintaining its viscosity at low temperature. When the number of the cross-linkings is increased, the hydrogel maintains the gel phase at low temperature.

Example 32

Preparation of Phosphazene-Based Polymer Hydrogel with Cross-Linking Bonds Using Tyramine Substituents and Enzyme The phosphazene-based polymer prepared in Example 18 was dissolved in phosphate-buffered saline in the concentration of 10 wt %, where the solution was gellated at 37° C. To the solution, horseradish peroxidase was added in the amount of 0.58 wt %, based on the phosphazene-based polymer of the Example 18, and then stirred at 50 rpm at 37° C. The gel solidity according to crosslinking time was measured. As the crosslinking time is longer, the hydrogel has the increased gel solidity, thereby maintaining its viscosity at low temperature. When the number of the cross-linkings is increased, the hydrogel maintains the gel phase at low temperature. When the number of the cross-linkings is increased, the hydrogel maintains the gel phase at low temperature.

Example 33

Preparation of Phosphazene-Based Polymer Hydrogel with Cross-Linking Bonds Using Tyrosine Substituents and Enzyme The phosphazene bled polymer prepared in Example 20 was dissolved in phosphate-buffered saline in the concentration of 10 wt %, where the solution was gellated at 37° C. To the solution, horseradish peroxidase was added in the amount of 0.58 wt % based on the phosphazene-based polymer of Example 20, and then stirred at 50 rpm at 37° C. The gel solidity according to crosslinking time was measured. As the crosslinking time is longer, the hydrogen has the increased gel solidity, thereby maintaining its viscosity at low temperature. When the number of the cross-linkings is increased, the hydrogel maintains the gel phase at low temperature. When the number of the cross-linkings is increased, the hydrogel maintains the gel phase at low temperature Example 34

Measurement of Swelling Degree of Phosphazene-Based Polymer Hydrogel with Cross-Linkings according to UV Exposure Time 100 mg of a solution of the phosphazene based polymer prepared in Example 4 dissolved in phosphate-buffered saline in the concentration of 10 wt % and containing 1 wt % of a photo initiator, 2,2-diphenyl-1-picrylhydrazyl, was dropped onto a slide glass, allowing to form hydrogen at 37° C., and exposed to 365 nm, 0.61 mW/cm2) UV for 1-5 minutes to prepare phosphazene-based polymer hydrogel with cross-linkings. The slide glass, on which the hydrogel is formed, was immersed in 40 ml of distilled water for 24 hours. After carefully removing moisture around the hydrogel, the weight of the swelled hydrogel was measured. Thereafter, the swelled hydrogel was freeze-dried, and the weight thereof was measured. The swelling degree of the hydrogel according to the time of exposure to UV was evaluated by the following equation.

$$\text{Swelling Degree} = \frac{\text{Weight of Swelled hydrogel} - \text{Weight of Dried Hydrogel}}{\text{Weight of Dried Hydrogel}} \times 100$$

The swelling degrees of the hydrogel having cross-linkings that formed by exposure to UV for various time periods as measured above were shown in the fillowing Table 2.

TABLE 2

| Swelling degrees of the hydrogel according to various UV exposure time periods | | | | | |
|---|---|---|---|---|---|
| UV Exposure Time | 1 min. | 2 min. | 3 min. | 4 min. | 5 min. |
| Swelling Degree | 59.29% | 58.40% | 58.03% | 54.32% | 51.71% |

As shown in Table 2, as the time period of exposure to UV is longer, the swelling degree is lower. Such result indicates that as the time period of exposure to UV is longer, the number of cross-linkings formed by acrylate groups in the hydrogel is increased, to generate a dense network structure in the hydrogel, whereby the swelling degree is lowered.

Example 35

Measurement of Porosity of Phosphazene-Based Polymer Hydrogel Having Cross-Linkings The phosphazene-based polymers prepared in Examples 1 to 4 contain aminoethylmethacrylate groups that are capable of forming cross-linkings in the various contents of 0.23, 0.21, 0.15, and 0.14 mol %, respectively. According to the method in Example 19, the solutions of the phosphazene-based polymers of Examples 1-4 dissolved in phosphate-buffered saline in the concentration of 10 wt % were exposed to UV (365 nm, 0.61 mW/cm2) for 5 minutes to prepare polyphosphazene-based polymer hydrogels having cross-linkings. The prepared hydrogels were freeze-dried, and then, the porosities thereof were measured by SEM (Scanning Electron Microscope).

The measured porosities pf the polyphosphazene-based polymer hydrogels having cross-linkings are shown in FIG. 4. As shown in FIG. 4, as the content of the aminoethylmethacrylate group in hydrogel is increased, the pore size in the hydrogel is decreased. That is, when the content of the aminoethylmethacrylate group in hydrogel is increased, more cross-linkings are formed in the hydrogel, whereby the network structure in the hydrogel is denser and the pore size is smaller. By such property, the pore size of the hydrogel can be appropriately controlled, and when the hydrogel is used as a drug delivery carrier, even a small sized drug can be loaded in great amount, and the released around of drug can be controlled.

What is claimed is:

1. A phosphazene-based polymer represented by the following Chemical Formula 1:

(Chemical Formula 1)

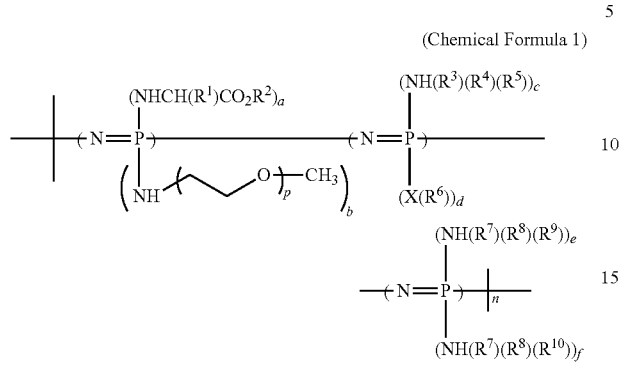

wherein, in the above formula, p is a numerical value ranging of 7 to 50, in $NHCH(R^1)CO_2R^2$, $R^1$ is selected from the group consisting of H, $CH_3$, $CH_2SH$, $CH(CH_3)_2$, $CH_2CH(CH_3)_2$, $CH(CH_3)C_2H_5$, $CH_2CH_2SCH_3$, $CH_2C_6H_5$, $CH_2C_6H_4OH$, and $CH_2C_2H_2C_6H_4$, and $R^2$ is selected from the group consisting of $CH_3$, $C_2H_5$, $C_3H_7$, $C_4H_9$, $CH_2C_6H_5$, and $CH_2CHCH_2$, in $NH(R^3)(R^4)(R^5)$, $R^3$ is $CH(W)$, $R^4$ is selected from the group consisting of $CO_2$, $CONHCH(X)CO_2CO_2$, $CH_2CO_2$, and $CO_2CH(CH_3)CO_2$, and $R^5$ is selected from the group consisting of H, $CH_3$, and $C_2H_5$, where W and X are independently selected from the group consisting of H, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2H_2C_6H_4$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4H_8NH_2$, $C_3H_6NHC(=NH)NH_2$, $CH_2C_3N_2H_3$, and $CH_2SH$, in $XR^6$, X is N or O, $R^6$ is selected from the group consisting of an acrylate-based compound, a methacrylate-based compound, an acrylamide-based compound, a vinylsulfone-based compound, a thiol-based compound, a cysteine-based compound, a cysteamine-based compound, a mercaptic acid-based compound, an allyl pyrimidine-based compound and compounds including a thiol- or vinyl-group protected with a protecting group of the above compounds, or a tyramine-based compound, a tyrosine-based compound, and a phenol-based compound, $NH(R^7)(R^8)(R^9)$ is a substitutent including a functional group, where, $R^7$ is $CH(Y)$, $R^8$ is selected from the group consisting of $CH_2$, $C_2H_4$, $C_3H_6$, $C_4H_8$, $CH_2C_6H_4$, $CH_2CO_2$, $C_2H_4CO_2$, O, $CONHCH(Z)O$, $CONHCH(Z)CONHCH(M)O$, $CONHCH(Z)CONHCH(N)CONHCH(L)O$, CO, $CO_2$, S, $CONHCH(Z)S$, $CONHCH(Z)CONHCH(M)S$, $CONHCH(Z)CONHCH(M)CONHCH(L)S$, N, $CONHCH(Z)N$, $CONHCH(Z)CONHCH(M)N$, $CONHCH(Z)CONHCH(M)CONHCH(L)N$, CON, $COCHNH(Z)CON$, $COCHNH(Z)CONHCH(M)CON$, $COCHNH(Z)CONHCH(M)CONHCH(L)CON$, $CONHCH(Z)CO$, $COCHNH(Z)CONHCH(M)CO$, $COCHNH(Z)CONHCH(M)CONHCH(L)CO$, $CONHCH(Z)CO_2$, $COCHNH(Z)CO_2$, $COCHNH(Z)CONHCH(M)CO_2$, $COCHNH(Z)CONHCH(M)CONHCH(L)CO_2$, $[OCH(CH_3)CO]_q$, $(OCH_2CO)_q$, $[(OCH(CH_3)CO]_q$, $[OCO(CH_2)_8CO]_q$, $[OCOC_6H_5O(CH_2)_3OC_6H_5CO]_q$, and $[OCOC_6H_5O(CH_2)_6OC_6H_5CO]_q$, and $R^9$ is selected from the group consisting of OH, SH, H, $NH_2$, $CH_3$, $C_2H_5$, $C_3H_7$, $C_4H_9$, $CH_2C_6H_5$, $CH_2CHCH_2$, $NHCH(SH)CO_2H$, $NH(CH_2)_q SH$, $NH(CH_2CH_2NH)_q H$, $[NHCH(C_4H_8NH_2)CO]_q OH$, $[NHCH[(CH_2)_3C(=NH)(NH_2)]CO]_q OH$, folic acid, hyaluronic acid, polyhistidine, cyclodextrin, heparin, chitosan, protamine, and a general protecting group of a functional group, where Y, Z, M, and L are independently selected from the group consisting of H, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2H_2C_6H_4$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4H_8NH_2$, $C_3H_6NHC(=NH)NH_2$, $CH_2C_3N_2H_3$, and $CH_2SH$, and q represents a number of a repeating unit and ranges from 1 to 18000, in $NH(R^7)(R^8)(R^{10})$, $R^7$ and $R^8$ are the same substitutents as in defined in the $NH(R^7)(R^8)(R^9)$, $R^{10}$ is selected from the group consisting of an acrylate-based compound, a methacrylate-based compound, an acrylamide-based compound, a vinylsulfone-based compound, a thiol-based compound, a cysteine-based compound, a cysteamine-based compound, a mercaptic acid-based compound, an allyl pyrimidine-based compound and compounds including a thiol- or vinyl-group protected with a protecting group of the above compounds, or a tyramine-based compound, a tyrosine-based compound, and a phenol-based compound, a, b, c, d, e, and f represent each content of substitutents, a and b range from 0.01 to 1.9, b, c, d, e, and f range from 0 to 1.9, d and f are not simultaneously zero, and a+b+c+d+e+f=2.0, and n represents a polymerization degree of polyphosphazene and ranges 5 to 100000.

2. The phosphazene-based polymer of claim 1, wherein in the $R^6$ and $R^{10}$, the acrylate-based compound is an acrylate; an acrylate including a C1 to C30 linear or branched alkyl unsubstituted or substituted with at least one selected from the group consisting of a halogen, a C1 to C12 alkoxy, an acryloyloxy, and an amino acid; an acrylate including an amino acid group; ethylene glycol acrylate; or a polyethyleneglycol acrylate including polyethyleneglycol of a molecular weight of 200 to 2,500, the methacrylate-based compound is methacrylate; methacrylate including a C1 to C30 linear or branched alkyl unsubstituted or substituted with at least one selected from the group consisting of a halogen, a C1 to C12 alkoxy, an acryloyloxy, and an amino acid; methacrylate including an amino acid group; or polyethyleneglycol methacrylate including polyethyleneglycol of a molecular weight of 200 to 2,500, the acrylamide-based compound is acryl amide; acryl amide including a C1 to C30 linear or branched alkyl unsubstituted or substituted with at least one selected from the group consisting of a halogen, a C1 to C12 alkoxy, acryloyloxy, and an amino acid; acryl amide including an amino acid group; ethyleneglycol acrylamide; or polyethyleneglycol amide including polyethyleneglycol of a molecular weight of 200 to 2,500, the vinyl sulfone-based compound is vinyl sulfone, vinyl sulfone-ethyleneglycol, vinyl sulfone-polyethyleneglycol including polyethyleneglycol of a molecular weight of 200 to 2,500, vinyl sulfone-alkylate including a C1 to C30 alkyl, vinyl sulfone-amino acid, or vinyl sulfone-a peptide, the thiol-based compound is thiol-polyethylene glycol including polyethylene glycol of a molecular weight of 200 to 2,500, or thiol-alkylate including a $C_1$ to $C_{30}$ alkyl, the cysteine-based compound is cysteine, N-acetyl-cysteine, or N-acetyl-cysteine alkyl ester including a C1 to C30 alkyl, the cysteamine-based compound is cysteamine, or N-acetyl-cysteamine, the mercaptic acid-based compound is 2-mercapto succinic acid, the allyl pyrimidine-based compound is 1-allyl-2-aminopyridinium, or 1-allyl-6-amino-3-ethyl-5-nitrosouracil, the tyramine-based compound is tyramine, or 3-methoxytyramine, the tyrosine-based compound is tyrosine, or tyrosine methylester, or tyrosine ethylester, and the phenol-based compound is selected from the group consisting of 2-amino-4-phenylphenol, 2-amino-4-teriaryamylphenol, 2-amino-4-tert-butylphenol phenol, 8-amino-2-naphthol, 5-amino-1-naphthol, 4-amino-1-naphthol, 3-amino-2-naphthol, 1-amino-2-naphthol, 4-amino 2,5 dimethylphenol, 5-amino-2-methoxyphenol, 5-amino-2-methylphenol, 4-amino-3-methylphenol, 4-amino-2-methylphenol, 2-amino-5-methylphenol, 2-amino-4-methylphenol, 2-amino-3-methylphenol, 2,4-diaminophenol, 2,3-diaminophenol, 4-aminophenol, 3-aminophenol, 2-aminophenol, 4-amino-3-nitrophenol, 4-amino-2-nitrophenol, 2-amino-5-nitrophenol, 2-amino-4-nitrophenol, 2-amino-4 fluorophenol, 4-amino-3-chlorophenol, 4-amino-2-chlorophenol, 3-amino-4-chlorophenol, 2-amino-5-chlorophenol, 2-amino-4-chlorophenol, 5-amino-2,4-dichlorophenol, 4-amino-3,6-dichlorophenol, 2-amino-4-chloro-6-nitrophenol, and 4-amino-2,6-dibromophenol.

3. The phosphazene-based polymer of claim 1, wherein the polymer is selected from the group consisting of the following compounds:

poly[(isoleucineethylester) (aminomethoxypolyethyleneglycol550, aminoethyl methacrylate)phosphazene]; poly[(isoleucineethylester) (aminomethoxypolyethyleneglycol550, aminoethyl methacrylate)phosphazene]; poly[(isoleucineethylester) (aminomethoxypolyethyleneglycol550, aminoethyl methacrylate)phosphazene]; poly[(isoleucineethylester) (aminomethoxypolyethyleneglycol550, aminoethyl methacrylate)phosphazene]; poly[(isoleucineethylester) (aminomethoxypolyethyleneglycol750, aminoethyl methacrylate)phosphazene]; poly[(isoleucineethylester) (aminomethoxypolyethyleneglycol550, hydroxyethyl methacrylate)phosphazene]; poly[(isoleucineethylester) (aminomethoxypolyethyleneglycol750, hydroxyethyl methacrylate)phosphazene]; poly[(isoleucineethylester) (aminomethoxypolyethyleneglycol550, glycylglycine) (glycylglycylaminoethyl methacrylate)phosphazene]; poly[(isoleucineethylester) (aminomethoxypolyethyleneglycol550, glycylglycine) (glycylglycylhydroxyethyl methacrylate)phosphazene]; poly[(isoleucineethylester) (aminomethoxypolyethyleneglycol550, cystine ethyl ester)phosphazene]; poly[(isoleucineethylester) (aminomethoxypolyethyleneglycol550, cystine ethyl ester)phosphazene]; poly[(isoleucineethylester) (aminomethoxypolyethyleneglycol750, cystine ethyl ester)phosphazene]; poly[(isoleucineethylester) (aminomethoxypolyethyleneglycol550, ethyl-2-(O-glycyl) lactate) (cystine ethyl ester)phosphazene]; poly[(isoleucineethylester) (aminomethoxypolyethyleneglycol550, ethyl-2-(O-glycyl)lactate) (glycylcystine ethyl ester) phosphazene]; poly[(isoleucineethylester) (aminomethoxypolyethyleneglycol550, glycylglycine) (glycylglycylcystine ethyl ester)phosphazene]; poly [(isoleucineethylester) (aminomethoxypolyethyleneglycol550, cysteamine) phosphazene]; poly[(isoleucineethylester) (aminomethoxypolyethyleneglycol550, glycylglycine) (glycylglycylcyteamine)phosphazene]; poly [(isoleucineethylester) (aminomethoxypolyethyleneglycol550, tyramine)phosphazene]; and poly[(isoleucineethylester) (aminomethoxypolyethyleneglycol550, glycylglycine) (glycylglycyltyramine)phosphazene]poly [(isoleucineethylester) (aminomethoxypolyethyleneglycol550, tyrosine)phosphazene]; and poly[(isoleucineethylester) (aminomethoxypolyethyleneglycol550, glycylglycine) (glycylglycyltyrosine)phosphazene], poly [(isoleucineethylester) (aminomethoxypolyethyleneglycol550, aminoethylsuccinate) (aminoethylsuccinateaminoethyl methacrylate)phosphazene], poly[(isoleucineethylester) (aminomethoxypolyethyleneglycol550, aminoethylsuccinate) (aminoethylsuccinatehydroxyethyl methacrylate)phosphazene], poly[(isoleucineethylester) (aminomethoxypolyethyleneglycol550, aminoethylsuccinate) (aminoethylsuccinatecystine ethyl ester)phosphazene], poly[(isoleucineethylester) (aminomethoxypolyethyleneglycol550, aminoethylsuccinate) (aminoethylsuccinate cysteamine)phosphazene], poly[(isoleucineethylester) (aminomethoxypolyethyleneglycol550, aminoethylsuccinate) (aminoethylsuccinatetyramine)phosphazene], and poly [(isoleucineethylester) (aminomethoxypolyethyleneglycol550, aminoethylsuccinate) (aminoethylsuccinatetyrosinemethylester)phosphazene].

4. A method of preparing a phosphazene-based polymer of the following Chemical Formula 1, comprising:

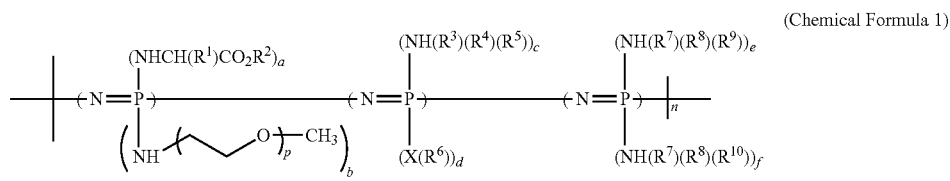

(Chemical Formula 1)

(1) polymerizing a phosphazene trimer of the Chemical Formula 2 to obtain a dichlorophosphazene linear polymer of the Chemical Formula 3;

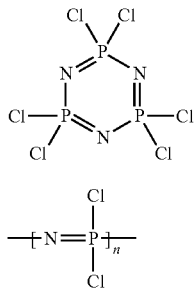

(Chemical Formula 2)

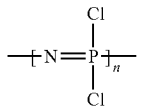

(Chemical Formula 3)

(where, n ranges from 1 to 100000)

(2) reacting the compound of the Chemical Formula 3 obtained in step (1) with 0.01 to 1.9 equivalent of an amino acid ester or a salt thereof having the following Chemical Formula 4;

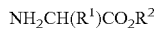  NH$_2$CH(R$^1$)CO$_2$R$^2$  (Chemical Formula 4)

(3) reacting the resulting product of the step (2) with 0 to 1.9 equivalent of amino acid, a peptide, a depsipeptide ester or salts thereof of Chemical Formula 5;

  NH$_2$R3R4R$^5$  (Chemical Formula 5)

(4) reacting the resulting product of the step (3) with 0.01 to 1.9 equivalent of a substitutent being capable of cross-linking of the following Chemical Formula 6 or a salt thereof;

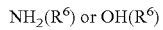  NH$_2$(R$^6$) or OH(R$^6$)  (Chemical Formula 6)

(5) reacting the resulting product of the step (3) or (4) with 0.01 to 1.9 equivalent of a substituent having a functional group of the Chemical Formula 6 or a salt thereof;

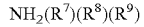  NH$_2$(R$^7$)(R$^8$)(R$^9$)  (Chemical Formula 7)

(6) reacting the resulting product of the step (4) or (5) with aminomethoxy polyethyleneglycol of the Chemical Formula 8 or a salt thereof; and

  NH$_2$(CH$_2$CH$_2$O)$_p$CH$_3$  (Chemical Formula 8)

(7) reacting the resulting product with a compound selected from the group consisting of an acrylate-based compound, a methacrylate-based compound, a acrylamide-based compound, a vinylsulfone-based compound, a thiol-based compound, a cysteine-based compound, a cysteamine-based compound, a mercaptic acid-based compound, an allyl pyrimidine-based compound and compounds including a thiol- or vinyl-group protected with a protecting group of the above compounds, or a tyramine-based compound, a tyrosine-based compound, and a phenol-based compound, wherein, in the above formula, p is a numerical value ranging of 7 to 50, in NHCH(R$^1$)CO$_2$R$^2$, R$^1$ is selected from the group consisting of H, CH$_3$, CH$_2$SH, CH(CH$_3$)$_2$, CH$_2$CH(CH$_3$)$_2$, CH(CH$_3$)C$_2$H$_5$, CH$_2$CH$_2$SCH$_3$, CH$_2$C$_6$H$_5$, CH$_2$C$_6$H$_4$OH, and CH$_2$C$_2$NH$_2$C$_6$H$_4$, and R$^2$ is selected from the group consisting of CH$_3$, C$_2$H$_5$, C$_3$H$_7$, C$_4$H$_9$, CH$_2$C$_6$H$_5$, and CH$_2$CHCH$_2$, in NH(R$^3$)(R$^4$)(R$^5$), R$^3$ is CH(W), R$^4$ is selected from the group consisting of CO$_2$, CONHCH(X)CO$_2$CO$_2$, CH$_2$CO$_2$, and CO$_2$CH(CH$_3$)CO$_2$, and R$^5$ is selected from the group consisting of H, CH$_3$, and C$_2$H$_5$, where W and X are independently selected from the group consisting of H, CH$_3$, CH(CH$_3$)$_2$, CH$_2$CH(CH$_3$)$_2$, CH(CH$_3$)C$_2$H$_5$, CH$_2$CH$_2$SCH$_3$, CH$_2$C$_6$H$_5$, CH$_2$C$_2$NH$_2$C$_6$H$_4$, CO$_2$C$_2$H$_5$, (CH$_2$)$_2$CO$_2$C$_2$H$_5$, CH$_2$OH, CH(CH$_3$)OH, CH$_2$C$_6$H$_4$OH, CH$_2$COOH, CH$_2$CH$_2$COOH, CH$_2$CONH$_2$, C$_4$H$_8$NH$_2$, C$_3$H$_6$NHC(=NH)NH$_2$, CH$_2$C$_3$N$_2$H$_3$, and CH$_2$SH, in XR$^6$, X is N or O, R$^6$ is selected from the group consisting of an acrylate-based compound, a methacrylate-based compound, an acrylamide-based compound, a vinylsulfone-based compound, a thiol-based compound, a cysteine-based compound, a cysteamine-based compound, a mercaptic acid-based compound, an allyl pyrimidine-based compound and compounds including a thiol- or vinyl-group protected with a protecting group of the above compounds, or a tyramine-based compound, a tyrosine-based compound, and a phenol-based compound, NH(R$^7$)(R$^8$)(R$^9$) is a substituent including a functional group, where, R$^7$ is CH(Y), R$^8$ is selected from the group consisting of CH$_2$, C$_2$H$_4$, C$_3$H$_6$, C$_4$H$_8$, CH$_2$C$_6$H$_4$, CH$_2$CO$_2$, C$_2$H$_4$CO$_2$, O, CONHCH(Z)O, CONHCH(Z)CONHCH(M)O, CONHCH(Z)CONHCH(N)CONHCH(L)O, CO, CO$_2$, S, CONHCH(Z)S, CONHCH(Z)CONHCH(M)S, CONHCH(Z)CONHCH(M)CONHCH(L)S, N, CONHCH(Z)N, CONHCH(Z)CONHCH(M)N, CONHCH(Z)CONHCH(M)CONHCH(L)N, CON, COCHNH(Z)CON, COCHNH(Z)CONHCH(M)CON, COCHNH(Z)CONHCH(M)CONHCH(L)CON, CONHCH(Z)CO, COCHNH(Z)CONHCH(M)CO, COCHNH(Z)CONHCH(M)CONHCH(L)CO, CONHCH(Z)CO$_2$, COCHNH(Z)CONHCH(M)CO$_2$, COCHNH(Z)CONHCH(M)CONHCH(L)CO$_2$, [OCH(CH$_3$)CO]$_q$, (OCH$_2$CO)$_q$, [(OCH(CH$_3$)CO]$_q$, [OCO(CH$_2$)$_8$CO]$_q$, [OCOC$_6$H$_5$O(CH$_2$)$_3$OC$_6$H$_5$CO]$_q$, and [OCOC$_6$H$_5$O(CH$_2$)$_6$OC$_6$H$_5$CO]$_q$, and R$^9$ is selected from the group consisting of OH, SH, H, NH$_2$, CH$_3$, C$_2$H$_5$, C$_3$H$_7$, C$_4$H$_9$, CH$_2$C$_6$H$_5$, CH$_2$CHCH$_2$, NHCH(SH)CO$_2$H, NH(CH$_2$)$_q$SH, NH(CH$_2$CH$_2$NH)$_q$H, [NHCH(C$_4$H$_8$NH$_2$)CO]$_q$OH, [NHCH[(CH$_2$)$_3$C(=NH)(NH$_2$)]CO]$_q$OH, folic acid, hyaluronic acid, polyhistidine, cyclodextrin, heparin, chitosan, protamine, and a general protecting group of a functional group, where Y, Z, M, and L are independently selected from the group consisting of H, CH$_3$, CH(CH$_3$)$_2$, CH$_2$CH(CH$_3$)$_2$, CH(CH$_3$)C$_2$H$_5$, CH$_2$CH$_2$SCH$_3$, CH$_2$C$_6$H$_5$, CH$_2$C$_2$NH$_2$C$_6$H$_4$, CO$_2$C$_2$H$_5$, (CH$_2$)$_2$CO$_2$C$_2$H$_5$, CH$_2$OH, CH(CH$_3$)OH, CH$_2$C$_6$H$_4$OH, CH$_2$COOH, CH$_2$CH$_2$COOH, CH$_2$CONH$_2$, C$_4$H$_8$NH$_2$, C$_3$H$_6$NHC(=NH)NH$_2$, CH$_2$C$_3$N$_2$H$_3$, and CH$_2$SH, and q represents a number of a repeating unit and ranges from 1 to 18000, in NH(R$^7$)(R$^8$)(R$^{10}$), R$^7$ and R$^8$ are the same substitutents as in defined in the NH(R$^7$)(R$^8$)(R$^9$), R$^{10}$ is selected from the group consisting of an acrylate-based compound, a methacrylate-based compound, an acrylamide-based compound, a vinylsulfone-based compound, a thiol-based compound, a cysteine-based compound, a cysteamine-based compound, a mercaptic acid-based compound, an allyl pyrimidine-based compound and compounds including a thiol- or vinyl-group protected with a protecting group of the above compounds, or a tyramine-based compound, a tyrosine-based compound, and a phenol-based compound, a, b, c, d, e, and f represent each content of substitutents, a and b range from 0.01 to 1.9, b, c, d, e, and f range from 0 to 1.9, d and f are not simultaneously zero, and a+b+c+d+e+f=2.0, and n represents a polymerization degree of polyphosphazene and ranges 5 to 100000.

5. The method of claim 4, wherein the step (4), step (7) or both steps further comprise adding a polymerization inhibitor in amount of $10^{-4}$ to $10^{-2}$ wt % based on the total weight of reactants.

6. The method of claim 4, wherein when $R^9$ of product of the step (6) is $CH_2C_6H_5$, $CH_2CHCH_2$, a protecting group or OH, the method further comprises performing a step (6-1), after step (6) but before the step (7), of a dehydrogenation reaction, a deallylesterication reaction, a deprotecting reaction, or an esterification reaction.

7. The method of claim 4, wherein the method further comprises performing a step (6-2), after step (6-1) but before the step (7), of reacting the product of the step (6) with a material selected from the group consisting of lysine, arginine, cysteine, thiolan alkylamine, polyethyleneimine, polylysine, polyarginine, folic acid, hyaluronic acid, polyhistidine, cyclodextrin, heparin, chitosan and protamine.

8. The method of claim 4, wherein in the step (6) and step (7), when $R^6$ and $R^{10}$ include a protecting group, the method further comprises performing a step (7-1) after the step (7) of deprotecting the polymer produced in the step (6) and step (7) so that $R^6$ and $R^{10}$ have a thiol functional group or various vinyl functional groups.

9. A hydrogel comprising a phosphazene-based polymer, comprising
a solution of at least one phosphazene-based polymer of the following Chemical Formula 1,
wherein the phosphazene-based polymer includes a chemical cross-linking formed by at least one treatment selected from the group consisting of 1) ultraviolet (UV) radiation; 2) addition of a cross-linking agent selected from the group consisting of a thiol-based cross-linking agent and a vinyl-based cross-linking agent; 3) oxydoreductase addition, or addition of oxydoreductase and hydrogen peroxide; and 4) use of a mixture including a solution of at least one thiol-containing phosphazene-based polymer and a solution of at least one vinyl-containing phosphazene-based polymer, and the phosphazene-based polymer shows a sol-gel behavior in accordance with a temperature:

from the group consisting of H, $CH_3$, and $C_2H_5$, where W and X are independently selected from the group consisting of H, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2H_2C_6H_4$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4H_8NH_2$, $C_3H_6NHC$ ($=$NH)$NH_2$, $CH_2C_3N_2H_3$, and $CH_2SH$, in $XR^6$, X is N or O, $R^6$ is selected from the group consisting of an acrylate-based compound, a methacrylate-based compound, an acrylamide-based compound, a vinylsulfone-based compound, a thiol-based compound, a cysteine-based compound, a cysteamine-based compound, a mercaptic acid-based compound, an allyl pyrimidine-based compound and compounds including a thiol- or vinyl-group protected with a protecting group of the above compounds, or a tyramine-based compound, a tyrosine-based compound, and a phenol-based compound, $NH(R^7)(R^8)(R^9)$ is a substituent including a functional group, where, $R^7$ is CH(Y), $R^8$ is selected from the group consisting of $CH_2$, $C_2H_4$, $C_3H_6$, $C_4H_8$, $CH_2C_6H_4$, $CH_2CO_2$, $C_2H_4CO_2$, O, CONHCH(Z)O, CONHCH(Z)CONHCH(M)O, CONHCH(Z)CONHCH(N)CONHCH(L)O, CO, $CO_2$, S, CONHCH(Z)S, CONHCH(Z)CONHCH(M)S, CONHCH(Z)CONHCH(L)S, N, CONHCH(Z)N, CONHCH(Z)CONHCH(M)N, CONHCH(Z)CONHCH(M)CONHCH(L)N, CON, COCHNH(Z)CON, COCHNH(Z)CONHCH(M)CON, COCHNH(Z)CONHCH(M)CONHCH(L)CON, CONHCH(Z)CO, COCHNH(Z)CONHCH(M)CO, COCHNH(Z)CONHCH(M)CONHCH(L)CO, CONHCH(Z)CO$_2$, COCHNH(Z)CONHCH(M)CO$_2$, COCHNH(Z)CONHCH(M)CONHCH(L)CO$_2$, $[OCH(CH_3)CO]_q$, $(OCH_2CO)_q$, $[(OCH(CH_3)CO]_q$, $[OCO(CH_2)_8CO]_q$, $[OCOC_6H_5O(CH_2)_3OC_6H_5CO]_q$, and $[OCOC_6H_5O(CH_2)_6OC_6H_5CO]_q$, and $R^9$ is selected from the group consisting of OH, SH, H, $NH_2$, $CH_3$, $C_2H_5$, $C_3H_7$, $C_4H_9$, $CH_2C_6H_5$, $CH_2CHCH_2$, NHCH(SH)CO$_2$H, $NH(CH_2)_q$SH, $NH(CH_2CH_2NH)_q$H, $[NHCH(C_4H_8NH_2)CO]_q$OH, $[NHCH[(CH_2)_3C(=NH)(NH_2)]CO]_q$OH, folic acid, hyaluronic acid, polyhistidine, cyclodextrin, heparin, chitosan, protamine, and a general protecting group of a functional group, (Chemical Formula 1)

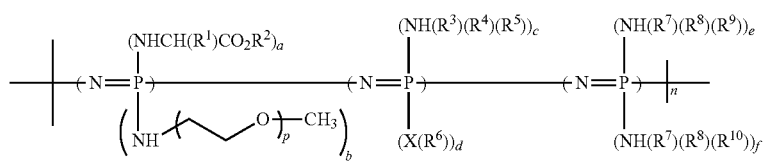

wherein, in the above formula,
p is a numerical value ranging of 7 to 50,
in NHCH($R^1$)CO$_2R^2$, $R^1$ is selected from the group consisting of H, $CH_3$, $CH_2SH$, $CH(CH_3)_2$, $CH_2CH(CH_3)_2$, $CH(CH_3)C_2H_5$, $CH_2CH_2SCH_3$, $CH_2C_6H_5$, $CH_2C_6H_4OH$, and $CH_2C_2H_2C_6H_4$, and $R^2$ is selected from the group consisting of $CH_3$, $C_2H_5$, $C_3H_7$, $C_4H_9$, $CH_2C_6H_5$, and $CH_2CHCH_2$,
in $NH(R^3)(R^4)(R^5)$, $R^3$ is CH(W), $R^4$ is selected from the group consisting of $CO_2$, CONHCH(X)CO$_2$CO$_2$, $CH_2CO_2$, and $CO_2CH(CH_3)CO_2$, and $R^5$ is selected where Y, Z, M, and L are independently selected from the group consisting of H, $CH_3$, $CH(CH_3)_2$, $CH_2CH(CH_3)_2$, $CH(CH_3)C_2H_5$, $CH_2CH_2SCH_3$, $CH_2C_6H_5$, $CH_2C_2H_2C_6H_4$, $CO_2C_2H_5$, $(CH_2)_2CO_2C_2H_5$, $CH_2OH$, $CH(CH_3)OH$, $CH_2C_6H_4OH$, $CH_2COOH$, $CH_2CH_2COOH$, $CH_2CONH_2$, $C_4H_8NH_2$, $C_3H_6NHC$ ($=$NH)$NH_2$, $CH_2C_3N_2H_3$, and $CH_2SH$, and q represents a number of a repeating unit and ranges from 1 to 18000,
in $NH(R^7)(R^8)(R^{10})$, $R^7$ and $R^8$ are the same substitutents as in defined in the $NH(R^7)(R^8)(R^9)$, $R^{10}$ is selected from the group consisting of an acrylate-based compound, a methacrylate-based compound, an acrylamide-based compound, a vinylsulfone-based compound, a thiol-based compound, a cysteine-based compound, a cysteamine-based compound, a mercaptic acid-based compound, an allyl pyrimidine-based compound and compounds including a thiol- or vinyl-group protected with a protecting group of the above compounds, or a tyramine-based compound, a tyrosine-based compound, and a phenol-based compound, a, b, c, d, e, and f represent each content of substitutents, a and b range from 0.01 to 1.9, b, c, d, e, and f range from 0 to 1.9, d and f are not simultaneously zero, and a+b+c+d+e+f=2.0, and n represents a polymerization degree of polyphosphazene and ranges 5 to 100000.

10. The hydrogel of claim 9, wherein the solution of the phosphazene-based polymer comprises a mixture of a solution of at least one phosphazene-based polymer where $R^6$ and $R^{10}$ are vinyl, and a solution of at least one phosphazene-based polymer where $R^6$ and $R^{10}$ are thiol, and the vinyl and thiol react with each other to form a cross-link.

11. The hydrogel of claim 9, wherein the hydrogel further comprises at least one a photoinitiator selected from the group consisting of a ketone-based compound, a phosphine oxide-based compound, an alkylester-based compound, a benzoyl-based compound, titanate, an iodonium salt, a dibenzoyl-based compound, a thiocarbonate-based compound, a dione-based compound and potassium sulfate at $1 \times 10^{-6}$ to 10 wt % based on the total weight of the phosphazene-based polymer, and the hydrogel comprises cross-linking due to ultraviolet (UV) radiation.

12. The hydrogel of claim 9, wherein the hydrogel further comprises a cross-linking agent selected from the group consisting of a vinyl-based cross-linking agent and a thiol-based cross-linking agent at $1 \times 10^{-6}$ to 30 wt % based on the total weight of the phosphazene-based polymer, vinyl or thiol of the cross-linking agent reacts with thiol or vinyl of a phosphazene-based polymer to form a cross-link.

13. The hydrogel of claim 9, wherein the oxydoreductase is at least one selected from the group consisting of trans-glutaminase, laccase, bilirubin oxidase (BOD), manganase (II), hematin, horseradish peroxidase, the enzyme is included in an amount of $1 \times 10^{-6}$ to 200 wt % based on the total weight of the phosphazene-based polymer, the enzyme reacts with tyramine, tyrosine or a phenol-based compound of the phosphazene-based polymer to from a cross-link.

14. The hydrogel of claim 9, wherein the phosphazene-based polymer is included at a concentration of 1 to 50 wt % in the solution.

15. A method of preparing a hydrogel comprising:
preparing a solution of at least one phosphazene-based polymer according to claim 1; and
forming a chemical cross-linking in the polymer to prepare a hydrogel,
the chemical cross-linking is formed by one of the four following methods:
1) use of a mixture including a solution of at least one thiol-containing phosphazene-based polymer and a solution of at least one vinyl-containing phosphazene-based polymer;
2) ultraviolet (UV) radiation;
3) addition of a cross-linking agent selected from the group consisting of a vinyl-based cross-linking agent and a thiol-based cross-linking agent; and
4) oxydoreductase addition, or addition of at least one oxydoreductase and hydrogen peroxide.

16. The method of claim 15, wherein the solution of the phosphazene-based polymer comprises a mixture of a solution of at least one phosphazene-based polymer where $R^6$ and $R^{10}$ are vinyl, and a solution of at least one phosphazene-based polymer where $R^6$ and $R^{10}$ are thiol, and the vinyl and thiol react with each other to form a cross-link.

17. The method of claim 15, wherein the method further comprises adding a photoinitiator to generate a radical by photo-radiation selected from the group consisting of a ketone-based compound, a phosphine oxide-based compound, an alkylester-based compound, a benzoyl-based compound, titanate, an iodonium salt, a dibenzoyl-based compound, a thiocarbonate-based compound, a dione-based compound, and potassium sulfate at $1 \times 10^{-6}$ to 10 wt % based on the total weight of the phosphazene-based polymer, and irradiating the composition with ultraviolet (UV) to form a cross-link.

18. The method of claim 15, wherein the method further comprises adding a cross-linking agent selected from the group consisting of a vinyl-based cross-linking agent having two or more vinyl or a thiol-based cross-linking agent having thiol in an amount of $1 \times 10^{-6}$ to 30 wt % based on the total weight of the phosphazene-based polymer, and reacting the vinyl or thiol of the cross-linking agent with thiol or vinyl of a phosphazene-based polymer to form a cross-link.

19. The method of claim 15, wherein the method further comprises adding oxydoreductase in an amount of $1 \times 10^{-6}$ to 200 wt % based on the total weight of the phosphazene-based polymer, and reacting the enzyme and tyramine or tyrosine of the phosphazene-based polymer to form a cross-link.

20. A carrier for a physiological active material, comprising
a hydrogel including at least one phosphazene-based polymer according to claim 9, and
a physiological active material of at least one drug and cell selected from the group consisting of a protein, a polypeptide, a peptide, a vaccine, a gene, a hormone, an anti-cancer drug, and angiogenesis inhibitor.

21. The carrier for the physiological active material of claim 20, wherein the carrier further comprises at least one additive selected from the group consisting of a cationic polymer having a molecular weight of 200 to 750,000, an anionic polymer having a molecular weight of 200 to 750,000, amino acid, a peptide, a protein, fatty acid, phospholipids, vitamin series, a drug, polyethyleneglycol ester, steroids, amine compound, an acryl-based copolymer, an organic solvent, a preservative, sugar series, a polyol, a polyol including a sugar, amino acid including a sugar, a surfactant, ion including a sugar, silicate, metal salts and ammonium salts in an amount of $1 \times 10^{-6}$ to 30 wt % based on the total weight of the carrier for the physiological active material.

22. The carrier for the physiological active material of claim 20, wherein the physiological active material is a drug selected from the group consisting of a protein, a polypeptide, a peptide, a vaccine, a gene, a hormone, an anti-cancer drug, and an angiogenesis inhibitor in an amount of $1 \times 10^{-8}$ to 50% by volume based on the total volume of the carrier for the physiological active material.

23. The carrier for the physiological active material of claim 20, wherein the physiological active material is at least one cell selected from the group consisting of a preosteoblast, a chondrocyte, a umbilical vein endothelial cell (UVEC), a osteoblast, an adult stem cell, a schwann cell, an oligodendrocyte, hepatocyte, a mural cell (combined with the UVEC), myoblast, an insulin secreting cell, an endothelial cell, a smooth muscle cell, a fibroblast, a β cell, an endodermal cell, a hepatic stem cell, a juxtaglomerular cell, skeletal muscle cell, a keratinocyte, a melanocyte, a langerhans cell, a merkel cell, a dermal fibroblast, and a preadipocyte in an amount of $1 \times 10^{-8}$ to 50% by volume based on the total volume of the carrier for the physiological active material.

24. The method of claim 6, wherein the method further comprises performing a step of (6-2), after the step (6-1) but before the step (7), of reacting the product of the step (6-1) with a material selected from the group consisting of lysine, arginine, cysteine, thiolan alkylamine, polyethyleneimine, polylysine, polyarginine, folic acid, hyaluronic acid, polyhistidine, cyclodextrin, heparin, chitosan and protamine.

* * * * *